(12) United States Patent
Lee

(10) Patent No.: US 6,486,157 B1
(45) Date of Patent: Nov. 26, 2002

(54) USE OF INSECTICIDES IN PEST CONTROL

(75) Inventor: Bruce Lee, Bad Krozingen (DE)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 09/600,379

(22) PCT Filed: Jan. 14, 1999

(86) PCT No.: PCT/EP99/00184

§ 371 (c)(1),
(2), (4) Date: Sep. 27, 2000

(87) PCT Pub. No.: WO99/35910

PCT Pub. Date: Jul. 22, 1999

(30) Foreign Application Priority Data

| Jan. 16, 1998 | (CH) | 82/98 |
| Jan. 16, 1998 | (CH) | 83/98 |
| Jan. 16, 1998 | (CH) | 85/98 |
| Jan. 16, 1998 | (CH) | 81/98 |

(51) Int. Cl.⁷ .............................................. A01N 43/64
(52) U.S. Cl. ....................................................... 514/242
(58) Field of Search ........................................ 514/242

(56) References Cited

U.S. PATENT DOCUMENTS

| 4,107,294 A | 8/1978 | Chauthani ..................... 424/93 |
| 4,798,837 A | 1/1989 | Drabek et al. ............... 514/594 |
| 6,060,489 A | 5/2000 | Erdelen et al. ............. 514/341 |

FOREIGN PATENT DOCUMENTS

| CA | 2005658 | 6/1990 |
| EP | A 374 753 | 6/1990 |
| FR | 2 720 230 | 12/1995 |
| WO | WO 94/16565 | 8/1994 |
| WO | WO 96/01055 | 1/1996 |
| WO | WO 96/28023 | 9/1996 |
| WO | WO 96/37105 | 11/1996 |
| WO | WO 97/26339 | 7/1997 |
| WO | WO 9745017 | 12/1997 |

OTHER PUBLICATIONS

Tomlin, The Pesticide Manual Incorporating The Agrochemicals Handbook, Tenth Edition (1995), pp. 868–869.*

Database cropu, STN–International, Accession No. 98–88286, Efficacy of selected insecticides against cotton aphid on cotton, XP002102656 abstract, and Arthropod Manage Tests, vol. 23, p. 248, 1998, K.D. Torrey et al.

Database CROPU, STN–International, Accession No. 98–88274, XP002102657 abstract, Evaluation of insecticides for control of aphids in NuCotn 33b cotton, 1997, M. S. Howell, et al.

* cited by examiner

Primary Examiner—Allen J. Robinson
(74) Attorney, Agent, or Firm—William A. Teoli, Jr.; Rose M. Allen

(57) ABSTRACT

The present invention is a method of controlling pests in and on transgenic crops of useful plants, such as, for example, in crops of maize, cereals, soya beans, tomatoes, cotton, potatoes, rice and mustard, where pymetrozine, profenofos, a benzoylurea-derivative, especially lufenuron; or a carbamat-derivative, especially fenoxycarb; in free form or in agrochemically useful salt form and at least one auxiliary, is applied to the pests or their environment, or to the transgenic crop plant itself.

3 Claims, No Drawings

USE OF INSECTICIDES IN PEST CONTROL

This application is a 371 of PCT/EP99/00184, filed Jan. 14, 1999

The present invention relates to a novel method of controlling pests in and on transgenic crops of useful plants with pymetrozine; profenofos; a benzoylurea-derivative, especially lufenuron; or a carbamat-derivative, especially fenoxycarb.

Certain pest control methods are proposed in the literature. However, these methods are not fully satisfactory in the field of pest control, which is why there is a demand for providing further methods for controlling and combating pests, in particular insects and repre-sentatives of the order Acarina, or for protecting plants, especially crop plants. This object is achieved according to the invention by providing the present method.

The present invention therefore relates to a method of controlling pests in crops of transgenic useful plants, such as, for example, in crops of maize, cereals, soya beans, tomatoes, cotton, potatoes, rice and mustard, characterized in that a pesticidal composition comprising pymetrozine; profenofos; a benzoylurea-derivative, especially lufenuron; or a carbamat-derivative, especially fenoxycarb, in free form or in agrochemically useful salt form and at least one auxiliary is applied to the pests or their environment, in particular to the crop plant itself; to the use of the composition in question and to propagation material of transgenic plants which has been treated with it.

Surprisingly, it has now emerged that the use of pymetrozine; profenofos; a benzoylurea-derivative, especially lufenuraon; or a carbamat-derivative, especially fenoxycarb, for controlling pests on transgenic useful plants which contain—for instance—one or more genes expressing a pesticidally, particularly insecticidally, acaricidally, nematocidally or fugicidally active ingredient, or which are tolerant against herbicides or resistent against the attack of fungi, has a synergistic effect. It is highly surprising that the use of pymetrozine; profenofos; a benzoylurea-derivative, or a carbamat-derivative in combination with a transgenic plant exceeds the additive effect, to be expected in principle, on the pests to be controlled and thus extends the range of action of the said active ingredients and of the active principle expressed by the transgenic plant in particular in two respects:

In particular, it has been found, surprisingly, that within the scope of invention the pesticidal activity of a active ingredient according to the invention in combination with the effect expressed by the transgenic useful plant, is not only additive in comparison with the pesticidal activities of the active ingredient according to the invention alone and of the transgenic crop plant alone, as can generally be expected, but that a synergistic effect is present. The term "synergistic", however, is in no way to be understood in this connection as being restricted to the pesticidal activity, but the term also refers to other advantageous properties of the method according to the invention compared with the active ingredient according to the invention and the transgenic useful plant alone. Examples of such advantageous properties which may be mentioned are: extension of the pesticidal spectrum of action to other pests, for example to resistant strains; reduction in the application rate of the active ingredient according to the invention, or sufficient control of the pests with the aid of the compositions according to the invention even at an application rate of the active ingredient according to the invention alone and the transgenic useful plant alone are entirely ineffective; enhanced crop safety; improved quality of produce such as higher content of nutrient or oil, better fiber quality, enhanced shelf life, reduced content of toxic products such as mycotoxins, reduced content of residues or unfavorable constituents of any kind or better digestability; improved tolerance to unfavorable temperatures, draughts or salt content of water; enhanced assimilation rates such as nutrient uptake, water uptake and photosynthesis; favorable crop properties such as altered leaf aerea, reduced vegetative growth, increased yields, favorable seed shape/seed thickness or germination properties, altered colonialisation by saprophytes or epiphytes, reduction of senescense, improved phytoalexin production, improved of accelerated ripening, flower set increase, reduced boll fall and shattering, better attraction to beneficials and predators, increased pollination, reduced attraction to birds; or other advantages known to those skilled in the art. pymetrozine, 2,3,4,5-Tetrahydro-3-oxo-4-[(pyridin-3-yl)-methylenamino]-6-methyl-1,2,4-triazin, is known from The Pesticide Manual, $10^{th}$Ed. (1994), The British Crop Protection Council, London, page 868.

The active ingredients used according to the invention are know to those skilled in the art, specifically:

Carbamates are known for instance from EP-A-004334.
Fenoxycarb, Ethyl 2-(4-Phenoxyphenoxy) ethylcarbamat, is known from The Pesticide Manual, $9^{th}$Ed. (1991), The British Crop Protection Council, London, page 375;

Benzoylureas are known for instance from EP-A-179022; lufenuron is known from The Pesticide Manual, $10^{th}$Ed. (1994), The British Crop Protection Council, London, page 628; and Profenofos, O-4-Brom-2-chlorphenyl O-Ethyl S-Propyl Phosphorothioat, is known from The Pesticide Manual, $9^{th}$Ed. (1991), The British Crop Protection Council, London, page 705.

The agrochemically compatible salts of the active ingredients according to the invention are, for example, acid addition salts of inorganic and organic acids, in particular of hydrochloric acid, hydrobromic acid, sulfuric acid, nitric acid, perchloric acid, phosphoric acid, formic acid, acetic acid, trifluoroacetic acid, oxalic acid, malonic acid, toluene-sulfonic acid or benzoic acid. Preferred within the scope of the present invention is a composition known per se which comprises, as active ingredient, pymetrozine, profenofos, lufenuron or fenoxacarb; each in the free form.

The transgenic plants used according to the invention are plants, or propagation material thereof, which are transformed by means of recombinant DNA technology in such a way that they are—for instance—capable of synthesizing selectively acting toxins as are known, for example, from toxin-producinginvertebrates, especially of the phylum Arthropoda, as can be obtained from Bacillus thuringiensis strains; or as are known from plants, such as lectins; or in the alternative capable of expressing a herbicidal or fungicidal resistance. Examples of such toxins, or transgenic plants which are capable of synthesizing such toxins, have been disclosed, for example, in EP-A-0 374 753, WO 93/07278, WO 95/34656, EP-A-0 427 529 and EP-A-451 878 and are incorporated by reference in the present application.

The methods for generating such transgenic plants are widely known to those skilled in the art and described, for example, in the publications mentioned above.

The toxins which can be expressed by such transgenic plants include, for example, toxins, such as proteins which have insecticidal properties and which are expressed by transgenic plants, for example Bacillus cereus proteins or Bacillus popliae proteins; or Bacillus thuringiensis endotoxins (B.t.), such as CryIA(a), CryIA(b), CryIA(c), CryIIA, CryIIIA, CryIIIB2 or CytA; VIP1; VIP2; VIP3; or insecticidal proteins of bacteria colonising nematodes like Photorhabdus spp or Xenorhabdus spp such as Photorhabdus luminescens, Xenorhabdus nematophilus etc.; proteinase inhibitors, such as trypsin inhibitors, serine protease inhibitors, patatin, cystatin, papain inhibitors; ribosome-inactivating proteins (RIP), such as ricin, maize RIP, abrin, luffin, saporin or bryodin; plant lectins such as pea lectins, barley lectins or snowdrop lectins; or agglutinins; toxins produced by animals, such as scorpion toxins, spider venoms, wasp venoms and other insect-specific neurotoxins; steroid metabolism enzymes, such as 3-hydroxysteroid oxidase, ecdysteroid UDP-glycosyl transferase, cholesterol oxidases, ecdysone inhibitors, HMG-COAreductase, ion channel blockers such as sodium and calcium, juvenile hormone esterase, diuretic hormone receptors, stilbene synthase, bibenzyl synthase, chitinases and glucanases.

Examples of known transgenic plants which comprise one or more genes which encode insecticidal resistance and express one or more toxins are the following: KnockOut® (maize), YieldGard® (maize); NuCOTN 33B® (cotton), Boligard® (cotton), NewLeaf® (potatoes), NatureGard® and Protecta®.

The following tables comprise further examples of targets and principles and crop phenotypes of transgenic crops which show tolerance against pests mainly insects, mites, nematodes, virus, bacteria and diseases or are tolerant to specific herbicides or classes of herbicides.

TABLE A1

Crop: Maize

| Effected target or expressed principle(s) | Crop phenotype/Tolerance to |
|---|---|
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkane-carboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzonitriles such as Bromoxynil and Ioxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 | Xenobiotics and herbicides such as Sulfonylureas |
| Dimboa biosynthesis (Bx1 gene) | Helminthosporium turcicum, Rhopalosiphum maydis, Diplodia maydis, Ostrinia nubilalis, lepidoptera sp. |
| CMIII (small basic maize seed peptide | plant pathogens eg. fusarium, alternaria, sclerotina |

TABLE A1-continued

Crop: Maize

| Effected target or expressed principle(s) | Crop phenotype/Tolerance to |
|---|---|
| Corn- SAFP (zeamatin) | plant pathogens eg. fusarium, alternaria, sclerotina, rhizoctonia, chaetomium, phycomyces |
| Hm1 gene | Cochliobulus |
| Chitinases | plant pathogens |
| Glucanases | plant pathogens |
| Coat proteins | viruses such as maize dwarf mosaic virus, maize chlorotic dwarf virus |
| *Bacillus thuringiensis* toxins, VIP 3, *Bacilius cereus* toxins, Photorabdus and Xenorhabdus toxins | lepidoptera, coleoptera, diptera, nematodes, eg. ostrinia nubilalis, heliothis zea, armyworms eg. spodoptera frugiperda, corn rootworms, sesamia sp., black cutworm, asian corn borer,weevils |
| 3-Hydroxysteroid oxidase | lepidoptera, coleoptera, diptera, nematodes, eg. ostrinia nubilalis, heliothis zea, armyworms eg. spodoptera frugiperda, corn rootworms, sesamia sp., black cutworm, asian corn borer, weevils |
| Peroxidase | lepidoptera, coleoptera, diptera, nematodes, eg. ostrinia nubilalis, heliothis zea, armyworms eg. spodoptera frugiperda, corn rootworms, sesamia sp., black cutworm, asian corn borer, weevils |
| Aminopeptidase inhibitors eg. Leucine aminopeptidase inhibitor (LAPI) | lepidoptera, coleoptera, diptera, nematodes, eg. ostrinia nubilalis, heliothis zea, armyworms eg. spodoptera frugiperda, corn rootworms, sesamia sp., black cutworm, asian corn borer, weevils |
| Limonene synthase | corn rootworms |
| Lectines | lepidoptera, coleoptera, diptera, nematodes, eg. ostrinia nubilalis, heliothis zea, armyworms eg. spodoptera frugiperda, corn rootworms, sesamia sp., black cutworm, asian corn borer, weevils |
| Protease inhibitors eg. cystatin, patatin, virgiferin, CPTI | weevils, corn rootworm |
| ribosome inactivating protein | lepidoptera, coleoptera, diptera, nematodes, eg. ostrinia nubilalis, heliothis zea, armyworms eg. spodoptera frugiperda, corn rootworms, sesamia sp., black cutworm, asian corn borer, weevils |
| maize 5C9 polypeptide | lepidoptera, coleoptera, diptera, nematodes, eg. ostrinia nubilalis, heliothis zea, armyworms eg. spodoptera frugiperda, corn rootworms, sesamia sp., black cutworm, asian corn borer, weevils |
| HMG-CoA reductase | lepidoptera, coleoptera, diptera, nematodes, eg. ostrinia nubilalis, heliothis zea, armyworms eg. spodoptera frugiperda, corn rootworms, sesamia sp., black cutworm, asian corn borer, weevils |

TABLE A2

Crop Wheat

| Effected target or expressed principle(s) | Crop phenotype/Tolerance to |
|---|---|
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkane-carboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzo-nitriles such as Bromoxynil and Ioxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 | Xenobiotics and herbicides such as Sulfonylureas |
| Antifungal polypeptide AlyAFP | plant pathogenes eg septoria and fusarioum |
| glucose oxidase | plant pathogenes eg. fusarium, septoria |
| pyrrolnitrin synthesis genes | plant pathogenes eg. fusarium, septoria |
| serine/threonine kinases | plant pathogenes eg. fusarium, septoria and other diseases |
| Hypersensitive response eliciting polypeptide | plant pathogenes eg. fusarium, septoria and other diseases |
| Systemic acquires resistance (SAR) genes | viral, bacterial, fungal, nematodal pathogens |
| Chitinases | plant pathogenes |
| Glucanases | plant pathogenes |
| double stranded ribonuclease | viruses such as BYDV and MSMV |
| Coat proteins | viruses such as BYDV and MSMV |
| *Bacillus thuringiensis* toxins, VIP 3, *Bacillus cereus* toxins, Photorabdus and Xenorhabdus toxins | lepidoptera, coleoptera, diptera, nematodes, |
| 3-Hydroxysteroid oxidase | lepidoptera, coleoptera, diptera, nematodes, |
| Peroxidase | lepidoptera, coleoptera, diptera, nematodes, |
| Aminopeptidase inhibitors eg. Leucine aminopeptidase inhibitor | lepidoptera, coleoptera, diptera, nematodes, |
| Lectines | lepidoptera, coleoptera, diptera, nematodes, aphids |
| Protease inhibitors eg. cystatin, patatin, virgiferin, CPTI | lepidoptera, coleoptera, diptera, nematodes, aphids |
| ribosome inactivating protein | lepidoptera, coleoptera, diptera, nematodes, aphids |
| HMG-CoA reductase | lepidoptera, coleoptera, diptera, nematodes, eg. ostrinia nubilalis, heliothis zea, armyworms eg. spodoptera frugiperda, corn rootworms, sesamia sp., black cutworm, asian corn borer, weevils |

TABLE A3

Crop Barley

| Effected target or expressed principle(s) | Crop phenotype/Tolerance to |
|---|---|
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkane-carboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzo-nitriles such as Bromoxynil and Ioxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 | Xenobiotics and herbicides such as Sulfonylureas |
| Antifungal polypeptide AlyAFP | plant pathogenes eg septoria and fusarioum |
| glucose oxidase | plant pathogenes eg. fusarium, septoria |
| pyrrolnitrin synthesis genes | plant pathogenes eg. fusarium, septoria |
| serine/threonine kinases | plant pathogenes eg. fusarium, septoria and other diseases |
| Hypersensitive response eliciting polypeptide | plant pathogenes eg. fusarium, septoria and other diseases |
| Systemic acquires resistance (SAR) genes | viral, bacterial, fungal, nematodal pathogens |
| Chitinases | plant pathogenes |
| Glucanases | plant pathogenes |
| double stranded ribonuclease | viruses such as BYDV and MSMV |
| Coat proteins | viruses such as BYDV and MSMV |
| *Bacillus thuringiensis* toxins, VIP 3, *Bacilius cereus* toxins, Photorabdus and Xenorhabdus toxins | lepidoptera, coleoptera, diptera, nematodes, |
| 3-Hydroxysteroid oxidase | lepidoptera, coleoptera, diptera, nematodes, |
| Peroxidase | lepidoptera, coleoptera, diptera, nematodes, |
| Aminopeptidase inhibitors eg. Leucine aminopeptidase inhibitor | lepidoptera, coleoptera, diptera, nematodes, |
| Lectines | lepidoptera, coleoptera, diptera, nematodes, aphids |
| Protease inhibitors eg. cystatin, patatin, virgiferin, CPTI | lepidoptera, coleoptera, diptera, nematodes, aphids |
| ribosome inactivating protein | lepidoptera, coleoptera, diptera, nematodes, aphids |
| HMG-CoA reductase | lepidoptera, coleoptera, diptera, nematodes, aphids |

TABLE A4

Crop Rice

| Effected target or expressed principle(s) | Crop phenotype/Tolerance to |
| --- | --- |
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkane-carboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzo-nitriles such as Bromoxynil and Ioxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 | Xenobiotics and herbicides such as Sulfonylureas |
| Antifungal polypeptide AlyAFP | plant pathogenes |
| glucose oxidase | plant pathogenes |
| pyrrolnitrin synthesis genes | plant pathogenes |
| serine/threonine kinases | plant pathogenes |
| Phenylalanine ammonia lyase (PAL) | plant pathogenes eg bacterial leaf blight and rice blast, inducible |
| phytoalexins | plant pathogenes eg bacterial leaf blight and rice blast |
| B-1,3-glucanase antisense | plant pathogenes eg bacterial leaf blight and rice blast |
| receptor kinase | plant pathogenes eg bacterial leaf blight and rice blast |
| Hypersensitive response eliciting polypeptide | plant pathogenes |
| Systemic acquires resistance (SAR) genes | viral, bacterial, fungal, nematodal pathogens |
| Chitinases | plant pathogenes eg bacterial leaf blight and rice blast |
| Glucanases | plant pathogenes |
| double stranded ribonuclease | viruses such as BYDV and MSMV |
| Coat proteins | viruses such as BYDV and MSMV |
| *Bacillus thuringiensis* toxins, VIP 3, *Bacillus cereus* toxins, Photorabdus and Xenorhabdus toxins | lepidoptera eg. stemborer, coleoptera eg rice water weevil, diptera, rice hoppers eg brown rice hopper |
| 3-Hydroxysteroid oxidase | lepidoptera eg. stemborer, coleoptera eg rice water weevil, diptera, rice hoppers eg brown rice hopper |
| Peroxidase | lepidoptera eg. stemborer, coleoptera eg rice water weevil, diptera, rice hoppers eg brown rice hopper |
| Aminopeptidase inhibitors eg. Leucine aminopeptidase inhibitor | lepidoptera eg. stemborer, coleoptera eg rice water weevil, diptera, rice hoppers eg brown rice hopper |

TABLE A4-continued

Crop Rice

| Effected target or expressed principle(s) | Crop phenotype/Tolerance to |
| --- | --- |
| Lectines | lepidoptera eg. stemborer, coleoptera eg rice water weevil, diptera, rice hoppers eg brown rice hopper |
| Protease inhibitors, | lepidoptera eg. stemborer, coleoptera eg rice water weevil, diptera, rice hoppers eg brown rice hopper |
| ribosome inactivating protein | lepidoptera eg. stemborer, coleoptera eg rice water weevil, diptera, rice hoppers eg brown rice hopper |
| HMG-CoA reductase | lepidoptera eg. stemborer, coleoptera eg rice water weevil, diptera, rice hoppers eg brown rice hopper |

TABLE A5

Crop Soya

| Effected target or expressed principle(s) | Crop phenotype/Tolerance to |
| --- | --- |
| Acetolactate synthase (ALS) | Sulfonylureas, Imidazolinones, Triazolopyrimidines, Pyrimidyioxybenzoates, Phtalides |
| AcetylCoA Carboxylase (ACCase) | Aryloxyphenoxyalkane-carboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzo-nitriles such as Bromoxynil and Ioxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |
| Antifungal polypeptide AlyAFP | bacterial and fungal pathogens such as fusarium, sclerotinia, stemrot |
| oxalate oxidase | bacterial and fungal pathogens such as fusarium, sclerotinia, stemrot |
| glucose oxidase | bacterial and fungal pathogens such as fusarium, sclerotinia, stemrot |
| pyrrolnitrin synthesis genes | bacterial and fungal pathogens such as fusarium, sclerotinia, stemrot |
| serine/threonine kinases | bacterial and fungal pathogens such as fusarium, sclerotinia, stemrot |
| Phenylalanine ammonia lyase (PAL) | bacterial and fungal pathogens such as fusarium, sclerotinia, stemrot |

TABLE A5-continued

Crop Soya

| Effected target or expressed principle(s) | Crop phenotype/Tolerance to |
|---|---|
| phytoalexins | plant pathogenes eg bacterial leaf blight and rice blast |
| B-1,3-glucanase antisense | plant pathogenes eg bacterial leaf blight and rice blast |
| receptor kinase | bacterial and fungal pathogens such as fusarium, sclerotinia, stemrot |
| Hypersensitive response eliciting polypeptide | plant pathogenes |
| Systemic acquires resistance (SAR) genes | viral, bacterial, fungal, nematodal pathogens |
| Chitinases | bacterial and fungal pathogens such as fusarium, sclerotinia, stemrot |
| Glucanases | bacterial and fungal pathogens such as fusarium, sclerotinia, stemrot |
| double stranded ribonuclease | viruses such as BPMV and SbMV |
| Coat proteins | viruses such as BYDV and MSMV |
| *Bacllius thuringiensis* toxins, VIP 3, *Bacillus cereus* toxins, Photorabdus and Xenorhabdus toxins | lepidoptera, coleoptera, aphids |
| 3-Hydroxysteroid oxidase | lepidoptera, coleoptera, aphids |
| Peroxidase | lepidoptera, coleoptera, aphids |
| Aminopeptidase inhibitors eg. Leucine aminopeptidase inhibitor | lepidoptera, coleoptera, aphids |
| Lectines | lepidoptera, coleoptera, aphids |
| Protease Inhibitors eg virgiferin | lepidoptera, coleoptera, aphids |
| ribosome inactivating protein | lepidoptera, coleoptera, aphids |
| HMG-COA reductase | lepidoptera, coleoptera, aphids |
| Barnase | nematodes eg root knot nematodes and cyst nematodes |
| Cyst nematode hatching stimulus | cyst nematodes |
| Antifeeding principles | nematodes eg root knot nematodes and cyst nematodes |

TABLE A6

Crop Potatoes

| Effected target or expressed principle(s) | Crop phenotype/Tolerance to |
|---|---|
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkane-carboxylic acids, cyclohexanediones |
| Hydroxyphenylpyruvate dioxygenase (HPPD) | Isoxazoles such as Isoxaflutol or Isoxachlonol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzo-nitriles such as Bromoxynil and Ioxynil |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |

TABLE A6-continued

Crop Potatoes

| Effected target or expressed principle(s) | Crop phenotype/Tolerance to |
|---|---|
| Cytochrome P450 eg. P450 SU1 or selection | Xenobiotics and herbicides such as Sulfonylureas |
| Polyphenol oxidase or Polyphenol oxidase antisense | blackspot bruise |
| Metallothionein | bacterial and fungal pathogens such as phytophtora |
| Ribonuclease | Phytophtora, Verticillium, Rhizoctonia |
| Antifungal polypeptide AlyAFP | bacterial and fungal pathogens such as phytophtora |
| oxalate oxidase | bacterial and fungal pathogens such as Phytophtora, Verticillium, Rhizoctonia |
| glucose oxidase | bacterial and fungal pathogens such as Phytophtora, Verticillium, Rhizoctonia |
| pyrrolnitrin synthesis genes | bacterial and fungal pathogens such as Phytophtora, Verticillium, Rhizoctonia |
| serine/threonine kinases | bacterial and fungal pathogens such as Phytophtora, Venicillium, Rhizoctonia |
| Cecropin B | bacteria such as corynebacterium sepedonicum, Erwinia carotovora |
| Phenylalanine ammonia lyase (PAL) | bacterial and fungal pathogens such as Phytophtora, Verticillium, Rhizoctonia |
| phytoalexins | bacterial and fungal pathogens such as Phytophtora, Verticillium, Rhizoctonia |
| B-1,3-glucanase antisense | bacterial and fungal pathogens such as Phytophtora, Verticillium, Rhizoctonia |
| receptor kinase | bacterial and fungal pathogens such as Phytophtora, Verticillium, Rhizoctonia |
| Hypersensitive response eliciting polypeptide | bacterial and fungal pathogens such as Phytophtora, Verticillium, Rhizoctonia |
| Systemic acquires resistance (SAR) genes | viral, bacterial, fungal, nematodal pathogens |
| Chitinases | bacterial and fungal pathogens such as Phytophtora, Verticillium, Rhizoctonia |
| Barnase | bacterial and fungal pathogens such as Phytophtora, Verticillium, Rhizoctonia |
| Disease resistance response gene 49 | bacterial and fungal pathogens such as Phytophtora, Verticillium, Rhizoctonia |
| trans aldolase antisense | blackspots |
| Glucanases | bacterial and fungal pathogens such as Phytophtora, Verticillium, Rhizoctonia |
| double stranded ribonuclease | viruses such as PLRV, PVY and TRV |
| Coat proteins | viruses such as PLRV, PVY and TRV |
| 17 kDa or 60 kDa protein | viruses such as PLRV, PVY and TRV |
| Nuclear inclusion proteins eg. a or b | viruses such as PLRV, PVY and TRV |
| Pseudoubiquitin | viruses such as PLRV, PVY and TRV |
| Replicase | viruses such as PLRV, PVY and TRV |
| *Bacillus thuringiensis* toxins, VIP 3, *Bacillus cereus* toxins, Photorabdus and Xenorhabdus toxins | coleoptera eg colorado potato bettle, aphids |
| 3-Hydroxysteroid oxidase | coleoptera eg colorado potato beetle, aphids |
| Peroxidase | coleoptera eg colorado potato beetle, aphids |

TABLE A6-continued

Crop Potatoes

| Effected target or expressed principle(s) | Crop phenotype/Tolerance to |
|---|---|
| Aminopeptidase inhibitors eg. Leucine aminopeptidase inhibitor | coleoptera eg colorado potato beetle, aphids |
| stilbene synthase | coleoptera eg colorado potato beetle, aphids |
| Lectines | coleoptera eg colorado potato beetle, aphids |
| Protease inhibitors eg cystatin, patatin | coleoptera eg colorado potato beetle, aphids |
| ribosome inactivating protein | coleoptera eg colorado potato beetle, aphids |
| HMG-CoA reductase | coleoptera eg colorado potato beetle, aphids |
| Cyst nematode hatching stimulus | cyst nematodes |
| Barnase | nematodes eg root knot nematodes and cyst nematodes |
| Antifeeding principles | nematodes eg root knot nematodes and cyst nematodes |

TABLE A7

Crop Tomatoes

| Effected target or expressed principle(s) | Crop phenotype/Tolerance to |
|---|---|
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkane-carboxylic acids, cyclohexanediones |
| Hydroxyphenylpyruvate dioxygenase (HPPD) | Isoxazoles such as Isoxaflutol or Isoxachiortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzo-nitriles such as Bromoxynil and Ioxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |
| Polyphenol oxidase or Polyphenol oxidase antisense | blackspot bruise |
| Metallothionein | bacterial and fungal pathogens such as phytophtora |
| Ribonuclease | Phytophtora, Verticillium, Rhizoctonia |
| Antifungal polypeptide AlyAFP | bacterial and fungal pathogens such as bacterial speck, fusarium, soft rot, powdery mildew, crown rot, leaf mould etc. |
| oxalate oxidase | bacterial and fungal pathogens such as bacterial speck, fusarium, soft rot, powdery mildew, crown rot, leaf mould etc. |

TABLE A7-continued

Crop Tomatoes

| Effected target or expressed principle(s) | Crop phenotype/Tolerance to |
|---|---|
| glucose oxidase | bacterial and fungal pathogens such as bacterial speck, fusarium, soft rot, powdery mildew, crown rot, leaf mould etc. |
| pyrrolnitrin synthesis genes | bacterial and fungal pathogens such as bacterial speck, fusarium, soft rot, powdery mildew, crown rot, leaf mould etc. |
| serine/threonine kinases | bacterial and fungal pathogens such as bacterial speck, fusarium, soft rot, powdery mildew, crown rot, leaf mould etc. |
| Cecropin B | bacterial and fungal pathogens such as bacterial speck, fusarium, soft rot, powdery mildew, crown rot, leaf mould etc. |
| Phenylalanine ammonia lyase (PAL) | bacterial and fungal pathogens such as bacterial speck, fusarium, soft rot, powdery mildew, crown rot, leaf mould etc. |
| Cf genes eg. Cf 9 Cf5 Cf4 Cf2 | leaf mould |
| Osmotin | alternaria solani |
| Alpha Hordothionin | bacteria |
| Systemin | bacterial and fungal pathogens such as bacterial speck, fusarium, soft rot, powdery mildew, crown rot, leaf mould etc. |
| Polygalacturonase inhibitors | bacterial and fungal pathogens such as bacterial speck, fusarium, soft rot, powdery mildew, crown rot, leaf mould etc. |
| Prf regulatory gene | bacterial and fungal pathogens such as bacterial speck, fusarium, soft rot, powdery mildew, crown rot, leaf mould etc. |
| I2 Fusarium resistance locus | fusarium |
| phytoalexins | bacterial and fungal pathogens such as bacterial speck, fusarium, soft rot, powdery mildew, crown rot, leaf mould etc. |
| B-1,3-glucanase antisense | bacterial and fungal pathogens such as bacterial speck, fusarium, soft rot, powdery mildew, crown rot, leaf mould etc. |
| receptor kinase | bacterial and fungal pathogens such as bacterial speck, fusarium, soft rot, powdery mildew, crown rot, leaf mould etc. |
| Hypersensitive response eliciting polypeptide | bacterial and fungal pathogens such as bacterial speck, fusarium, soft rot, powdery mildew, crown rot, leaf mould etc. |
| Systemic acquires resistance (SAR) genes | viral, bacterial, fungal, nematodal pathogens |
| Chitinases | bacterial and fungal pathogens such as bacterial speck, fusarium, soft rot, powdery mildew, crown rot, leaf mould etc. |

TABLE A7-continued

Crop Tomatoes

| Effected target or expressed principle(s) | Crop phenotype/Tolerance to |
| --- | --- |
| Barnase | bacterial and fungal pathogens such as bacterial speck, fusarium, soft rot, powdery mildew, crown rot, leaf mould etc. |
| Glucanases | bacterial and fungal pathogens such as bacterial speck, fusarium, soft rot, powdery mildew, crown rot, leaf mould etc. |
| double stranded ribonuclease | viruses such as PLRV, PVY and ToMoV |
| Coat proteins | viruses such as PLRV, PVY and ToMoV |
| 17 kDa or 60 kDa protein | viruses such as PLRV, PVY and ToMoV |
| Nuclear inclusion proteins eg. a or b or | viruses such as PLRV, PVY and ToMoV |
| Nucleoprotein | TRV |
| Pseudoubiquitin | viruses such as PLRV, PVY and ToMoV |
| Replicase | viruses such as PLRV, PVY and ToMoV |
| *Bacillus thuringiensis* toxins, VIP 3, *Bacillus cereus* toxins, Photorabdus and Xenorhabdus toxins | lepidoptera eg heliothis, whiteflies aphids |
| 3-Hydroxysteroid oxidase | lepidoptera eg heliothis, whiteflies aphids |
| Peroxidase | lepidoptera eg heliothis, whiteflies aphids |
| Aminopeptidase inhibitors eg. Leucine aminopeptidase inhibitor | lepidoptera eg heliothis, whiteflies aphids |
| Lectines | lepidoptera eg heliothis, whiteflies aphids |
| Protease Inhibitors eg cystatin, patatin | lepidoptera eg heliothis, whiteflies aphids |
| ribosome inactivating protein | lepidoptera eg heliothis, whiteflies aphids |
| stilbene synthase | lepidoptera eg heliothis, whiteflies aphids |
| HMG-CoA reductase | lepidoptera eg heliothis, whiteflies aphids |
| Cyst nematode hatching stimulus | cyst nematodes |
| Barnase | nematodes eg root knot nematodes and cyst nematodes |
| Antifeeding principles | nematodes eg root knot nematodes and cyst nematodes |

TABLE A8

Crop Peppers

| Effected target or expressed principle(s) | Crop phenotype/Tolerance to |
| --- | --- |
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkane-carboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |

TABLE A8-continued

Crop Peppers

| Effected target or expressed principle(s) | Crop phenotype/Tolerance to |
| --- | --- |
| Anthranilate Synthase | Inhibitors of tryptophan synthesis and catabolism |
| Nitrilase | 3,5-dihalo-4-hydroxy-benzo-nitriles such as Bromoxynil and Ioxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |
| Polyphenol oxidase or Polyphenol oxidase antisense | bacterial and fungal pathogens |
| Metallothionein | bacterial and fungal pathogens |
| Ribonuclease | bacterial and fungal pathogens |
| Antifungal polypeptide AlyAFP | bacterial and fungal pathogens |
| oxalate oxidase | bacterial and fungal pathogens |
| glucose oxidase | bacterial and fungal pathogens |
| pyrrolnitrin synthesis genes | bacterial and fungal pathogens |
| serine/threonine kinases | bacterial and fungal pathogens |
| Cecropin B | bacterial and fungal pathogens rot, leaf mould etc. |
| Phenylalanine ammonia lyase (PAL) | bacterial and fungal pathogens |
| Cf genes eg. Cf 9 Cf5 Cf4 Cf2 | bacterial and fungal pathogens |
| Osmotin | bacterial and fungal pathogens |
| Alpha Hordothionin | bacterial and fungal pathogens |
| Systemin | bacterial and fungal pathogens |
| Polygalacturonase inhibitors | bacterial and fungal pathogens |
| Prf regulatory gene | bacterial and fungal pathogens |
| I2 Fusarium resistance locus | fusarium |
| phytoalexins | bacterial and fungal pathogens |
| B-1,3-glucanase antisense | bacterial and fungal pathogens |
| receptor kinase | bacterial and fungal pathogens |
| Hypersensitive response eliciting polypeptide | bacterial and fungal pathogens |
| Systemic acquires resistance (SAR) genes | viral, bacterial, fungal, nematodal pathogens |
| Chitinases | bacterial and fungal pathogens |
| Barnase | bacterial and fungal pathogens |
| Glucanases | bacterial and fungal pathogens |
| double stranded ribonuclease | viruses such as CMV, TEV |
| Coat proteins | viruses such as CMV, TEV |
| 17 kDa or 60 kDa protein | viruses such as CMV, TEV |
| Nuclear inclusion proteins eg. a or b or Nucleoprotein | viruses such as CMV, TEV |
| Pseudoubiquitin | viruses such as CMV, TEV |
| Replicase | viruses such as CMV, TEV |
| *Bacillus thuringiensis* toxins, VIP 3, *Bacillus cereus* toxins, Photorabdus and Xenorhabdus toxins | lepidoptera, whiteflies aphids |
| 3-Hydroxysteroid oxidase | lepidoptera, whiteflies aphids |
| Peroxidase | lepidoptera, whiteflies aphids |
| Aminopeptidase inhibitors eg. Leucine aminopeptidase inhibitor | lepidoptera, whiteflies aphids |
| Lectines | lepidoptera, whiteflies aphids |
| Protease inhibitors eg cystatin, patatin | lepidoptera, whiteflies aphids |
| ribosome inactivating protein | lepidoptera, whiteflies aphids |
| stilbene synthase | lepidoptera, whiteflies aphids |
| HMG-CoA reductase | lepidoptera, whiteflies aphids |
| Cyst nematode hatching stimulus | cyst nematodes |
| Barnase | nematodes eg root knot nematodes and cyst nematodes |
| Antifeeding principles | nematodes eg root knot nematodes and cyst nematodes |

TABLE A9

Crop Grapes

| Effected target or expressed principle(s) | Crop phenotype/Tolerance to |
|---|---|
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkane-carboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzo-nitriles such as Bromoxynil and Ioxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |
| Polyphenol oxidase or Polyphenol oxidase antisense | bacterial and fungal pathogens like Botrytis and powdery mildew |
| Metallothionein | bacterial and fungal pathogens like Botrytis and powdery mildew |
| Ribonuclease | bacterial and fungal pathogens like Botrytis and powdery mildew |
| Antifungal polypeptide AlyAFP | bacterial and fungal pathogens like Botrytis and powdery mildew |
| oxalate oxidase | bacterial and fungal pathogens like Botrytis and powdery mildew |
| glucose oxidase | bacterial and fungal pathogens like Botrytis and powdery mildew |
| pyrrolnitrin synthesis genes | bacterial and fungal pathogens like Botrytis and powdery mildew |
| serine/threonine kinases | bacterial and fungal pathogens like Botrytis and powdery mildew |
| Cecropin B | bacterial and fungal pathogens like Botrytis and powdery mildew |
| Phenylalanine ammonia lyase (PAL) | bacterial and fungal pathogens like Botrytis and powdery mildew |
| Cf genes eg. Cf 9 Cf5 Cf4 Cf2 | bacterial and fungal pathogens like Botrytis and powdery mildew |
| Osmotin | bacterial and fungal pathogens like Botrytis and powdery mildew |
| Alpha Hordothionin | bacterial and fungal pathogens like Botrytis and powdery mildew |
| Systemin | bacterial and fungal pathogens like Botrytis and powdery mildew |
| Polygalacturonase inhibitors | bacterial and fungal pathogens like Botrytis and powdery mildew |
| Prf regulatory gene | bacterial and fungal pathogens like Botrytis and powdery mildew |
| phytoalexins | bacterial and fungal pathogens like Botrytis and powdery mildew |
| B-1,3-glucanase antisense | bacterial and fungal pathogens like Botrytis and powdery mildew |
| receptor kinase | bacterial and fungal pathogens like Botrytis and powdery mildew |
| Hypersensitive response eliciting polypeptide | bacterial and fungal pathogens like Botrytis and powdery mildew |
| Systemic acquires resistance (SAR) genes | viral, bacterial, fungal, nematodal pathogens |
| Chitinases | bacterial and fungal pathogens like Botrytis and powdery mildew |
| Barnase | bacterial and fungal pathogens like Botrytis and powdery mildew |
| Glucanases | bacterial and fungal pathogens like Botrytis and powdery mildew |
| double stranded ribonuclease | viruses |
| Coat proteins | viruses |
| 17 kDa or 60 kDa protein | viruses |
| Nuclear inclusion proteins eg a or b or Nucleoprotein | viruses |
| Pseudoubiquitin | viruses |
| Replicase | viruses |
| *Bacillus thuringiensis* toxins, VIP 3, *Bacillus cereus* toxins, Photorabdus and Xenorhabdus toxins | lepidoptera, aphids |
| 3-Hydroxysteroid oxidase | lepidoptera, aphids |
| Peroxidase | lepidoptera, aphids |
| Aminopeptidase inhibitors eg. Leucine aminopeptidase inhibitor | lepidoptera, aphids |
| Lectines | lepidoptera, aphids |
| Protease Inhibitors eg cystatin, patatin | lepidoptera, aphids |
| ribosome inactivating protein | lepidoptera, aphids |
| stilbene synthase | lepidoptera, aphids, diseases |
| HMG-CoA reductase | lepidoptera, aphids |
| Cyst nematode hatching stimulus | cyst nematodes |
| Barnase | nematodes eg root knot nematodes and cyst nematodes or general diseases |
| CBI | root knot nematodes |
| Antifeeding principles | nematodes eg root knot nematodes or root cyst nematodes |

TABLE A10 crop Oil Seed rape

| Effected target or expressed principle(s) | Crop phenotype/Tolerance to |
|---|---|
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkane-carboxylic acids, cyclo-hexanediones |
| Hydroxyphenylpyruvate dioxygenase (HPPD) | Isoxazoles such as Isoxaflutol or Isoxachlortol, Triones such as mesotrione or sulcotrione |

TABLE A10-continued crop Oil Seed rape

| Effected target or expressed principle(s) | Crop phenotype/Tolerance to |
|---|---|
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzo-nitriles such as Bromoxynil and Ioxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |
| Polyphenol oxidase or Polyphenol oxidase antisense | bacterial and fungal pathogens like Cylindrosporium, Phoma, Sclerotinia |
| Metallothionein | bacterial and fungal pathogens like Cylindrosporium, Phoma, Sclerotinia |
| Ribonuclease | bacterial and fungal pathogens like Cylindrosporium, Phoma, Sclerotinia |
| Antifungal polypeptide AlyAFP | bacterial and fungal pathogens like Cylindrosporium, Phoma, Sclerotinia |
| oxalate oxidase | bacterial and fungal pathogens like Cylindrosporium, Phoma, Sclerotinia |
| glucose oxidase | bacterial and fungal pathogens like Cylindrosporium, Phoma, Sclerotinia |
| pyrrolnitrin synthesis genes | bacterial and fungal pathogens like Cylindrosporium, Phoma, Sclerotinia |
| serine/threonine kinases | bacterial and fungal pathogens like Cylindrosporium, Phoma, Sclerotinia |
| Cecropin B | bacterial and fungal pathogens like Cylindrosporium, Phoma, Sclerotinia |
| Phenylalanine ammonia lyase (PAL) | bacterial and fungal pathogens like Cylindrosporium, Phoma, Sclerotinia |
| Cf genes eg. Cf 9 Cf5 Cf4 Cf2 | bacterial and fungal pathogens like Cylindrosporium, Phoma, Sclerotinia |
| Osmotin | bacterial and fungal pathogens like Cylindrosporium, Phoma, Sclerotinia |
| Alpha Hordothionin | bacterial and fungal pathogens like Cylindrosporium, Phoma, Sclerotinia |
| Systemin | bacterial and fungal pathogens like Cylindrosporium, Phoma, Sclerotinia |
| Polygalacturonase inhibitors | bacterial and fungal pathogens like Cylindrosporium, Phoma, Sclerotinia |
| Prf regulatory gene | bacterial and fungal pathogens like Cylindrosporium, Phoma, Sclerotinia |
| phytoalexins | bacterial and fungal pathogens like Cylindrosporium, Phoma, Sclerotinia |
| B-1,3-glucanase antisense | bacterial and fungal pathogens like Cylindrosporium, Phoma, Sclerotinia |

TABLE A10-continued crop Oil Seed rape

| Effected target or expressed principle(s) | Crop phenotype/Tolerance to |
|---|---|
| receptor kinase | bacterial and fungal pathogens like Cylindrosporium, Phoma, Sclerotinia |
| Hypersensitive response eliciting polypeptide | bacterial and fungal pathogens like Cylindrosporium, Phoma, Sclerotinia |
| Systemic acquires resistance (SAR) genes | viral, bacterial, fungal, nematodal pathogens |
| Chitinases | bacterial and fungal pathogens like Cylindrosporium, Phoma, Sclerotinia |
| Barnase | bacterial and fungal pathogens like Cylindrosporium, Phoma, Sclerotinia, nematodes |
| Glucanases | bacterial and fungal pathogens like Cylindrosporium, Phoma, Sclerotinia |
| double stranded ribonuclease | viruses |
| Coat proteins | viruses |
| 17 kDa or 60 kDa protein | viruses |
| Nuclear inclusion proteins eg. a or b or Nucleoprotein | viruses |
| Pseudoubiquitin | viruses |
| Replicase | viruses |
| Bacillus thuringiensis toxins, VIP 3, Bacilius cereus toxins, Photorabdus and Xenorhabdus toxins | lepidoptera, aphids |
| 3-Hydroxysteroid oxidase | lepidoptera, aphids |
| Peroxidase | lepidoptera, aphids |
| Aminopeptidase inhibitors eg. Leucine aminopeptidase inhibitor | lepidoptera, aphids |
| Lectines | lepidoptera, aphids |
| Protease inhibitors eg cystatin, patatin, CPTI | lepidoptera, aphids |
| ribosome inactivating protein | lepidoptera, aphids |
| stilbene synthase | lepidoptera, aphids, diseases |
| HMG-CoA reductase | lepidoptera, aphids |
| Cyst nematode hatching stimulus | cyst nematodes |
| Barnase | nematodes eg root knot nematodes and cyst nematodes |
| CBI | root knot nematodes |
| Antifeeding principles induced at a nematode feeding site | nematodes eg root knot nematodes, root cyst nematodes |

TABLE A11

Crop Brassica vegetable (cabbage, brussel sprouts, broccoli etc.)

| Effected target or expressed principle(s) | Crop phenotype/Tolerance to |
|---|---|
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkane-carboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzo-nitriles such as Bromoxynil and Ioxinyl |

TABLE A11-continued

Crop Brassica vegetable (cabbage, brussel sprouts, broccoli etc.)

| Effected target or expressed principle(s) | Crop phenotype/Tolerance to |
|---|---|
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |
| Polyphenol oxidase or Polyphenol oxidase antisense | bacterial and fungal pathogens |
| Metallothionein | bacterial and fungal pathogens |
| Ribonuclease | bacterial and fungal pathogens |
| Antifungal polypeptide AlyAFP | bacterial and fungal pathogens |
| oxalate oxidase | bacterial and fungal pathogens |
| glucose oxidase | bacterial and fungal pathogens |
| pyrrolnitrin synthesis genes | bacterial and fungal pathogens |
| serine/threonine kinases | bacterial and fungal pathogens |
| Cecropin B | bacterial and fungal pathogens |
| Phenylalanine ammonia lyase (PAL) | bacterial and fungal pathogens |
| Cf genes eg. Cf 9 Cf5 Cf4 Cf2 | bacterial and fungal pathogens |
| Osmotin | bacterial and fungal pathogens |
| Alpha Hordothionin | bacterial and fungal pathogens |
| Systemin | bacterial and fungal pathogens |
| Polygalacturonase inhibitors | bacterial and fungal pathogens |
| Prf regulatory gene | bacterial and fungal pathogens |
| phytoalexins | bacterial and fungal pathogens |
| B-1,3-glucanase antisense | bacterial and fungal pathogens |
| receptor kinase | bacterial and fungal pathogens |
| Hypersensitive response eliciting polypeptide | bacterial and fungal pathogens |
| Systemic acquires resistance (SAR) genes | viral, bacterial, fungal, nematodal pathogens |
| Chitinases | bacterial and fungal pathogens |
| Barnase | bacterial and fungal pathogens |
| Glucanases | bacterial and fungal pathogens |
| double stranded ribonuclease | viruses |
| Coat proteins | viruses |
| 17 kDa or 60 kDa protein | viruses |
| Nuclear inclusion proteins eg. a or b or Nucleoprotein | viruses |
| Pseudoubiquitin | viruses |
| Replicase | viruses |
| Bacillus thuringiensis toxins, VIP 3, Bacillus cereus toxins, Photorabdus and Xenorhabdus toxins | lepidoptera, aphids |
| 3-Hydroxysteroid oxidase | lepidoptera, aphids |
| Peroxidase | lepidoptera, aphids |
| Aminopeptidase inhibitors eg. Leucine aminopeptidase inhibitor | lepidoptera, aphids |
| Lectines | lepidoptera, aphids |
| Protease inhibitors eg cystatin, patatin, CPTI | lepidoptera, aphids |
| ribosome inactivating protein | lepidoptera, aphids |
| stilbene synthase | lepidoptera, aphids, diseases |
| HMG-CoA reductase | lepidoptera, aphids |
| Cyst nematode hatching stimulus | cyst nematodes |
| Barnase | nematodes eg root knot nematodes and cyst nematodes |
| CBI | root knot nematodes |
| Antifeeding pnnciples induced at a nematode feeding site | nematodes eg root knot nematodes, root cyst nematodes |

TABLE A12

Crop Pome fruits eg apples, pears

| Effected target or expressed principle(s) | Crop phenotype/Tolerance to |
|---|---|
| Acetolactate synthase (ALS) | Sulfonylureas, Imidazolinones, Triazolopyrimidines, Pyrimidyloxybenzoates, Phtalides |

TABLE A12-continued

Crop Pome fruits eg apples, pears

| Effected target or expressed principle(s) | Crop phenotype/Tolerance to |
|---|---|
| AcetylCoA Carboxylase (ACCase) | Aryloxyphenoxyalkane-carboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzo-nitriles such as Bromoxynil and Ioxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |
| Polyphenol oxidase or Polyphenol oxidase antisense | bacterial and fungal pathogens like apple scab or fireblight |
| Metallothionein | bacterial and fungal pathogens like apple scab or fireblight |
| Ribonuclease | bacterial and fungal pathogens like apple scab or fireblight |
| Antifungal polypeptide AlyAFP | bacterial and fungal pathogens like apple scab or fireblight |
| oxalate oxidase | bacterial and fungal pathogens like apple scab or fireblight |
| glucose oxidase | bacterial and fungal pathogens like apple scab or fireblight |
| pyrrolnitrin synthesis genes | bacterial and fungal pathogens like apple scab or fireblight |
| serine/threonine kinases | bacterial and fungal pathogens like apple scab or fireblight |
| Cecropin B | bacterial and fungal pathogens like apple scab or fireblight |
| Phenylalanine ammonia lyase (PAL) | bacterial and fungal pathogens like apple scab or fireblight |
| Cf genes eg. Cf 9 Cf5 Cf4 Cf2 | bacterial and fungal pathogens like apple scab or fireblight |
| Osmotin | bacterial and fungal pathogens like apple scab or fireblight |
| Alpha Hordothionin | bacterial and fungal pathogens like apple scab or fireblight |
| Systemin | bacterial and fungal pathogens like apple scab or fireblight |
| Polygalacturonase inhibitors | bacterial and fungal pathogens like apple scab or fireblight |
| Prf regulatory gene | bacterial and fungal pathogens like apple scab or fireblight |
| phytoalexins | bacterial and fungal pathogens like apple scab or fireblight |
| B-1,3-glucanase antisense | bacterial and fungal pathogens like apple scab or fireblight |
| receptor kinase | bacterial and fungal pathogens like apple scab or fireblight |
| Hypersensitive response eliciting polypeptide | bacterial and fungal pathogens like apple scab or fireblight |
| Systemic acquires resistance (SAR) genes | viral, bacterial, fungal, nematodal pathogens |
| Lytic protein | bacterial and fungal pathogens like apple scab or fireblight |
| Lysozym | bacterial and fungal pathogens like apple scab or fireblight |

TABLE A12-continued

Crop Pome fruits eg apples, pears

| Effected target or expressed principle(s) | Crop phenotype/Tolerance to |
|---|---|
| Chitinases | bacterial and fungal pathogens like apple scab or fireblight |
| Barnase | bacterial and fungal pathogens like apple scab or fireblight |
| Glucanases | bacterial and fungal pathogens like apple scab or fireblight |
| double stranded ribonuclease | viruses |
| Coat proteins | viruses |
| 17 kDa or 60 kDa protein | viruses |
| Nuclear inclusion proteins eg. a or b or Nucleoprotein | viruses |
| Pseudoubiquitin | viruses |
| Replicase | viruses |
| *Bacillus thuringiensis* toxins, VIP 3, *Bacillus cereus* toxins, Photorabdus and Xenorhabdus toxins | lepidoptera, aphids, mites |
| 3-Hydroxysteroid oxidase | lepidoptera, aphids, mites |
| Peroxidase | lepidoptera, aphids, mites |
| Aminopeptidase inhibitors eg. Leucine aminopeptidase inhibitor | lepidoptera, aphids, mites |
| Lectines | lepidoptera, aphids, mites |
| Protease inhibitors eg cystatin, patatin, CPTI | lepidoptera, aphids, mites |
| ribosome inactivating protein | lepidoptera, aphids, mites |
| stilbene synthase | lepidoptera, aphids, diseases, mites |
| HMG-COA reductase | lepidoptera, aphids, mites |
| Cyst nematode hatching stimulus | cyst nematodes |
| Barnase | nematodes eg root knot nematodes and cyst nematodes |
| CBI | root knot nematodes |
| Antifeeding principles induced at a nematode feeding site | nematodes eg root knot nematodes, root cyst nematodes |

TABLE A13

Crop Melons

| Effected target or expressed principle(s) | Crop phenotype/Tolerance to |
|---|---|
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkane-carboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzo-nitriles such as Bromoxynil and Ioxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |

TABLE A13-continued

Crop Melons

| Effected target or expressed principle(s) | Crop phenotype/Tolerance to |
|---|---|
| Polyphenol oxidase or Polyphenol oxidase antisense | bacterial or fungal pathogens like phytophtora |
| Metallothionein | bacterial or fungal pathogens like phytophtora |
| Ribonuclease | bacterial or fungal pathogens like phytophtora |
| Antifungal polypeptide AlyAFP | bacterial or fungal pathogens like phytophtora |
| oxalate oxidase | bacterial or fungal pathogens like phytophtora |
| glucose oxidase | bacterial or fungal pathogens like phytophtora |
| pyrrolnitrin synthesis genes | bacterial or fungal pathogens like phytophtora |
| serine/threonine kinases | bacterial or fungal pathogens like phytophtora |
| Cecropin B | bacterial or fungal pathogens like phytophtora |
| Phenylalanine ammonia lyase (PAL) | bacterial or fungal pathogens like phytophtora |
| Cf genes eg. Cf 9 Cf5 Cf4 Cf2 | bacterial or fungal pathogens like phytophtora |
| Osmotin | bacterial or fungal pathogens like phytophtora |
| Alpha Hordothionin | bacterial or fungal pathogens like phytophtora |
| Systemin | bacterial or fungal pathogens like phytophtora |
| Polygalacturonase inhibitors | bacterial or fungal pathogens like phytophtora |
| Prf regulatory gene | bacterial or fungal pathogens like phytophtora |
| phytoalexins | bacterial or fungal pathogens like phytophtora |
| B-1,3-glucanase antisense | bacterial or fungal pathogens like phytophtora |
| receptor kinase | bacterial or fungal pathogens like phytophtora |
| Hypersensitive response eliciting polypeptide | bacterial or fungal pathogens like phytophtora |
| Systemic acquires resistance (SAR) genes | viral, bacterial, fungal, nematodal pathogens |
| Lytic protein | bacterial or fungal pathogens like phytophtora |
| Lysozym | bacterial or fungal pathogens like phytophtora |
| Chitinases | bacterial or fungal pathogens like phytophtora |
| Barnase | bacterial or fungal pathogens like phytophtora |
| Glucanases | bacterial or fungal pathogens like phytophtora |
| double stranded ribonuclease | viruses as CMV,, PRSV, WMV2, SMV, ZYMV |
| Coat proteins | viruses as CMV,, PRSV, WMV2, SMV, ZYMV |
| 17 kDa or 60 kDa protein | viruses as CMV,, PRSV, WMV2, SMV, ZYMV |
| Nuclear inclusion proteins eg. a or b or Nucleoprotein | viruses as CMV,, PRSV, WMV2, SMV, ZYMV |
| Pseudoubiquitin | viruses as CMV,, PRSV, WMV2, SMV, ZYMV |
| Replicase | viruses as CMV,, PRSV, WMV2, SMV, ZYMV |
| *Bacillus thuringiensis* toxins, VIP 3, *Bacillus cereus* toxins, Photorabdus and Xenorhabdus toxins | lepidoptera, aphids, mites |
| 3-Hydroxysteroid oxidase | lepidoptera, aphids, mites, whitefly |
| Peroxidase | lepidoptera, aphids, mites, whitefly |
| Aminopeptidase inhibitors eg. Leucine aminopeptidase inhibitor | lepidoptera, aphids, mites, whitefly |
| Lectines | lepidoptera, aphids, mites, whitefly |

TABLE A13-continued

Crop Melons

| Effected target or expressed principle(s) | Crop phenotype/Tolerance to |
|---|---|
| Protease inhibitors eg cystatin, patatin, CPTI, virgiferin | lepidoptera, aphids, mites, whitefly |
| ribosome inactivating protein | lepidoptera, aphids, mites, whitefly |
| stilbene synthase | lepidoptera, aphids, mites, whitefly |
| HMG-CoA reductase | lepidoptera, aphids, mites, whitefly |
| Cyst nematode hatching stimulus | cyst nematodes |
| Barnase | nematodes eg root knot nematodes and cyst nematodes |
| CBI | root knot nematodes |
| Antifeeding principles induced at a nematode feeding site | nematodes eg root knot nematodes, root cyst nematodes |

TABLE A14

Crop Banana

| Effected target or expressed principle(s) | Crop phenotype/Tolerance to |
|---|---|
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzonitriles such as Bromoxynil and Ioxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |
| Polyphenol oxidase or Polyphenol oxidase antisense | bacterial or fungal pathogens |
| Metallothionein | bacterial or fungal pathogens |
| Ribonuclease | bacterial or fungal pathogens |
| Antifungal polypeptide AlyAFP | bacterial or fungal pathogens |
| oxalate oxidase | bacterial or fungal pathogens |
| glucose oxidase | bacterial or fungal pathogens |
| pyrrolnitrin synthesis genes | bacterial or fungal pathogens |
| serine/threonine kinases | bacterial or fungal pathogens |
| Cecropin B | bacterial or fungal pathogens |
| Phenylalanine ammonia lyase (PAL) | bacterial or fungal pathogens |
| Cf genes eg. Cf 9 Cf5 Cf4 Cf2 | bacterial or fungal pathogens |
| Osmotin | bacterial or fungal pathogens |
| Alpha Hordothionin | bacterial or fungal pathogens |
| Systemin | bacterial or fungal pathogens |
| Polygalacturonase inhibitors | bacterial or fungal pathogens |
| Prf regulatory gene | bacterial or fungal pathogens |
| phytoalexins | bacterial or fungal pathogens |
| B-1,3-glucanase antisense | bacterial or fungal pathogens |
| receptor kinase | bacterial or fungal pathogens |
| Hypersensitive response eliciting polypeptide | bacterial or fungal pathogens |

TABLE A14-continued

Crop Banana

| Effected target or expressed principle(s) | Crop phenotype/Tolerance to |
|---|---|
| Systemic acquires resistance (SAR) genes | viral, bacterial, fungal, nematodal pathogens |
| Lytic protein | bacterial or fungal pathogens |
| Lysozym | bacterial or fungal pathogens |
| Chitinases | bacterial or fungal pathogens |
| Barnase | bacterial or fungal pathogens |
| Glucanases | bacterial or fungal pathogens |
| double stranded ribonuclease | viruses as Banana bunchy top virus (BBTV) |
| Coat proteins | viruses as Banana bunchy top virus (BBTV) |
| 17 kDa or 60 kDa protein | viruses as Banana bunchy top virus (BBTV) |
| Nuclear inclusion proteins eg. a or b or Nucleoprotein | viruses as Banana bunchy top virus (BBTV) |
| Pseudoubiquitin | viruses as Banana bunchy top virus (BBTV) |
| Replicase | viruses as Banana bunchy top virus (BBTV) |
| Bacillus thuringiensis toxins, VIP 3, Bacillus cereus toxins, Photorabdus and Xenorhabdus toxins | lepidoptera, aphids, mites, nematodes |
| 3-Hydroxysteroid oxidase | lepidoptera, aphids, mites, nematodes |
| Peroxidase | lepidoptera, aphids, mites, nematodes |
| Aminopeptidase inhibitors eg. Leucine aminopeptidase inhibitor | lepidoptera, aphids, mites, nematodes |
| Lectines | lepidoptera, aphids, mites, nematodes |
| Protease Inhibitors eg cystatin, patatin, CPTI, virgiferin | lepidoptera, aphids, mites, nematodes |
| ribosome inactivating protein | lepidoptera, aphids, mites, nematodes |
| stilbene synthase | lepidoptera, aphids, mites, nematodes |
| HMG-CoA reductase | lepidoptera, aphids, mites, nematodes |
| Cyst nematode hatching stimulus | cyst nematodes |
| Barnase | nematodes eg root knot nematodes and cyst nematodes |
| CBI | root knot nematodes |
| Antifeeding principles induced at a nematode feeding site | nematodes eg root knot nematodes, root cyst nematodes |

TABLE A15

Crop Cotton

| Effected target or expressed principle(s) | Crop phenotype/Tolerance to |
|---|---|
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |

TABLE A15-continued

Crop Cotton

| Effected target or expressed principle(s) | Crop phenotype/Tolerance to |
|---|---|
| Nitrilase | 3,5-dihalo-4-hydroxy-benzonitriles such as Bromoxynil and Ioxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |
| Polyphenol oxidase or Polyphenol oxidase antisense | bacterial or fungal pathogens |
| Metallothionein | bacterial or fungal pathogens |
| Ribonuclease | bacterial or fungal pathogens |
| Antifungal polypeptide AlyAFP | bacterial or fungal pathogens |
| oxalate oxidase | bacterial or fungal pathogens |
| glucose oxidase | bacterial or fungal pathogens |
| pyrrolnitrin synthesis genes | bacterial or fungal pathogens |
| serine/threonine kinases | bacterial or fungal pathogens |
| Cecropin B | bacterial or fungal pathogens |
| Phenylalanine ammonia lyase (PAL) | bacterial or fungal pathogens |
| Cf genes eg. Cf 9 Cf5 Cf4 Cf2 | bacterial or fungal pathogens |
| Osmotin | bacterial or fungal pathogens |
| Alpha Hordothionin | bacterial or fungal pathogens |
| Systemin | bacterial or fungal pathogens |
| Polygalacturonase inhibitors | bacterial or fungal pathogens |
| Prf regulatory gene | bacterial or fungal pathogens |
| phytoalexins | bacterial or fungal pathogens |
| B-1,3-glucanase antisense | bacterial or fungal pathogens |
| receptor kinase | bacterial or fungal pathogens |
| Hypersensitive response eliciting polypeptide | bacterial or fungal pathogens |
| Systemic acquires resistance (SAR) genes | viral, bacterial, fungal, nematodal pathogens |
| Lytic protein | bacterial or fungal pathogens |
| Lysozym | bacterial or fungal pathogens |
| Chitinases | bacterial or fungal pathogens |
| Barnase | bacterial or fungal pathogens |
| Glucanases | bacterial or fungal pathogens |
| double stranded ribonuclease | viruses as wound tumor virus (WTV) |
| Coat proteins | viruses as wound tumor virus (WTV) |
| 17 kDa or 60 kDa protein | viruses as wound tumor virus (WTV) |
| Nuclear inclusion proteins eg. a or b or Nucleoprotein | viruses as wound tumor virus (WTV) |
| Pseudoubiquitin | viruses as wound tumor virus (WTV) |
| Replicase | viruses as wound tumor virus (WTV) |
| Bacillus thuringiensis toxins, VIP 3, Bacillus cereus toxins, Photorabdus and Xenorhabdus toxins | lepidoptera, aphids, mites, nematodes, whitefly |
| 3-Hydroxysteroid oxidase | lepidoptera, aphids, mites, nematodes, whitefly |
| Peroxidase | lepidoptera, aphids, mites, nematodes, whitefly |
| Aminopeptidase inhibitors eg. Leucine aminopeptidase inhibitor | lepidoptera, aphids, mites, nematodes, whitefly |
| Lectines | lepidoptera, aphids, mites, nematodes, whitefly |
| Protease Inhibitors eg cystatin, patatin, CPTI, virgiferin | lepidoptera, aphids, mites, nematodes, whitefly |
| ribosome inactivating protein | lepidoptera, aphids, mites, nematodes, whitefly |
| stilbene synthase | lepidoptera, aphids, mites, nematodes, whitefly |
| HMG-CoA reductase | lepidoptera, aphids, mites, nematodes, whitefly |
| Cyst nematode hatching stimulus | cyst nematodes |
| Barnase | nematodes eg root knot nematodes and cyst nematodes |
| CBI | root knot nematodes |
| Antifeeding principles induced at a nematode feeding site | nematodes eg root knot nematodes, root cyst nematodes |

TABLE A16

Crop Sugarcane

| Effected target or expressed principle(s) | Crop phenotype/Tolerance to |
|---|---|
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenyiosuccinate synthesis |
| Anthranilate Synthase | Inhibitors of tryptophan synthesis and catabolism |
| Nitrilase | 3,5-dihalo-4-hydroxy-benzonitriles such as Bromoxynil and Ioxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |
| Polyphenol oxidase or Polyphenol oxidase antisense | bacterial or fungal pathogens |
| Metallothionein | bacterial or fungal pathogens |
| Ribonuclease | bacterial or fungal pathogens |
| Antifungal polypeptide AlyAFP | bacterial or fungal pathogens |
| oxalate oxidase | bacterial or fungal pathogens |
| glucose oxidase | bacterial or fungal pathogens |
| pyrrolnitrin synthesis genes | bacterial or fungal pathogens |
| serine/threonine kinases | bacterial or fungal pathogens |
| Cecropin B | bacterial or fungal pathogens |
| Phenylalanine ammonia lyase (PAL) | bacterial or fungal pathogens |
| Cf genes eg. Cf 9 Cf5 Cf4 Cf2 | bacterial or fungal pathogens |
| Osmotin | bacterial or fungal pathogens |
| Alpha Hordothionin | bacterial or fungal pathogens |
| Systemin | bacterial or fungal pathogens |
| Polygalacturonase inhibitors | bacterial or fungal pathogens |
| Prf regulatory gene | bacterial or fungal pathogens |
| phytoalexins | bacterial or fungal pathogens |
| B-1,3-glucanase antisense | bacterial or fungal pathogens |
| receptor kinase | bacterial or fungal pathogens |
| Hypersensitive response eliciting polypeptide | bacterial or fungal pathogens |
| Systemic acquires resistance (SAR) genes | viral, bacterial, fungal, nematodal pathogens |
| Lytic protein | bacterial or fungal pathogens |
| Lysozym | bacterial or fungal pathogens eg clavibacter |
| Chitinases | bacterial or fungal pathogens |
| Barnase | bacterial or fungal pathogens |
| Glucanases | bacterial or fungal pathogens |
| double stranded ribonuclease | viruses as SCMV, SrMV |
| Coat proteins | viruses as SCMV, SrMV |

TABLE A16-continued

Crop Sugarcane

| Effected target or expressed principle(s) | Crop phenotype/Tolerance to |
|---|---|
| 17 kDa or 60 kDa protein | viruses as SCMV, SrMV |
| Nuclear inclusion proteins eg. a or b or Nucleoprotein | viruses as SCMV, SrMV |
| Pseudoubiquitin | viruses as SCMV, SrMV |
| Replicase | viruses as SCMV, SrMV |
| Bacillus thuringiensis toxins, VIP 3, Bacillus cereus toxins, Photorabdus and Xenorhabdus toxins | lepidoptera, aphids, mites, nematodes, whitefly, beetles eg mexican rice borer |
| 3-Hydroxysteroid oxidase | lepidoptera, aphids, mites, nematodes, whitefly, beetles eg mexican rice borer |
| Peroxidase | lepidoptera, aphids, mites, nematodes, whitefly, beetles eg mexican rice borer |
| Aminopeptidase inhibitors eg. Leucine aminopeptidase inhibitor | lepidoptera, aphids, mites, nematodes, whitefly, beetles eg mexican rice borer |
| Lectines | lepidoptera, aphids, mites, nematodes, whitefly, beetles eg mexican rice borer |
| Protease Inhibitors eg cystatin, patatin, CPTI, virgiferin | lepidoptera, aphids, mites, nematodes, whitefly, beetles eg mexican rice borer |
| ribosome inactivating protein | lepidoptera, aphids, mites, nematodes, whitefly, beetles eg mexican rice borer |
| stilbene synthase | lepidoptera, aphids, mites, nematodes, whitefly, beetles eg mexican rice borer |
| HMG-CoA reductase | lepidoptera, aphids, mites, nematodes, whitefly, beetles eg mexican rice borer |
| Cyst nematode hatching stimulus | cyst nematodes |
| Barnase | nematodes eg root knot nematodes and cyst nematodes |
| CBI | root knot nematodes |
| Antifeeding principles induced at a nematode feeding site | nematodes eg root knot nematodes, root cyst nematodes |

TABLE A17

Crop Sunflower

| Effected target or expressed principle(s) | Crop phenotype/Tolerance to |
|---|---|
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzonitriles such as Bromoxynil and Ioxinyl |
| 5-Enolpyruvyl-3phosphoshikimate Synthase (EPSPS) | Glyphosate or sulfosate |

TABLE A17-continued

Crop Sunflower

| Effected target or expressed principle(s) | Crop phenotype/Tolerance to |
|---|---|
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |
| Polyphenol oxidase or Polyphenol oxidase antisense | bacterial or fungal pathogens |
| Metallothionein | bacterial or fungal pathogens |
| Ribonuclease | bacterial or fungal pathogens |
| Antifungal polypeptide AlyAFP | bacterial or fungal pathogens |
| oxalate oxidase | bacterial or fungal pathogens eg sclerotinia |
| glucose oxidase | bacterial or fungal pathogens |
| pyrrolnitrin synthesis genes | bacterial or fungal pathogens |
| serine/threonine kinases | bacterial or fungal pathogens |
| Cecropin B | bacterial or fungal pathogens |
| Phenylalanine ammonia lyase (PAL) | bacterial or fungal pathogens |
| Cf genes eg. Cf 9 Cf5 Cf4 Cf2 | bacterial or fungal pathogens |
| Osmotin | bacterial or fungal pathogens |
| Alpha Hordothionin | bacterial or fungal pathogens |
| Systemin | bacterial or fungal pathogens |
| Polygalacturonase inhibitors | bacterial or fungal pathogens |
| Prf regulatory gene | bacterial or fungal pathogens |
| phytoalexins | bacterial or fungal pathogens |
| B-1,3-glucanase antisense | bacterial or fungal pathogens |
| receptor kinase | bacterial or fungal pathogens |
| Hypersensitive response eliciting polypeptide | bacterial or fungal pathogens |
| Systemic acquires resistance (SAR) genes | viral, bacterial, fungal, nematodal pathogens |
| Lytic protein | bacterial or fungal pathogens |
| Lysozym | bacterial or fungal pathogens |
| Chitinases | bacterial or fungal pathogens |
| Barnase | bacterial or fungal pathogens |
| Glucanases | bacterial or fungal pathogens |
| double stranded ribonuclease | viruses as CMV, TMV |
| Coat proteins | viruses as CMV, TMV |
| 17 kDa or 60 kDa protein | viruses as CMV, TMV |
| Nuclear inclusion proteins eg. a or b or Nucleoprotein | viruses as CMV, TMV |
| Pseudoubiquitin | viruses as CMV, TMV |
| Replicase | viruses as CMV, TMV |
| Bacillus thuringiensis toxins, VIP 3, Bacillus cereus toxins, Photorabdus and Xenorhabdus toxins | lepidoptera, aphids, mites, nematodes, whitefly, beetles |
| 3-Hydroxysteroid oxidase | lepidoptera, aphids, mites, nematodes, whitefly, beetles |
| Peroxidase | lepidoptera, aphids, mites, nematodes, whitefly, beetles |
| Aminopeptidase inhibitors eg. Leucine aminopeptidase inhibitor | lepidoptera, aphids, mites, nematodes, whitefly, beetles |
| Lectines | lepidoptera, aphids, mites, nematodes, whitefly, beetles |
| Protease Inhibitors eg cystatin, patatin, CPTI, virgiferin | lepidoptera, aphids, mites, nematodes, whitefly, beetles |
| ribosome inactivating protein | lepidoptera, aphids, mites, nematodes, whitefly, beetles |
| stilbene synthase | lepidoptera, aphids, mites, nematodes, whitefly, beetles |
| HMG-CoA reductase | lepidoptera, aphids, mites, nematodes, whitefly, beetles |
| Cyst nematode hatching stimulus | cyst nematodes |
| Barnase | nematodes eg root knot nematodes and cyst nematodes |
| CBI | root knot nematodes |
| Antifeeding principles induced at a nematode feeding site | nematodes eg root knot nematodes, root cyst nematodes |

TABLE A18

Crop Sugarbeet, Beet root

| Effected target or expressed principle(s) | Crop phenotype/Tolerance to |
| --- | --- |
| Acetolactate synthase (ALS) | Sulfonylureas, Imidazolinones, Triazolopyrimidines, Pyrimidyloxybenzoates, Phtalides |
| AcetylCoA Carboxylase (ACCase) | Aryloxyphenoxyalkanecarboxylic acids, cyclohexanediones |
| Hydroxyphenylpyruvate dioxygenase (HPPD) | Isoxazoles such as Isoxaflutol or Isoxachlortol, Triones such as mesotrione or sulcotrione |
| Phosphinothricin acetyl transferase | Phosphinothricin |
| O-Methyl transferase | altered lignin levels |
| Glutamine synthetase | Glufosinate, Bialaphos |
| Adenylosuccinate Lyase (ADSL) | Inhibitors of IMP and AMP synthesis |
| Adenylosuccinate Synthase | Inhibitors of adenylosuccinate synthesis |
| Anthranilate Synthase | Inhibitors of tryptophan synthesis and catabolism |
| Nitrilase | 3,5-dihalo-4-hydroxy-benzonitriles such as Bromoxynil and Ioxinyl |
| 5-Enolpyruvyl-3phosphoshikimate Synthase (EPSPS) | Glyphosate or sulfosate |
| Glyphosate oxidoreductase | Glyphosate or sulfosate |
| Protoporphyrinogen oxidase (PROTOX) | Diphenylethers, cyclic imides, phenylpyrazoles, pyridin derivatives, phenopylate, oxadiazoles etc. |
| Cytochrome P450 eg. P450 SU1 or selection | Xenobiotics and herbicides such as Sulfonylureas |
| Polyphenol oxidase or Polyphenol oxidase antisense | bacterial or fungal pathogens |
| Metallothionein | bacterial or fungal pathogens |
| Ribonuclease | bacterial or fungal pathogens |
| Antifungal polypeptide AlyAFP | bacterial or fungal pathogens |
| oxalate oxidase | bacterial or fungal pathogens eg sclerotinia |
| glucose oxidase | bacterial or fungal pathogens |
| pyrrolnitrin synthesis genes | bacterial or fungal pathogens |
| serine/threonine kinases | bacterial or fungal pathogens |
| Cecropin B | bacterial or fungal pathogens |
| Phenylalanine ammonia lyase (PAL) | bacterial or fungal pathogens |
| Cf genes eg. Cf 9 Cf5 Cf4 Cf2 | bacterial or fungal pathogens |
| Osmotin | bacterial or fungal pathogens |
| Alpha Hordothionin | bacterial or fungal pathogens |
| Systemin | bacterial or fungal pathogens |
| Polygalacturonase inhibitors | bacterial or fungal pathogens |
| Prf regulatory gene | bacterial or fungal pathogens |
| phytoalexins | bacterial or fungal pathogens |
| B-1,3-glucanase antisense | bacterial or fungal pathogens |
| AX + WIN proteins | bacterial or fungal pathogens like Cercospora beticola |
| receptor kinase | bacterial or fungal pathogens |
| Hypersensitive response eliciting polypeptide | bacterial or fungal pathogens |
| Systemic acquires resistance (SAR) genes | viral, bacterial, fungal, nematodal pathogens |
| Lytic protein | bacterial or fungal pathogens |
| Lysozym | bacterial or fungal pathogens |
| Chitinases | bacterial or fungal pathogens |
| Barnase | bacterial or fungal pathogens |
| Glucanases | bacterial or fungal pathogens |
| double stranded ribonuclease | viruses as BNYVV |
| Coat proteins | viruses as BNYVV |
| 17 kDa or 60 kDa protein | viruses as BNYVV |
| Nuclear inclusion proteins eg. a or b or Nucleoprotein | viruses as BNYVV |
| Pseudoubiquitin | viruses as BNYVV |
| Replicase | viruses as BNYVV |
| Bacillus thuringiensis toxins, VIP 3, Bacillus cereus toxins, Photorabdus and Xenorhabdus toxins | lepidoptera, aphids, mites, nematodes, whitefly, beetles, rootflies |
| 3-Hydroxysteroid oxidase | lepidoptera, aphids, mites, nematodes, whitefly, beetles, rootflies |
| Peroxidase | lepidoptera, aphids, mites, nematodes, whitefly, beetles, rootflies |
| Aminopeptidase inhibitors eg. Leucine aminopeptidase inhibitor | lepidoptera, aphids, mites, nematodes, whitefly, beetles, rootflies |
| Lectines | lepidoptera, aphids, mites, nematodes, whitefly, beetles, rootflies |
| Protease Inhibitors eg cystatin, patatin, CPTI, virgiferin | lepidoptera, aphids, mites, nematodes, whitefly, beetles, rootflies |
| ribosome inactivating protein | lepidoptera, aphids, mites, nematodes, whitefly, beetles, rootflies |
| stilbene synthase | lepidoptera, aphids, mites, nematodes, whitefly, beetles, rootflies |
| HMG-CoA reductase | lepidoptera, aphids, mites, nematodes, whitefly, beetles, rootflies |
| Cyst nematode hatching stimulus | cyst nematodes |
| Barnase | nematodes eg root knot nematodes and cyst nematodes |
| Beet cyst nematode resistance locus CBI | cyst nematodes root knot nematodes |
| Antifeeding principles induced at a nematode feeding site | nematodes eg root knot nematodes, root cyst nematodes |

The abovementioned animal pests which can be controlled by the method according to the invention include, for example, insects, representatives of the order acarina and representatives of the class nematoda; especially from the order Lepidoptera Acleris spp., Adoxophyes spp., especially Adoxophyes reticulana; Aegeria spp., Agrotis spp., especially *Agrotis spinifera; Alabama argiliaceae*, Amylois spp., *Anticarsia gemmatalis*, Archips spp., Argyrotaenia spp., Autographa spp., *Busseola fusca, Cadra cautella, Carposina nipponensis*, Chilo spp., Choristoneura spp., *Clysia ambiguella*, Cnaphalocrocis spp., Cnephasia spp., Cochylis spp., Coleophora spp., *Crocidolomia binotalis, Cryptophlebia leucotreta*, Cydia spp., especially *Cydia pomonella*; Diatraea spp., *Diparopsis castanea*, Earias spp., Ephestia spp., especially E. Khüniella; Eucosma spp., *Eupoecilia ambiguella*, Euproctis spp., Euxoa spp, Grapholita spp., *Hedya nubiferana*, Heliothis spp., especially H. Virescens und H. zea; *Hellula undalis, Hyphantria cunea, Keiferia lycopersicella, Leucoptera scitella*, Lithocollethis spp., Lobesiaspp, Lymantria spp., Lyonetia spp., Malacosoma spp., *Mamestra brassicae, Manduca sexta*, Operophtera spp., *Ostrinia nubilalis*, Pammene spp., Pandemis spp., *Panolis flammea*, Pectinophora spp., *Phthorimaea operculella, Pieris rapae*, Pieris spp., *Plutella xylostella*, Prays spp., Scirpophaga spp., Sesamia spp., Sparganothis spp., Spodopteralittoralis, Synanthedon spp., Thaumetopoea spp., Tortrix spp., Trichoplusia ni and Yponomeuta spp.; from the order Coleoptera, for example Agriotes spp., Anthonomus spp., *Atomaria linearis, Chaetocnema tibialis*, Cosmopolites spp., Curculio spp., Dermestes spp., Diabrotica spp., Epilachna spp., Eremnus spp., *Leptinotarsa decemlineata*, Lissorhoptrus spp., Melolontha spp., Oryzaephilus spp., Otiorhynchus spp., Phlyctinus spp., Popillia spp., Psylliodes spp., Rhizopertha spp., Scarabeidae, Sitophilus spp., Sitotroga spp., Tenebrio spp., Tribolium spp. and Trogoderma spp.;

from the order Orthoptera, for example Blatta spp., Blattella spp., Gryllotalpa spp., *Leucophaea maderae*, Locusta spp., Periplaneta spp. and Schistocerca spp.;

from the order Isoptera, for example Reticulitermes spp.;

from the order Psocoptera, for example Liposcelis spp.;

from the order Anoplura, for example Haematopinus spp., Linognathus spp., Pediculus spp., Pemphigus spp. and Phylloxera spp.;

from the order Mallophaga, for example Damalinea spp. and Trichodectes spp.;

from the order Thysanoptera, for example Frankliniella spp., Hercinothrips spp., Taeniothrips spp., *Thrips palmi, Thrips tabaci* and *Scirtothrips aurantii;* from the order Heteroptera, for example Cimex spp., *Distantiella theobroma,* Dysdercus spp., Euchistus spp. Eurygaster spp. Leptocorisa spp., Nezara spp., Piesma spp., Rhodnius spp., *Sahlbergella singularis,* Scotinophara spp. and Triatoma spp.; from the order Homoptera, for example *Aleurothrixus floccosus, Aleyrodes brassicae, Aonidiella aurantii,* Aphididae, *Aphis craccivora, A. fabae, A. gosypii;* Aspidiotus spp., *Bemisia tabaci,* Ceroplaster spp., *Chrysomphalus aonidium, Chrysomphalus dictyospermi, Coccus hesperidum,* Empoasca spp., *Eriosoma lanigerum,* Erythroneura spp., Gascardia spp., Laodelphax spp., *Lecanium corni,* Lepidosaphes spp., Macrosiphus spp., Myzus spp., especially *M.persicae;* Nephotettix spp., especially *N. cincticeps;* Nilaparvata spp., especially *N. lugens;* Paratoria spp., Pemphigus spp., Planococcus spp., Pseudaulacaspis spp., Pseudococcus spp., especially *P. Fragilis, P. citriculus* and *P. comstocki;* Psylla spp., especially *P. pyri; Pulvinaria aethiopica,* Quadraspidiotus spp., Rhopalosiphum spp., Saissetia spp., Scaphoideus spp., Schizaphis spp., Sitobion spp., *Trialeurodes vaporariorum, Trioza erytreae* and *Unaspis citri;* from the order Hymenoptera, for example Acromyrmex, Atta spp., Cephus spp., Diprion spp., Diprionidae, *Gilpinia polytoma,* Hoplocampa spp., Lasius spp., *Monomorium pharaonis,* Neodiprion spp., Solenopsis spp. and Vespa spp.;

from the order Diptera, for example Aedes spp., *Antherigona soccata, Bibio hortulanus, Calliphora erythrocephala,* Ceratitis spp., Chrysomyia spp., Culex spp., Cuterebra spp., Dacus spp., *Drosophila melanogaster,* Fannia spp., Gastrophilus spp., Glossina spp., Hypoderma spp., Hyppobosca spp., Liriomyza spp., Lucilia spp., Melanagromyza spp., Musca spp., Oestrus spp., Orseolia spp., *Oscinella frit, Pegomya hyoscyami,* Phorbia spp., *Rhagoletis pomonella,* Sciara spp., Stomoxys spp., Tabanus spp., Tannia spp. and Tipula spp.;

from the order Siphonaptera, for example Ceratophyllus spp. and *Xenopsylla cheopis;* from the order Thysanura, for example *Lepima saccharina* and from the order Acarina, for example *Acarus siro, Aceria sheldoni;* Aculus spp., especially *A. schlechtendali;* Amblyomma spp., Argas spp., Boophilus spp., Brevipalpus spp., especially *B. californicus* and *B. phoenicis; Bryobia praetiosa,* Calipitrimerus spp., Chorioptes spp., *Dermanyssus gallinae,* Eotetranychus App., especially *E. carpini* and *E. orientalis;* Eriophyes spp., especially *E. vitis;* Hyalomma aspp., Ixodea spp., *Olygonychus pratensis,* Ornithodoros spp., Panonychus pp., especially *P. ulmi* and *P. citri;* Phyllocoptruta spp., especially *P. oleivora;* Polyphagotarsonemus spp., especially *P. latus;* Psoroptes spp., Rhipicephalus spp., Rhizoglyphus spp., Sarcoptes spp., Tarsonemus spp. and Tetranychus spp., in particular *T. urticae, T. cinnabarinus* and *T. Kanzawai;* representatives of the class Nematoda;

(1) nematodes selected from the group consisting of root knot nematodes, cyst-forming nematodes, stem eelworms and foliar nematodes;

(2) nematodes selected from the group consisting of Anguina spp.; Aphelenchoides spp.; Ditylenchus spp.; Globodera spp., for example *Globodera rostochiensis;* Heterodera spp., for example *Heterodera avenae, Heterodera glycines, Heterodera schachtii* or *Heterodera trifolii;* Longidorus spp.; Meloidogyne spp., for example *Meoidogyne incognita* or *Meloidogyne javanica;* Pratylenchus, for example *Pratylenchus neglectans* or *Pratylenchus penetrans;* Radopholus spp., for example *Radopholus similis;* Trichodorus spp.; Tylenchulus, for example *Tylenchulus semipenetrans;* and Xiphinema spp.; or (3) nematodes selected from the group consisting of Heterodera spp., for example *Heterodera glycines;* and Meloidogyne spp., for example *Meloidogyne incognita.*

The method according to the invention allows pests of the abovementioned type to be controlled, i.e. contained or destroyed, which occur, in particular, on transgenic plants, mainly useful plants and ornamentals in agriculture, in horticulture and in forests, or on parts, such as fruits, flowers, foliage, stalks, tubers or roots, of such plants, the protection against these pests in some cases even extending to plant parts which form at a later point in time.

The method according to the invention can be employed advantageously for controlling pests in rice, cereals such as maize or sorghum; in fruit, for example stone fruit, pome fruit and soft fruit such as apples, pears, plums, peaches, almonds, cherries or berries, for example strawberries, raspberries and blackberries; in legumes such as beans, lentils, peas or soya beans; in oil crops such as oilseed rape, mustard, poppies, olives, sunflowers, coconuts, castor-oil plants, cacao or peanuts; in the marrow family such as pumpkins, cucumbers or melons; in fibre plants such as cotton, flax, hemp or jute; in citrus fruit such as oranges, lemons, grapefruit or tangerines; in vegetables such as spinach, lettuce, asparagus, cabbage species, carrots, onions, tomatoes, potatoes, beet or capsicum; in the laurel family such as avocado, Cinnamonium or camphor; or in tobacco, nuts, coffee, egg plants, sugar cane, tea, pepper, grapevines, hops, the banana family, latex plants or omamentals, mainly in maize, rice, cereals, soya beans, tomatoes, cotton, potatoes, sugar beet, rice and mustard; in particular in cotton, rice, soya beans, potatoes and maize.

It has emerged that the method according to the invention is valuable preventatively and/or curatively in the field of pest control even at low use concentrations of the pesticidal composition and that a very favourable biocidal spectrum is achieved thereby. Combined with a favourable compatibility of the composition employed with warm-blooded species, fish and plants, the method according to the invention can be employed against all or individual developmental stages of normally-sensitive, but also of normally-resistant, animal pests such as insects and representatives of the order Acarina, depending on the species of the transgenic crop plant to be protected from attack by pests. The insecticidal and/or acaricidal effect of the method according to the invention may become apparent directly, i.e. in a destruction of the pests which occurs immediately or only after some time has elapsed, for example, during ecdysis, or indirectly, for example as a reduced oviposition and/or hatching rate, the good action corresponding to a destruction rate (mortality) of at least 40 to 50%.

Depending on the intended aims and the prevailing circumstances, the pesticides within the scope of invention, which are known per se, are emulsifiable concentrates, suspension concentrates, directly sprayable or dilutable solutions, spreadable pastes, dilute emulsions, wettable powders, soluble powders, dispersible powders, wettable powders, dusts, granules or encapsulations in polymeric substances which comprise pymetrozine; profenofos; a benzoylurea-derivative or a carbamat-derivative.

The active ingredients are employed in these compositions together with at least one of the auxiliaries conventionally used in art of formulation, such as extenders, for example solvents or solid carriers, or such as surface-active compounds (surfactants).

Formulation auxiliaries which are used are, for example, solid carriers, solvents, stabilizers, "slow release" auxiliaries, colourants and, if appropriate, surface-active substances (surfactants). Suitable carriers and auxiliaries are all those substances which are conventionally used for crop protection products. Suitable auxiliaries such as solvents, solid carriers, surface-active compounds, non-ionic surfactants, cationic surfactants, anionic surfactants and other auxiliaries in the compositions employed according to the invention are, for example, those which have been described in EP-A-736 252.

These compositions for controlling pests can be formulated, for example, as wettable powders, dusts, granules, solutions, emulsifiable concentrates, emulsions, suspension concentrates or aerosols. For example, the compositions are of the type described in EP-A-736 252.

The action of the compositions within the scope of invention which comprise pymetrozine, profenofos, a benzoylurea-derivative or a carbamat-derivative, can be extended substantially and adapted to prevailing circumstances by adding other insecticidally, acaricidally and/or fungicidally active ingredients. Suitable examples of added active ingredients are representatives of the following classes of active ingredients: organo-phosphorous compounds, nitrophenols and derivatives, formamidines, ureas, carbamates, pyrethroids, chlorinated hydrocarbons; especially preferred components in mixtures are, for example, are NI-25, TI-304, Clothiamidin (TI-435), MTI-446, fipronil, pyriproxyfen, thiacloprid, fluxofenime; imidacloprid, thiamethoxam, diafenthiuron, diazinon, disulphoton; furathiocarb, cyromazin, cypermethrin, tau-fluvalinate, tefluthrin or Bacillus thuringiensis products, As a rule, the compositions within the scope of invention comprise 0.1 to 99%, in particular 0.1 to 95 %, of an active ingredient according to the invention and 1 to 99.9 %, in particular 5 to 99.9 %, of—at least—one solid or liquid auxiliary, it being possible, as a rule, for 0 to 25 %, in particular 0.1 to 20 %, of the compositions to be surfactants (% in each case meaning per cent by weight). While concentrated compositions are more preferred as commercial products, the end user will, as a rule, use dilute compositions which have considerably lower concentrations of active ingredient.

The compositions according to the invention may also comprise other solid or liquid auxiliaries, such as stabilisers, for example epoxidized or unepoxidized vegetable oils (for example epoxidized coconut oil, rapeseed oil or soya bean oil), antifoams, for example silicone oil, preservatives, viscosity regulators, binders and/or tackifiers, and also fertilizers or other active ingredients for achieving specific effects, for example, bactericides, fungicides, nematicides, molluscicides or herbicides.

The compositions according to the invention are produced in a known manner, for example prior to mixing with the auxiliary/auxiliaries by grinding, screening and/or compressing the active ingredient, for example to give a particular particle size, and by intimately mixing and/or grinding the active ingredient with the auxiliary/auxiliaries.

The method according to the invention for controlling pests of the abovementioned type is carried out in a manner known per se to those skilled in the art, depending on the intended aims and prevailing circumstances, that is to say by spraying, wetting, atomizing, dusting, brushing on, seed dressing, scattering or pouring of the composition. Typical use concentrations are between 0.1 and 1000 ppm, preferably between 0.1 and 500 ppm of active ingredient. The application rate may vary within wide ranges and depends on the soil constitution, the type of application (foliar application; seed dressing; application in the seed furrow), the transgenic crop plant, the pest to be controlled, the climatic circumstances prevailing in each case, and other factors determined by the type of application, timing of application and target crop. The application rates per hectare are generally 1 to 2000 g of an active ingredient according to the invention per hectare, in particular 10 to 1000 g/ha, preferably 10 to 500 g/ha, especially preferably 10 to 200 g/ha.

A preferred type of application in the field of crop protection within the scope of invention is application to the foliage of the plants (foliar application), it being possible to adapt frequency and rate of application to the risk of infestation with the pest in question. However, the active ingredient may also enter into the plants via the root system (systemic action), by drenching the site of the plants with a liquid composition or by incorporating the active ingredient in solid form into the site of the plants, for example into the soil, for example in the form of granules (soil application). In the case of paddy rice crops, such granules may be metered into the flooded paddy field.

The compositions according to invention are also suitable for protecting propagation material of transgenic plants, for example seed, such as fruits, tubers or kernels, or plant cuttings, from animal pests, in particular insects and representatives of the order Acarina. The propagation material can be treated with the composition prior to application, for example, seed being dressed prior to sowing. The active ingredient may also be applied to seed kernels (coating), either by soaking the kernels in a liquid composition or by coating them with a solid composition. The composition may also be applied to the site of application when applying the propagation material, for example into the seed furrow during sowing. These treatment methods for plant propagation material and the plant propagation material treated thus are a further subject of the invention.

Examples of formulations of active ingredients which can be used in the method according to the invention, for instance solutions, granules, dusts, sprayable powders, emulsion concentrates, coated granules and suspension concentrates, are of the type as has been described in, for example, EP-A-580 553, Examples F1 to F10.

BIOLOGICAL EXAMPLES

TABLE B

The following abreviations are used in the table:
Active Principle of transgenic plant: AP
*Photorhabdus luminescens*: PL
*Xenorhabdus nematophilus*: XN
Proteinase Inhibitors: Pinh.
Plant lectins PLec.
Agglutinins: Aggl.
3-Hydroxysteroid oxidase: HO
Cholesteroloxidase: Co
Chitinase: CH
Glucanase: GL
Stilbensynthase SS

|   | AP | Control of |
|---|---|---|
| B.1 | CryIA (a) | Adoxophyes spp. |
| B.2 | CryIA (a) | Agrotis spp. |
| B.3 | CryIA (a) | *Alabama argillaceae* |
| B.4 | CryIA (a) | *Anticarsia gemmatalis* |
| B.5 | CryIA (a) | Chilo spp. |
| B.6 | CryIA (a) | *Clysia ambiguella* |
| B.7 | CryIA (a) | *Crocidolomia binotalis* |
| B.8 | CryIA (a) | Cydia spp. |
| B.9 | CryIA (a) | *Diparopsis castanea* |
| B.10 | CryIA (a) | Earias spp. |
| B.11 | CryIA (a) | Ephestia spp. |
| B.12 | CryIA (a) | Heliothis spp. |
| B.13 | CryIA (a) | *Hellula undalis* |
| B.14 | CryIA (a) | *Keiferia lycopersicella* |
| B.15 | CryIA (a) | *Leucoptera scitella* |
| B.16 | CryIA (a) | Lithocollethis spp. |
| B.17 | CryIA (a) | *Lobesia botrana* |
| B.18 | CryIA (a) | *Ostrinia nubilalis* |
| B.19 | CryIA (a) | Pandemis spp. |
| B.20 | CryIA (a) | *Pectinophora gossyp.* |
| B.21 | CryIA (a) | *Phyliocnistis citrella* |
| B.22 | CryIA (a) | Pieris spp. |
| B.23 | CryIA (a) | *Plutella xylostella* |
| B.24 | CryIA (a) | Scirpophaga spp. |
| B.25 | CryIA (a) | Sesamia spp. |
| B.26 | CryIA (a) | Sparganothis spp. |
| B.27 | CryIA (a) | Spodoptera spp. |
| B.28 | CryIA (a) | Tortrix spp. |
| B.29 | CryIA (a) | *Trichoplusia ni* |
| B.30 | CryIA (a) | Agriotes spp. |
| B.31 | CryIA (a) | *Anthonomus grandis* |
| B.32 | CryIA (a) | Curculio spp. |
| B.33 | CryIA (a) | *Diabrotica balteata* |
| B.34 | CryIA (a) | Leptinotarsa spp. |
| B.35 | CryIA (a) | Lissorhoptrus spp. |
| B.36 | CryIA (a) | Otiorhynchus spp. |
| B.37 | CryIA (a) | Aleurothrixus spp. |
| B.38 | CryIA (a) | Aleyrodes spp. |
| B.39 | CryIA (a) | Aonidiella spp. |
| B.40 | CryIA (a) | Aphididae spp. |
| B.41 | CryIA (a) | Aphis spp. |
| B.42 | CryIA (a) | *Bemisia tabaci* |
| B.43 | CryIA (a) | Empoasca spp. |
| B.44 | CryIA (a) | Mycus spp. |
| B.45 | CryIA (a) | Nephotettix spp. |
| B.46 | CryIA (a) | Nilaparvata spp. |
| B.47 | CryIA (a) | Pseudococcus spp. |
| B.48 | CryIA (a) | Psylla spp. |
| B.49 | CryIA (a) | Quadraspidiotus spp. |
| B.50 | CryIA (a) | Schizaphis spp. |
| B.51 | CryIA (a) | Trialeurodes spp. |
| B.52 | CryIA (a) | Lyriomyza spp. |
| B.53 | CryIA (a) | Oscinella spp. |
| B.54 | CryIA (a) | Phorbia spp. |
| B.55 | CryIA (a) | Frankliniella spp. |
| B.56 | CryIA (a) | Thrips spp. |
| B.57 | CryIA (a) | *Scirtothrips aurantii* |
| B.58 | CryIA (a) | Aceria spp. |
| B.59 | CryIA (a) | Aculus spp. |
| B.60 | CryIA (a) | Brevipalpus spp. |
| B.61 | CryIA (a) | Panonychus spp. |
| B.62 | CryIA (a) | Phyllocoptruta spp. |
| B.63 | CryIA (a) | Tetranychus spp. |
| B.64 | CryIA (a) | Heterodera spp. |
| B.65 | CryIA (a) | Meloidogyne spp. |
| B.66 | CryIA (b) | Adoxophyes spp. |
| B.67 | CryIA (b) | Agrotis spp. |
| B.68 | CryIA (b) | *Alabama argillaceae* |
| B.69 | CryIA (b) | *Anticarsia gemmatalis* |
| B.70 | CryIA (b) | Chilo spp. |
| B.71 | CryIA (b) | *Clysia ambiguella* |
| B.72 | CryIA (b) | *Crocidolomia binotalis* |
| B.73 | CryIA (b) | Cydia spp. |
| B.74 | CryIA (b) | *Diparopsis castanea* |
| B.75 | CryIA (b) | Earias spp. |
| B.76 | CryIA (b) | Ephestia spp. |
| B.77 | CryIA (b) | Heliothis spp. |
| B.78 | CryIA (b) | *Hellula undalis* |
| B.79 | CryIA (b) | *Keiferia lycopersicella* |
| B.80 | CryIA (b) | *Leucoptera scitella* |
| B.81 | CryIA (b) | Lithocollethis spp. |
| B.82 | CryIA (b) | *Lobesia botrana* |
| B.83 | CryIA (b) | *Ostrinia nubilalis* |
| B.84 | CryIA (b) | Pandemis spp. |
| B.85 | CryIA (b) | *Pectinophora gossyp.* |
| B.86 | CryIA (b) | *Phyllocnistis citrella* |
| B.87 | CryIA (b) | Pieris spp. |
| B.88 | CryIA (b) | *Plutella xylostella* |
| B.89 | CryIA (b) | Scirpophaga spp. |
| B.90 | CryIA (b) | Sesamia spp. |
| B.91 | CryIA (b) | Sparganothis spp. |
| B.92 | CryIA (b) | Spodoptera spp. |
| B.93 | CryIA (b) | Tortrix spp. |
| B.94 | CryIA (b) | *Trichoplusia ni* |
| B.95 | CryIA (b) | Agriotes spp. |
| B.96 | CryIA (b) | *Anthonomus grandis* |
| B.97 | CryIA (b) | Curculio spp. |
| B.98 | CryIA (b) | *Diabrotica balteata* |
| B.99 | CryIA (b) | Leptinotarsa spp. |
| B.100 | CryIA (b) | Lissorhoptrus spp. |
| B.101 | CryIA (b) | Otiorhynchus spp. |
| B.102 | CryIA (b) | Aleurothrixus spp. |
| B.103 | CryIA (b) | Aleyrodes spp. |
| B.104 | CryIA (b) | Aonidiella spp. |
| B.105 | CryIA (b) | Aphididae spp. |
| B.106 | CryIA (b) | Aphis spp. |
| B.107 | CryIA (b) | *Bemisia tabaci* |
| B.108 | CryIA (b) | Empoasca spp. |
| B.109 | CryIA (b) | Mycus spp. |
| B.110 | CryIA (b) | Nephotettix spp. |
| B.111 | CryIA (b) | Nilaparvata spp. |
| B.112 | CryIA (b) | Pseudococcus spp. |
| B.113 | CryIA (b) | Psylla spp. |
| B.114 | CryIA (b) | Quadraspidiotus spp. |
| B.115 | CryIA (b) | Schizaphis spp. |
| B.116 | CryIA (b) | Trialeurodes spp. |
| B.117 | CryIA (b) | Lyriomyza spp. |
| B.118 | CryIA (b) | Oscinella spp. |
| B.119 | CryIA (b) | Phorbia spp. |
| B.120 | CryIA (b) | Frankliniella spp. |
| B.121 | CryIA (b) | Thrips spp. |
| B.122 | CryIA (b) | *Scirtothrips aurantii* |
| B.123 | CryIA (b) | Aceria spp. |
| B.124 | CryIA (b) | Aculus spp. |
| B.125 | CryIA (b) | Brevipalpus spp. |

TABLE B-continued

| | | |
|---|---|---|
| B.126 | CryIA (b) | Panonychus spp. |
| B.127 | CryIA (b) | Phyllocoptruta spp. |
| B.128 | CryIA (b) | Tetranychus spp. |
| B.129 | CryIA (b) | Heterodera spp. |
| B.130 | CryIA (b) | Meloidogyne spp. |
| B.131 | CryIA (c) | Adoxophyes spp. |
| B.132 | CryIA (c) | Agrotis spp. |
| B.133 | CryIA (c) | *Alabama argillaceae* |
| B.134 | CryIA (c) | *Anticarsia gemmatalis* |
| B.135 | CryIA (c) | Chilo spp. |
| B.136 | CryIA (c) | Clysia ambigueiia |
| B.137 | CryIA (c) | *Crocidolomia binotalis* |
| B.138 | CryIA (c) | Cydia spp. |
| B.139 | CryIA (c) | *Diparopsis castanea* |
| B.140 | CryIA (c) | Earias spp. |
| B.141 | CryIA (c) | Ephestia spp. |
| B.142 | CryIA (c) | Heliothis spp. |
| B.143 | CryIA (c) | *Hellula undalis* |
| B.144 | CryIA (c) | *Keiferia lycopersicella* |
| B.145 | CryIA (c) | *Leucoptera scitella* |
| B.146 | CryIA (c) | Lithocollethis spp. |
| B.147 | CryIA (c) | *Lobesia botrana* |
| B.148 | CryIA (c) | *Ostrinia nubilalis* |
| B.149 | CryIA (c) | Pandemis spp. |
| B.150 | CryIA (c) | *Pectinophora gossypiella.* |
| B.151 | CryIA (c) | *Phyllocnistis citrella* |
| B.152 | CryIA (c) | Pieris spp. |
| B.153 | CryIA (c) | *Plutella xylostella* |
| B.154 | CryIA (c) | Scirpophaga spp. |
| B.155 | CryIA (c) | Sesamia spp. |
| B.156 | CryIA (c) | Sparganothis spp. |
| B.157 | CryIA (c) | Spodoptera spp. |
| B.158 | CryIA (c) | Tortrix spp. |
| B.159 | CryIA (c) | *Trichoplusia ni* |
| B.160 | CryIA (c) | Agriotes spp. |
| B.161 | CryIA (c) | *Anthonomus grandis* |
| B.162 | CryIA (c) | Curculio spp. |
| B.163 | CryIA (c) | *Diabrotica balteata* |
| B.164 | CryIA (c) | Leptinotarsa spp. |
| B.165 | CryIA (c) | Lissorhoptrus spp. |
| B.166 | CryIA (c) | Otiorhynchus spp. |
| B.167 | CryIA (c) | Aleurothrixus spp. |
| B.168 | CryIA (c) | Aleyrodes spp. |
| B.169 | CryIA (c) | Aonidiella spp. |
| B.170 | CryIA (c) | Aphididae spp. |
| B.171 | CryIA (c) | Aphis spp. |
| B.172 | CryIA (c) | Bemisia tabaci |
| B.173 | CryIA (c) | Empoasca spp. |
| B.174 | CryIA (c) | Mycus spp. |
| B.175 | CryIA (c) | Nephotettix spp. |
| B.176 | CryIA (c) | Nilaparvata spp. |
| B.177 | CryIA (c) | Pseudococcus spp. |
| B.178 | CryIA (c) | Psylla spp. |
| B.179 | CryIA (c) | Quadraspidiotus spp. |
| B.180 | CryIA (c) | Schizaphis spp. |
| B.181 | CryIA (c) | Trialeurodes spp. |
| B.182 | CryIA (c) | Lyriomyza spp. |
| B.183 | CryIA (c) | Oscinella spp. |
| B.184 | CryIA (c) | Phorbia spp. |
| B.185 | CryIA (c) | Frankliniella spp. |
| B.186 | CryIA (c) | Thrips spp. |
| B.187 | CryIA (c) | *Scirtothrips aurantii* |
| B.188 | CryIA (c) | Aceria spp. |
| B.189 | CryIA (c) | Aculus spp. |
| B.190 | CryIA (c) | Brevipalpus spp. |
| B.191 | CryIA (c) | Panonychus spp. |
| B.192 | CryIA (c) | Phyllocoptruta spp. |
| B.193 | CryIA (c) | Tetranychus spp. |
| B.194 | CryIA (c) | Heterodera spp. |
| B.195 | CryIA (c) | Meloidogyne spp. |
| B.196 | CryIIA | Adoxophyes spp. |
| B.197 | CryIIA | Agrotis spp. |
| B.198 | CryIIA | *Alabama argillaceae* |
| B.199 | CryIIA | *Anticarsia gemmatalis* |
| B.200 | CryIIA | Chilo spp. |
| B.201 | CryIIA | *Clysia ambiguella* |
| B.202 | CryIIA | *Crocidolomia binotalis* |
| B.203 | CryIIA | Cydia spp. |
| B.204 | CryIIA | *Diparopsis castanea* |
| B.205 | CryIIA | Earias spp. |
| B.206 | CryIIA | Ephestia spp. |
| B.207 | CryIIA | Heliothis spp. |
| B.208 | CryIIA | *Hellula undalis* |
| B.209 | CryIIA | *Keiferia lycopersicella* |
| B.210 | CryIIA | *Leucoptera scitella* |
| B.211 | CryIIA | Lithocollethis spp. |
| B.212 | CryIIA | *Lobesia botrana* |
| B.213 | CryIIA | *Ostrinia nubilalis* |
| B.214 | CryIIA | Pandemis spp. |
| B.215 | CryIIA | *Pectinophora gossyp.* |
| B.216 | CryIIA | Phyllocnistis citrella |
| B.217 | CryIIA | Pieris spp. |
| B.218 | CryIIA | *Plutella xylostella* |
| B.219 | CryIIA | Scirpophaga spp. |
| B.220 | CryIIA | Sesamia spp. |
| B.221 | CryIIA | Sparganothis spp. |
| B.222 | CryIIA | Spodoptera spp. |
| B.223 | CryIIA | Tortrix spp. |
| B.224 | CryIIA | *Trichoplusia ni* |
| B.225 | CryIIA | Agriotes spp. |
| B.226 | CryIIA | *Anthonomus grandis* |
| B.227 | CryIIA | Curculio spp. |
| B.228 | CryIIA | *Diabrotica balteata* |
| B.229 | CryIIA | Leptinotarsa spp. |
| B.230 | CryIIA | Lissorhoptrus spp. |
| B.231 | CryIIA | Otiorhynchus spp. |
| B.232 | CryIIA | Aleurothrixus spp. |
| B.233 | CryIIA | Aleyrodes spp. |
| B.234 | CryIIA | Aonidiella spp. |
| B.235 | CryIIA | Aphididae spp. |
| B.236 | CryIIA | Aphis spp. |
| B.237 | CryIIA | *Bemisia tabaci* |
| B.238 | CryIIA | Empoasca spp. |
| B.239 | CryIIA | Mycus spp. |
| B.240 | CryIIA | Nephotettix spp. |
| B.241 | CryIIA | Nilaparvata spp. |
| B.242 | CryIIA | Pseudococcus spp. |
| B.243 | CryIIA | Psylla spp. |
| B.244 | CryIIA | Quadraspidiotus spp. |
| B.245 | CryIIA | Schizaphis spp. |
| B.246 | CryIIA | Trialeurodes spp. |
| B.247 | CryIIA | Lyriomyza spp. |
| B.248 | CryIIA | Oscinella spp. |
| B.249 | CryIIA | Phorbia spp. |
| B.250 | CryIIA | Frankiiniella spp. |
| B.251 | CryIIA | Thrips spp. |
| B.252 | CryIIA | *Scirtothrips aurantii* |
| B.253 | CryIIA | Aceria spp. |
| B.254 | CryIIA | Aculus spp. |
| B.255 | CryIIA | Brevipalpus spp. |
| B.256 | CryIIA | Panonychus spp. |
| B.257 | CryIIA | Phyllocoptruta spp. |
| B.258 | CryIIA | Tetranychus spp. |
| B.259 | CryIIA | Heterodera spp. |
| B.260 | CryIIA | Meloidogyne spp. |
| B.261 | CryIIIA | Adoxophyes spp. |
| B.262 | CryIIIA | Agrotis spp. |
| B.263 | CryIIIA | *Alabama argillaceae* |
| B.264 | CryIIIA | *Anticarsia gemmatalis* |
| B.265 | CryIIIA | Chilo spp. |

TABLE B-continued

| | | |
|---|---|---|
| B.266 | CryIIIA | *Clysia ambiguella* |
| B.267 | CryIIIA | *Crocidolomia binotalis* |
| B.268 | CryIIIA | Cydia spp. |
| B.269 | CryIIIA | *Diparopsis castanea* |
| B.270 | CryIIIA | Earias spp. |
| B.271 | CryIIIA | Ephestia spp. |
| B.272 | CryIIIA | Heliothis spp. |
| B.273 | CryIIIA | *Hellula undalis* |
| B.274 | CryIIIA | *Keiferia lycopersicella* |
| B.275 | CryIIIA | *Leucoptera scitella* |
| B.276 | CryIIIA | Lithocollethis spp. |
| B.277 | CryIIIA | *Lobesia botrana* |
| B.278 | CryIIIA | *Ostrinia nubilalis* |
| B.279 | CrytlIA | Pandemis spp. |
| B.280 | CryIIIA | *Pectinophora gossyp.* |
| B.281 | CryIIIA | *Phyllocnistis citrella* |
| B.282 | CryIIIA | Pieris spp. |
| B.283 | CryIIIA | *Plutella xytostella* |
| B.284 | CryIIIA | Scirpophaga spp. |
| B.285 | CryIIIA | Sesamia spp. |
| B.286 | CryIIIA | Sparganothis spp. |
| B.287 | CryIIIA | Spodoptera spp. |
| B.288 | CryIIIA | Tortrix spp. |
| B.289 | CryIIIA | *Trichoplusia ni* |
| B.290 | CryIIIA | Agriotes spp. |
| B.291 | CryIIIA | *Anthonomus grandis* |
| B.292 | CryIIIA | Curculio spp. |
| B.293 | CryIIIA | *Diabrotica balteata* |
| B.294 | CryIIIA | Leptinotarsa spp. |
| B.295 | CryIIIA | Lissorhoptrus spp. |
| B.296 | CryIIIA | Otiorhynchus spp. |
| B.297 | CryIIIA | Aleurothrixus spp. |
| B.298 | CryIIIA | Aleyrodes spp. |
| B.299 | CryIIIA | Aonidiella spp. |
| B.300 | CryIIIA | Aphididae spp. |
| B.301 | CryIIIA | Aphis spp. |
| B.302 | CryIIIA | *Bemisia tabaci* |
| B.303 | CryIIIA | Empoasca spp. |
| B.304 | CryIIIA | Mycus spp. |
| B.305 | CryIIIA | Nephotettix spp. |
| B.306 | CryIIIA | Nilaparvata spp. |
| B.307 | CryIIIA | Pseudococcus spp. |
| B.308 | CryIIIA | Psylla spp. |
| B.309 | CryIIIA | Quadraspidiotus spp. |
| B.310 | CryIIIA | Schizaphis spp. |
| B.311 | CryIIIA | Trialeurodes spp. |
| B.312 | CryIIIA | Lyriomyza spp. |
| B.313 | CryIIIA | Oscinella spp. |
| B.314 | CryIIIA | Phorbia spp. |
| B.315 | CryIIIA | Frankliniella spp. |
| B.316 | CryIIIA | Thrips spp. |
| B.317 | CryIIIA | *Scirtothrips aurantii* |
| B.318 | CryIIIA | Aceria spp. |
| B.319 | CryIIIA | Aculus spp. |
| B.320 | CryIIIA | Brevipalpus spp. |
| B.321 | CryIIIA | Panonychus spp. |
| B.322 | CryIIIA | Phyllocoptruta spp. |
| B.323 | CryIIIA | Tetranychus spp. |
| B.324 | CryIIIA | Heterodera spp. |
| B.325 | CryIIIA | Meloidogyne spp. |
| B.326 | CryIIIB2 | Adoxophyes spp. |
| B.327 | CryIIIB2 | Agrotis spp. |
| B.328 | CryIIIB2 | *Alabama argillaceae* |
| B.329 | CryIIIB2 | *Anticarsia gemmatalis* |
| B.330 | CryIIIB2 | Chilo spp. |
| B.331 | CryIIIB2 | *Clysia ambiguella* |
| B.332 | CryIIIB2 | *Crocidolomia binotalis* |
| B.333 | CryIIIB2 | Cydia spp. |
| B.334 | CryIIIB2 | *Diparopsis castanea* |
| B.335 | CryIIIB2 | Earias spp. |
| B.336 | CryIIIB2 | Ephestia spp. |
| B.337 | CryIIIB2 | Heliothis spp. |
| B.338 | CryIIIB2 | Hellula undalis |
| B.339 | CryIIIB2 | *Keiferia lycopersicella* |
| B.340 | CryIIIB2 | *Leucoptera scitella* |
| B.341 | CryIIIB2 | Lithocollethis spp. |
| B.342 | CryIIIB2 | *Lobesia botrana* |
| B.343 | CryIIIB2 | *Ostrinia nubilalis* |
| B.344 | CryIIIB2 | Pandemis spp. |
| B.345 | CryIIIB2 | *Pectinophora gossyp.* |
| B.346 | CryIIIB2 | *Phyllocnistis citrella* |
| B.347 | CryIIIB2 | Pieris spp. |
| B.348 | CryIIIB2 | Plutella xylostella |
| B.349 | CryIIIB2 | Scirpophaga spp. |
| B.350 | CryIIIB2 | Sesamia spp. |
| B.351 | CryIIIB2 | Sparganothis spp. |
| B.352 | CryIIIB2 | Spodoptera spp. |
| B.353 | CryIIIB2 | Tortrix spp. |
| B.354 | CryIIIB2 | *Trichoplusia ni* |
| B.355 | CryIIIB2 | Agriotes spp. |
| B.356 | CryIIIB2 | *Anthonomus grandis* |
| B.357 | CryIIIB2 | Curculio spp. |
| B.358 | CryIIIB2 | *Diabrotica balteata* |
| B.359 | CryIIIB2 | Leptinotarsa spp. |
| B.360 | CryIIIB2 | Lissorhoptrus spp. |
| B.361 | CryIIIB2 | Otiorhynchus spp. |
| B.362 | CryIIIB2 | Aleurothrixus spp. |
| B.363 | CryIIIB2 | Aleyrodes spp. |
| B.364 | CryIIIB2 | Aonidiella spp. |
| B.365 | CryIIIB2 | Aphididae spp. |
| B.366 | CryIIIB2 | Aphis spp. |
| B.367 | CryIIIB2 | *Bemisia tabaci* |
| B.368 | CryIIIB2 | Empoasca spp. |
| B.369 | CryIIIB2 | Mycus spp. |
| B.370 | CryIIIB2 | Nephotettix spp. |
| B.371 | CryIIIB2 | Nilaparvata spp. |
| B.372 | CryIIIB2 | Pseudococcus spp. |
| B.373 | CryIIIB2 | Psylla spp. |
| B.374 | CryIIIB2 | Quadraspidiotus spp. |
| B.375 | CryIIIB2 | Schizaphis spp. |
| B.376 | CryIIIB2 | Trialeurodes spp. |
| B.377 | CryIIIB2 | Lyriomyza spp. |
| B.378 | CryIIIB2 | Oscinella spp. |
| B.379 | CryIIIB2 | Phorbia spp. |
| B.380 | CryIIIB2 | Frankliniella spp. |
| B.381 | CryIIIB2 | Thrips spp. |
| B.382 | CryIIIB2 | *Scirtothrips aurantii* |
| B.383 | CryIIIB2 | Aceria spp. |
| B.384 | CryIIIB2 | Aculus spp. |
| B.385 | CryIIIB2 | Brevipalpus spp. |
| B.386 | CryIIIB2 | Panonychus spp. |
| B.387 | CryIIIB2 | Phyllocoptruta spp. |
| B.388 | CryIIIB2 | Tetranychus spp. |
| B.389 | CryIIIB2 | Heterodera spp. |
| B.390 | CryIIIB2 | Meloidogyne spp. |
| B.391 | CytA | Adoxophyes spp. |
| B.392 | CytA | Agrotis spp. |
| B.393 | CytA | *Alabama argillaceae* |
| B.394 | CytA | *Anticarsia gemmatalis* |
| B.395 | CytA | Chilo spp. |
| B.396 | CytA | *Clysia ambiguella* |
| B.397 | CytA | *Crocidolomia binotalis* |
| B.398 | CytA | Cydia spp. |
| B.399 | CytA | *Diparopsis castanea* |
| B.400 | CytA | Earias spp. |
| B.401 | CytA | Ephestia spp. |
| B.402 | CytA | Heliothis spp. |
| B.403 | CytA | Hellula undalis |
| B.404 | CytA | *Keiferia lycopersicella* |

TABLE B-continued

| | | |
|---|---|---|
| B.405 | CytA | Leucoptera scitella |
| B.406 | CytA | Lithocollethis spp. |
| B.407 | CytA | Lobesia botrana |
| B.408 | CytA | Ostrinia nubilalis |
| B.409 | CytA | Pandemis spp. |
| B.410 | CytA | Pectinophora gossyp. |
| B.411 | CytA | Phyllocnistis citrella |
| B.412 | CytA | Pieris spp. |
| B.413 | CytA | Plutella xylostella |
| B.414 | CytA | Scirpophaga spp. |
| B.415 | CytA | Sesamia spp. |
| B.416 | CytA | Sparganothis spp. |
| B.417 | CytA | Spodoptera spp. |
| B.418 | CytA | Tortrix spp. |
| B.419 | CytA | Trichoplusia ni |
| B.420 | CytA | Agriotes spp. |
| B.421 | CytA | Anthonomus grandis |
| B.422 | CytA | Curculio spp. |
| B.423 | CytA | Diabrotica balteata |
| B.424 | CytA | Leptinotarsa spp. |
| B.425 | CytA | Lissorhoptrus spp. |
| B.426 | CytA | Otiorhynchus spp. |
| B.427 | CytA | Aleurothrixus spp. |
| B.428 | CytA | Aleyrodes spp. |
| B.429 | CytA | Aonidiella spp. |
| B.430 | CytA | Aphididae spp. |
| B.431 | CytA | Aphis spp. |
| B.432 | CytA | Bemisia tabaci |
| B.433 | CytA | Empoasca spp. |
| B.434 | CytA | Mycus spp. |
| B.435 | CytA | Nephotettix spp. |
| B.436 | CytA | Nilaparvata spp. |
| B.437 | CytA | Pseudococcus spp. |
| B.438 | CytA | Psylla spp. |
| B.439 | CytA | Quadraspidiotus spp. |
| B.440 | CytA | Schizaphis spp. |
| B.441 | CytA | Trialeurodes spp. |
| B.442 | CytA | Lyriomyza spp. |
| B.443 | CytA | Oscinella spp. |
| B.444 | CytA | Phorbia spp. |
| B.445 | CytA | Frankliniella spp. |
| B.446 | CytA | Thrips spp. |
| B.447 | CytA | Scirtothrips aurantii |
| B.448 | CytA | Aceria spp. |
| B.449 | CytA | Aculus spp. |
| B.450 | CytA | Brevipalpus spp. |
| B.451 | CutA | Panonychus spp. |
| B.452 | CytA | Phyllocoptruta spp. |
| B.453 | CytA | Tetranychus spp. |
| B.454 | CytA | Heterodera spp. |
| B.455 | CytA | Meloidogyne spp. |
| B.456 | VIP3 | Adoxophyes spp. |
| B.457 | VIP3 | Agrotis spp. |
| B.458 | VIP3 | Alabama argillaceae |
| B.459 | VIP3 | Anticarsia gemmatalis |
| B.460 | VIP3 | Chilo spp. |
| B.461 | VIP3 | Clysia ambiguella |
| B.462 | VIP3 | Crocidolomia binotalis |
| B.463 | VIP3 | Cydia spp. |
| B.464 | VIP3 | Diparopsis castanea |
| B.465 | VIP3 | Earias spp. |
| B.466 | VIP3 | Ephestia spp. |
| B.467 | VIP3 | Heliothis spp. |
| B.468 | VIP3 | Hellula undalis |
| B.469 | VIP3 | Keiferia lycopersicella |
| B.470 | VIP3 | Leucoptera scitella |
| B.471 | VIP3 | Lithocollethis spp. |
| B.472 | VIP3 | Lobesia botrana |
| B.473 | VIP3 | Ostrinia nubilalis |
| B.474 | VIP3 | Pandemis spp. |
| B.475 | VIP3 | Pectinophora gossyp. |
| B.476 | VIP3 | Phyllocnistis citrella |
| B.477 | VIP3 | Pieris spp. |
| B.478 | VIP3 | Plutella xylostella |
| B.479 | VIP3 | Scirpophaga spp. |
| B.480 | VIP3 | Sesamia spp. |
| B.481 | VIP3 | Sparganothis spp. |
| B.482 | VIP3 | Spodoptera spp. |
| B.483 | VIP3 | Tortrix spp. |
| B.484 | VIP3 | Trichoplusia ni |
| B.485 | VIP3 | Agriotes spp. |
| B.486 | VIP3 | Anthonomus grandis |
| B.487 | VIP3 | Curculio spp. |
| B.488 | VIP3 | Diabrotica balteata |
| B.489 | VIP3 | Leptinotarsa spp. |
| B.490 | VIP3 | Lissorhoptrus spp. |
| B.491 | VIP3 | Otiorhynchus spp. |
| B.492 | VIP3 | Aleurothrixus spp. |
| B.493 | VIP3 | Aleyrodes spp. |
| B.494 | VIP3 | Aonidiella spp. |
| B.495 | VIP3 | Aphididae spp. |
| B.496 | VIP3 | Aphis spp. |
| B.497 | VIP3 | Bemisia tabaci |
| B.498 | VIP3 | Empoasca spp. |
| B.499 | VIP3 | Mycus spp. |
| B.500 | VIP3 | Nephotettix spp. |
| B.501 | VIP3 | Nilaparvata spp. |
| B.502 | VIP3 | Pseudococcus spp. |
| B.503 | VIP3 | Psylla spp. |
| B.504 | VIP3 | Quadraspidiotus spp. |
| B.505 | VIP3 | Schizaphis spp. |
| B.506 | VIP3 | Trialeurodes spp. |
| B.507 | VIP3 | Lyriomyza spp. |
| B.508 | VIP3 | Oscinella spp. |
| B.509 | VIP3 | Phorbia spp. |
| B.510 | VIP3 | Frankliniella spp. |
| B.511 | VIP3 | Thrips spp. |
| B.512 | VIP3 | Scirtothrips aurantii |
| B.513 | VIP3 | Aceria spp. |
| B.514 | VIP3 | Aculus spp. |
| B.515 | VIP3 | Brevipalpus spp. |
| B.516 | VIP3 | Panonychus spp. |
| B.517 | VIP3 | Phyllocoptruta spp. |
| B.518 | VIP3 | Tetranychus spp. |
| B.519 | VIP3 | Heterodera spp. |
| B.520 | VIP3 | Meloidogyne spp. |
| B.521 | GL | Adoxophyes spp. |
| B.522 | GL | Agrotis spp. |
| B.523 | GL | Alabama argillaceae |
| B.524 | GL | Anticarsia gemmatalis |
| B.525 | GL | Chilo spp. |
| B.526 | GL | Clysia ambiguella |
| B.527 | GL | Crocidolomia binotalis |
| B.528 | GL | Cydia spp. |
| B.529 | GL | Diparopsis castanea |
| B.530 | GL | Earias spp. |
| B.531 | GL | Ephestia spp. |
| B.532 | GL | Heliothis spp. |
| B.533 | GL | Hellula undalis |
| B.534 | GL | Keiferia lycopersicella |
| B.535 | GL | Leucoptera scitella |
| B.536 | GL | Lithocollethis spp. |
| B.537 | GL | Lobesia botrana |
| B.538 | GL | Ostrinia nubilalis |
| B.539 | GL | Pandemis spp. |
| B.540 | GL | Pectinophora gossyp. |
| B.541 | GL | Phyllocnistis citrella |
| B.542 | GL | Pieris spp. |
| B.543 | GL | Plutella xylostella |
| B.544 | GL | Scirpophaga spp. |

TABLE B-continued

| | | |
|---|---|---|
| B.545 | GL | Sesamia spp. |
| B.546 | GL | Sparganothis spp. |
| B.547 | GL | Spodoptera spp. |
| B.548 | GL | Tortrix spp. |
| B.549 | GL | *Trichoplusia ni* |
| B.550 | GL | Agriotes spp. |
| B.551 | GL | Anthonomus grandis |
| B.552 | GL | Curculio spp. |
| B.553 | GL | *Diabrotica balteata* |
| B.554 | GL | Leptinotarsa spp. |
| B.555 | GL | Lissorhoptrus spp. |
| B.556 | GL | Otiorhynchus spp. |
| B.557 | GL | Aleurothrixus spp. |
| B.558 | GL | Aleyrodes spp. |
| B.559 | GL | Aonidiella spp. |
| B.560 | GL | Aphididae spp. |
| B.561 | GL | Aphis spp. |
| B.562 | GL | *Bemisia tabaci* |
| B.563 | GL | Empoasca spp. |
| B.564 | GL | Mycus spp. |
| B.565 | GL | Nephotettix spp. |
| B.566 | GL | Nilaparvata spp. |
| B.567 | GL | Pseudococcus spp. |
| B.568 | GL | Psylla spp. |
| B.569 | GL | Quadraspidiotus spp. |
| B.570 | GL | Schizaphis spp. |
| B.571 | GL | Trialeurodes spp. |
| B.572 | GL | Lyriomyza spp. |
| B.573 | GL | Oscinella spp. |
| B.574 | GL | Phorbia spp. |
| B.575 | GL | Frankliniella spp. |
| B.576 | GL | Thrips spp. |
| B.577 | GL | *Scirtothrips aurantii* |
| B.578 | GL | Aceria spp. |
| B.579 | GL | Aculus spp. |
| B.580 | GL | Brevipalpus spp. |
| B.581 | GL | Panonychus spp. |
| B.582 | GL | Phyllocoptruta spp. |
| B.583 | GL | Tetranychus spp. |
| B.584 | GL | Heterodera spp. |
| B.585 | GL | Meloidogyne spp. |
| B.586 | PL | Adoxophyes spp. |
| B.587 | PL | Agrotis spp. |
| B.588 | PL | *Alabama argillaceae* |
| B.589 | PL | *Anticarsia gemmatalis* |
| B.590 | PL | Chilo spp. |
| B.591 | PL | *Clysia ambiguella* |
| B.592 | PL | *Crocidolomia binotalis* |
| B.593 | PL | Cydia spp. |
| B.594 | PL | *Diaropsis castanea* |
| B.595 | PL | Earias spp. |
| B.596 | PL | Ephestia spp. |
| B.597 | PL | Heliothis spp. |
| B.598 | PL | Hellula undalis |
| B.599 | PL | *Keiferia lycopersicella* |
| B.600 | PL | *Leucoptera scitella* |
| B.601 | PL | Lithocollethis spp. |
| B.602 | PL | *Lobesia botrana* |
| B.603 | PL | *Ostrinia nubilalis* |
| B.604 | PL | Pandemis spp. |
| B.605 | PL | *Pectinophora gossyp.* |
| B.606 | PL | *Phyllocnistis citrella* |
| B.607 | PL | Pieris spp. |
| B.608 | PL | *Plutella xylostella* |
| B.609 | PL | Scirpophaga spp. |
| B.610 | PL | Sesamia spp. |
| B.611 | PL | Sparganothis spp. |
| B.612 | PL | Spodoptera spp. |
| B.613 | PL | Tortrix spp. |
| B.614 | PL | *Trichoplusia ni* |
| B.615 | PL | Agriotes spp. |
| B.616 | PL | Anthonomus grandis |
| B.617 | PL | Curculio spp. |
| B.618 | PL | *Diabrotica balteata* |
| B.619 | PL | Leptinotarsa spp. |
| B.620 | PL | Lissorhoptrus spp. |
| B.621 | PL | Otiorhynchus spp. |
| B.622 | PL | Aleurothrixus spp. |
| B.623 | PL | Aleyrodes spp. |
| B.624 | PL | Aonidiella spp. |
| B.625 | PL | Aphididae spp. |
| B.626 | PL | Aphis spp. |
| B.627 | PL | *Bemisia tabaci* |
| B.628 | PL | Empoasca spp. |
| B.629 | PL | Mycus spp. |
| B.630 | PL | Nephotettix spp. |
| B.631 | PL | Nilaparvata spp. |
| B.632 | PL | Pseudococcus spp. |
| B.633 | PL | Psylla spp. |
| B.634 | PL | Quadraspidiotus spp. |
| B.635 | PL | Schizaphis spp. |
| B.636 | PL | Trialeurodes spp. |
| B.637 | PL | Lyriomyza spp. |
| B.638 | PL | Oscinella spp. |
| B.639 | PL | Phorbia spp. |
| B.640 | PL | Frankliniella spp. |
| B.641 | PL | Thrips spp. |
| B.642 | PL | *Scirtothrips aurantii* |
| B.643 | PL | Aceria spp. |
| B.644 | PL | Aculus spp. |
| B.645 | PL | Brevipalpus spp. |
| B.646 | PL | Panonychus spp. |
| B.647 | PL | Phyllocoptruta spp. |
| B.648 | PL | Tetranychus spp. |
| B.649 | PL | Heterodera spp. |
| B.650 | PL | Meloidogyne spp. |
| B.651 | XN | Adoxophyes spp. |
| B.652 | XN | Agrotis spp. |
| B.653 | XN | *Alabama argillaceae* |
| B.654 | XN | *Anticarsia gemmatalis* |
| B.655 | XN | Chilo spp. |
| B.656 | XN | *Clysia ambiguella* |
| B.657 | XN | *Crocidolomia binotalis* |
| B.658 | XN | Cydia spp. |
| B.659 | XN | *Diparopsis castanea* |
| B.660 | XN | Earias spp. |
| B.661 | XN | Ephestia spp. |
| B.662 | XN | Heliothis spp. |
| B.663 | XN | *Hellula undalis* |
| B.664 | XN | *Keiferia lycopersicella* |
| B.665 | XN | *Leucoptera scitella* |
| B.666 | XN | Lithocollethis spp. |
| B.667 | XN | *Lobesia botrana* |
| B.668 | XN | *Ostrinia nubilalis* |
| B.669 | XN | Pandemis spp. |
| B.670 | XN | *Pectinophora gossyp.* |
| B.671 | XN | *Phyllocnistis citrella* |
| B.672 | XN | Pieris spp. |
| B.673 | XN | *Plutella xylostella* |
| B.674 | XN | Scirpophaga spp. |
| B.675 | XN | Sesamia spp. |
| B.676 | XN | Sparganothis spp. |
| B.677 | XN | Spodoptera spp. |
| B.678 | XN | Tortrix spp. |
| B.679 | XN | *Trichoplusia ni* |
| B.680 | XN | Agriotes spp. |
| B.681 | XN | Anthonomus grandis |
| B.682 | XN | Curculio spp. |
| B.683 | XN | *Diabrotica balteata* |
| B.684 | XN | Leptinotarsa spp. |
| B.685 | XN | Lissorhoptrus spp. |

TABLE B-continued

| | | |
|---|---|---|
| B.686 | XN | Otiorhynchus spp. |
| B.687 | XN | Aleurothrixus spp. |
| B.688 | XN | Aleyrodes spp. |
| B.689 | XN | Aonidiella spp. |
| B.690 | XN | Aphididae spp. |
| B.691 | XN | Aphis spp. |
| B.692 | XN | *Bemisia tabaci* |
| B.693 | XN | Empoasca spp. |
| B.694 | XN | Mycus spp. |
| B.695 | XN | Nephotettix spp. |
| B.696 | XN | Nilaparvata spp. |
| B.697 | XN | Pseudococcus spp. |
| B.698 | XN | Psylla spp. |
| B.699 | XN | Quadraspidiotus spp. |
| B.700 | XN | Schizaphis spp. |
| B.701 | XN | Trialeurodes spp. |
| B.702 | XN | Lyriomyza spp. |
| B.703 | XN | Oscinella spp. |
| B.704 | XN | Phorbia spp. |
| B.705 | XN | Frankliniella spp. |
| B.706 | XN | Thrips spp. |
| B.707 | XN | *Scirtothrips aurantii* |
| B.708 | XN | Aceria spp. |
| B.709 | XN | Aculus spp. |
| B.710 | XN | Brevipalpus spp. |
| B.711 | XN | Panonychus spp. |
| B.712 | XN | Phyllocoptruta spp. |
| B.713 | XN | Tetranychus spp. |
| B.714 | XN | Heterodera spp. |
| B.715 | XN | Meloidogyne spp. |
| B.716 | PInh. | Adoxophyes spp. |
| B.717 | PInh. | Agrotis spp. |
| B.718 | PInh. | *Alabama argillaceae* |
| B.719 | PInh. | *Anticarsia gemmatalis* |
| B.720 | PInh. | Chilo spp. |
| B.721 | PInh. | *Clysia ambiguella* |
| B.722 | PInh. | *Crocidolomia binotalis* |
| B.723 | PInh. | Cydia spp. |
| B.724 | PInh. | *Diparopsis castanea* |
| B.725 | PInh. | Earias spp. |
| B.726 | PInh. | Ephestia spp. |
| B.727 | PInh. | Heliothis spp. |
| B.728 | PInh. | *Hellula undalis* |
| B.729 | PInh. | *Keiferia lycopersicella* |
| B.730 | PInh. | *Leucoptera scitella* |
| B.731 | PInh. | Lithocollethis spp. |
| B.732 | PInh. | *Lobesia botrana* |
| B.733 | PInh. | *Ostrinia nubilalis* |
| B.734 | PInh. | Pandemis spp. |
| B.735 | PInh. | *Pectinophora gossyp.* |
| B.736 | PInh. | *Phyllocnistis citrella* |
| B.737 | PInh. | Pieris spp. |
| B.738 | PInh. | Plutella xylostella |
| B.739 | PInh. | Scirpophaga spp. |
| B.740 | PInh. | Sesamia spp. |
| B.741 | PInh. | Sparganothis spp. |
| B.742 | PInh. | Spodoptera spp. |
| B.743 | PInh. | Tortrix spp. |
| B.744 | PInh. | *Trichoplusia ni* |
| B.745 | PInh. | Agriotes spp. |
| B.746 | PInh. | *Anthonomus grandis* |
| B.747 | PInh. | Curculio spp. |
| B.748 | PInh. | *Diabrotica balteata* |
| B.749 | PInh. | Leptinotarsa spp. |
| B.750 | PInh. | Lissorhoptrus spp. |
| B.751 | PInh. | Otiorhynchus spp. |
| B.752 | PInh. | Aleurothrixus spp. |
| B.753 | PInh. | Aleyrodes spp. |
| B.754 | PInh. | Aonidiella spp. |
| B.755 | PInh. | Aphididae spp. |
| B.756 | PInh. | Aphis spp. |
| B.757 | PInh. | *Bemisia tabaci* |
| B.758 | PInh. | Empoasca spp. |
| B.759 | PInh. | Mycus spp. |
| B.760 | PInh. | Nephotettix spp. |
| B.761 | PInh. | Nilaparvata spp. |
| B.762 | PInh. | Pseudococcus spp. |
| B.763 | PInh. | Psylla spp. |
| B.764 | PInh. | Quadraspidiotus spp. |
| B.765 | PInh. | Schizaphis spp. |
| B.766 | PInh. | Trialeurodes spp. |
| B.767 | PInh. | Lyriomyza spp. |
| B.768 | PInh. | Oscinella spp. |
| B.769 | PInh. | Phorbia spp. |
| B.770 | PInh. | Frankliniella spp. |
| B.771 | PInh. | Thrips spp. |
| B.772 | PInh. | *Scirtothrips aurantii* |
| B.773 | PInh. | Aceria spp. |
| B.774 | PInh. | Aculus spp. |
| B.775 | PInh. | Brevipalpus spp. |
| B.776 | PInh. | Panonychus spp. |
| B.777 | PInh. | Phyllocoptruta spp. |
| B.778 | PInh. | Tetranychus spp. |
| B.779 | PInh. | Heterodera spp. |
| B.780 | PInh. | Meloidogyne spp. |
| B.781 | PLec. | Adoxophyes spp. |
| B.782 | PLec. | Agrotis spp. |
| B.783 | PLec. | *Alabama argillaceae* |
| B.784 | PLec. | *Anticarsia gemmatalis* |
| B.785 | PLec. | Chilo spp. |
| B.786 | PLec. | *Clysia ambiguella* |
| B.787 | PLec. | *Crocidolomia binotalis* |
| B.788 | PLec. | Cydia spp. |
| B.789 | PLec. | *Diparopsis castanea* |
| B.790 | PLec. | Earias spp. |
| B.791 | PLec. | Ephestia spp. |
| B.792 | PLec. | Heliothis spp. |
| B.793 | PLec. | *Hellula undalis* |
| B.794 | PLec. | *Keiferia lycopersicella* |
| B.795 | PLec. | *Leucoptera scitella* |
| B.796 | PLec. | Lithocollethis spp. |
| B.797 | PLec. | *Lobesia botrana* |
| B.798 | PLec. | *Ostrinia nubilalis* |
| B.799 | PLec. | Pandemis spp. |
| B.800 | PLec. | *Pectinophora gossyp.* |
| B.801 | PLec. | *Phyllocnistis citrella* |
| B.802 | PLec. | Pieris spp. |
| B.803 | PLec. | Plutella xylostella |
| B.804 | PLec. | Scirpophaga spp. |
| B.805 | PLec. | Sesamia spp. |
| B.806 | PLec. | Sparganothis spp. |
| B.807 | PLec. | Spodoptera spp. |
| B.808 | PLec. | Tortrix spp. |
| B.809 | PLec. | *Trichoplusia ni* |
| B.810 | PLec. | Agriotes spp. |
| B.811 | PLec. | *Anthonomus grandis* |
| B.812 | PLec. | Curculio spp. |
| B.813 | PLec. | *Diabrotica balteata* |
| B.814 | PLec. | Leptinotarsa spp. |
| B.815 | PLec. | Lissorhoptrus spp. |
| B.816 | PLec. | Otiorhynchus spp. |
| B.817 | PLec. | Aleurothrixus spp. |
| B.818 | PLec. | Aleyrodes spp. |
| B.819 | PLec. | Aonidiella spp. |
| B.820 | PLec. | Aphididae spp. |
| B.821 | PLec. | Aphis spp. |
| B.822 | PLec. | *Bemisia tabaci* |
| B.823 | PLec. | Empoasca spp. |
| B.824 | PLec. | Mycus spp. |
| B.825 | PLec. | Nephotettix spp. |
| B.826 | PLec. | Nilaparvata spp. |
| B.827 | PLec. | Pseudococcus spp. |

TABLE B-continued

| | | |
|---|---|---|
| B.828 | PLec. | Psylla spp. |
| B.829 | PLec. | Quadraspidiotus spp. |
| B.830 | PLec. | Schizaphis spp. |
| B.831 | PLec. | Trialeurodes spp. |
| B.832 | PLec. | Lyriomyza spp. |
| B.833 | PLec. | Oscinella spp. |
| B.834 | PLec. | Phorbia spp. |
| B.835 | PLec. | Frankliniella spp. |
| B.836 | PLec. | Thrips spp. |
| B.837 | PLec. | *Scirtothrips aurantii* |
| B.838 | PLec. | Aceria spp. |
| B.839 | PLec. | Aculus spp. |
| B.840 | PLec. | Brevipalpus spp. |
| B.841 | PLec. | Panonychus spp. |
| B.842 | PLec. | Phyllocoptruta spp. |
| B.843 | PLec. | Tetranychus spp. |
| B.844 | PLec. | Heterodera spp. |
| B.845 | PLec. | Meloidogyne spp. |
| B.846 | Aggl. | Adoxophyes spp. |
| B.847 | Aggl. | Agrotis spp. |
| B.848 | Aggl. | *Alabama argillaceae* |
| B.849 | Aggl. | *Anticarsia gemmatalis* |
| B.850 | Aggl. | Chilo spp. |
| B.851 | Aggl. | *Clysia ambiguella* |
| B.852 | Aggl. | *Crocidolomia binotalis* |
| B.853 | Aggl. | Cydia spp. |
| B.854 | Aggl. | *Diparopsis castanea* |
| B.855 | Aggl. | Earias spp. |
| B.856 | Aggl. | Ephestia spp. |
| B.857 | Aggl. | Heliothis spp. |
| B.858 | Aggl. | Hellula undalis |
| B.859 | Aggl. | *Keiferia lycopersicella* |
| B.860 | Aggl. | *Leucoptera scitella* |
| B.861 | Aggl. | Lithocollethis spp. |
| B.862 | Aggl. | *Lobesia botrana* |
| B.863 | Aggl. | Ostrinia nubilalis |
| B.864 | Aggl. | Pandemis spp. |
| B.865 | Aggl. | *Pectinophora gossyp.* |
| B.866 | Aggl. | *Phyllocnistis citrella* |
| B.867 | Aggl. | Pieris spp. |
| B.868 | Aggl. | Plutella xylostella |
| B.869 | Aggl. | Scirpophaga spp. |
| B.870 | Aggl. | Sesamia spp. |
| B.871 | Aggl. | Sparganothis spp. |
| B.872 | Aggl. | Spodoptera spp. |
| B.873 | Aggl. | Tortrix spp. |
| B.874 | Aggl. | *Trichoplusia ni* |
| B.875 | Aggl. | Agriotes spp. |
| B.876 | Aggi. | *Anthonomus grandis* |
| B.877 | Aggl. | Curculio spp. |
| B.878 | Aggl. | *Diabrotica balteata* |
| B.879 | Aggl. | Leptinotarsa spp. |
| B.880 | Aggl. | Lissorhoptrus spp. |
| B.881 | Aggl. | Otiorhynchus spp. |
| B.882 | Aggl. | Aleurothrixus spp. |
| B.883 | Aggl. | Aleyrodes spp. |
| B.884 | Aggl. | Aonidiella spp. |
| B.885 | Aggl. | Aphididae spp. |
| B.886 | Aggl. | Aphis spp. |
| B.887 | Aggl. | *Bemisia tabaci* |
| B.888 | Aggl. | Empoasca spp. |
| B.889 | Aggl. | Mycus spp. |
| B.890 | Aggl. | Nephotettix spp. |
| B.891 | Aggl. | Nilaparvata spp. |
| B.892 | Aggl. | Pseudococcus spp. |
| B.893 | Aggl. | Psylla spp. |
| B.894 | Aggl. | Quadraspidiotus spp. |
| B.895 | Aggl. | Schizaphis spp. |
| B.896 | Aggl. | Trialeurodes spp. |
| B.897 | Aggl. | Lyriomyza spp. |
| B.898 | Aggl. | Oscinella spp. |
| B.899 | Aggl. | Phorbia spp. |
| B.900 | Aggl. | Frankliniella spp. |
| B.901 | Aggl. | Thrips spp. |
| B.902 | Aggl. | *Scirtothrips aurantii* |
| B.903 | Aggl. | Aceria spp. |
| B.904 | Aggl. | Aculus spp. |
| B.905 | Aggl. | Brevipalpus spp. |
| B.906 | Aggl. | Panonychus spp. |
| B.907 | Aggl. | Phyllocoptruta spp. |
| B.908 | Aggl. | Tetranychus spp. |
| B.909 | Aggl. | Heterodera spp. |
| B.910 | Aggl. | Meloidogyne spp. |
| B.911 | CO | Adoxophyes spp. |
| B.912 | CO | Agrotis spp. |
| B.913 | CO | *Alabama argillaceae* |
| B.914 | CO | *Anticarsia gemmatalis* |
| B.915 | CO | Chilo spp. |
| B.916 | CO | *Clysia ambiguella* |
| B.917 | CO | *Crocidolomia binotalis* |
| B.918 | CO | Cydia spp. |
| B.919 | CO | *Diparopsis castanea* |
| B.920 | CO | Earias spp. |
| B.921 | CO | Ephestia spp. |
| B.922 | CO | Heliothis spp. |
| B.923 | CO | Hellula undalis |
| B.924 | CO | *Keiferia lycopersicella* |
| B.925 | CO | *Leucoptera scitella* |
| B.926 | CO | Lithocollethis spp. |
| B.927 | CO | *Lobesia botrana* |
| B.928 | CO | Ostrinia nubilalis |
| B.929 | CO | Pandemis spp. |
| B.930 | CO | *Pectinophora gossyp.* |
| B.931 | CO | *Phyllocnistis citrella* |
| B.932 | CO | Pieris spp. |
| B.933 | CO | Plutella xylostella |
| B.934 | CO | Scirpophaga spp. |
| B.935 | CO | Sesamia spp. |
| B.936 | CO | Sparganothis spp. |
| B.937 | CO | Spodoptera spp. |
| B.938 | CO | Tortrix spp. |
| B.939 | CO | *Trichoplusia ni* |
| B.940 | CO | Agriotes spp. |
| B.941 | CO | *Anthonomus grandis* |
| B.942 | CO | Curculio spp. |
| B.943 | CO | *Diabrotica balteata* |
| B.944 | CO | Leptinotarsa spp. |
| B.945 | CO | Lissorhoptrus spp. |
| B.946 | CO | Otiorhynchus spp. |
| B.947 | CO | Aleurothrixus spp. |
| B.948 | CO | Aleyrodes spp. |
| B.949 | CO | Aonidiella spp. |
| B.950 | CO | Aphididae spp. |
| B.951 | CO | Aphis spp. |
| B.952 | CO | *Bemisia tabaci* |
| B.953 | CO | Empoasca spp. |
| B.954 | CO | Mycus spp. |
| B.955 | CO | Nephotettix spp. |
| B.956 | CO | Nilaparvata spp. |
| B.957 | CO | Pseudococcus spp. |
| B.958 | CO | Psylla spp. |
| B.959 | CO | Quadraspidiotus spp. |
| B.960 | CO | Schizaphis spp. |
| B.961 | CO | Trialeurodes spp. |
| B.962 | CO | Lyriomyza spp. |
| B.963 | CO | Oscinella spp. |
| B.964 | CO | Phorbia spp. |
| B.965 | CO | Frankliniella spp. |
| B.966 | CO | Thrips spp. |
| B.967 | CO | *Scirtothrips aurantii* |
| B.968 | CO | Aceria spp. |

TABLE B-continued

| | | |
|---|---|---|
| B.969 | CO | Aculus spp. |
| B.970 | CO | Brevipalpus spp. |
| B.971 | CO | Panonychus spp. |
| B.972 | CO | Phyllocoptruta spp. |
| B.973 | CO | Tetranychus spp. |
| B.974 | CO | Heterodera spp. |
| B.975 | CO | Meloidogyne spp. |
| B.976 | CH | Adoxophyes spp. |
| B.977 | CH | Agrotis spp. |
| B.978 | CH | Alabama argillaceae |
| B.979 | CH | Anticarsia gemmatalis |
| B.980 | CH | Chilo spp. |
| B.981 | CH | Clysia ambiguella |
| B.982 | CH | Crocidolomia binotalis |
| B.983 | CH | Cydia spp. |
| B.984 | CH | Diparopsis castanea |
| B.985 | CH | Earias spp. |
| B.986 | CH | Ephestia spp. |
| B.987 | CH | Heliothis spp. |
| B.988 | CH | Hellula undalis |
| B.989 | CH | Keiferia lycopersicella |
| B.990 | CH | Leucoptera scitella |
| B.991 | CH | Lithocollethis spp. |
| B.992 | CH | Lobesia botrana |
| B.993 | CH | Ostrinia nubilalis |
| B.994 | CH | Pandemis spp. |
| B.995 | CH | Pectinophora gossyp. |
| B.996 | CH | Phyllocnistis citrella |
| B.997 | CH | Pieris spp. |
| B.998 | CH | Plutella xylostella |
| B.999 | CH | Scirpophaga spp. |
| B.1000 | CH | Sesamia spp. |
| B.1001 | CH | Sparganothis spp. |
| B.1002 | CH | Spodoptera spp. |
| B.1003 | CH | Tortrix spp. |
| B.1004 | CH | Trichoplusia ni |
| B.1005 | CH | Agriotes spp. |
| B.1006 | CH | Anthonomus grandis |
| B.1007 | CH | Curculio spp. |
| B.1008 | CH | Diabrotica balteata |
| B.1009 | CH | Leptinotarsa spp. |
| B.1010 | CH | Lissorhoptrus spp. |
| B.1011 | CH | Otiorhynchus spp. |
| B.1012 | CH | Aleurothrixus spp. |
| B.1013 | CH | Aleyrodes spp. |
| B.1014 | CH | Aonidiella spp. |
| B.1015 | CH | Aphididae spp. |
| B.1016 | CH | Aphis spp. |
| B.1017 | CH | Bemisia tabaci |
| B.1018 | CH | Empoasca spp. |
| B.1019 | CH | Mycus spp. |
| B.1020 | CH | Nephotettix spp. |
| B.1021 | CH | Nilaparvata spp. |
| B.1022 | CH | Pseudococcus spp. |
| B.1023 | CH | Psylla spp. |
| B.1024 | CH | Quadraspidiotus spp. |
| B.1025 | CH | Schizaphis spp. |
| B.1026 | CH | Trialeurodes spp. |
| B.1027 | CH | Lyriomyza spp. |
| B.1028 | CH | Oscinella spp. |
| B.1029 | CH | Phorbia spp. |
| B.1030 | CH | Frankliniella spp. |
| B.1031 | CH | Thrips spp. |
| B.1032 | CH | Scirtothrips aurantii |
| B.1033 | CH | Aceria spp. |
| B.1034 | CH | Aculus spp. |
| B.1035 | CH | Brevipalpus spp. |
| B.1036 | CH | Panonychus spp. |
| B.1037 | CH | Phyllocoptruta spp. |
| B.1038 | CH | Tetranychus spp. |
| B.1039 | CH | Heterodera spp. |
| B.1040 | CH | Meloidogyne spp. |
| B.1041 | SS | Adoxophyes spp. |
| B.1042 | SS | Agrotis spp. |
| B.1043 | SS | Alabama argillaceae |
| B.1044 | SS | Anticarsia gemmatalis |
| B.1045 | SS | Chilo spp. |
| B.1046 | SS | Clysia ambiguella |
| B.1047 | SS | Crocidolomia binotalis |
| B.1048 | SS | Cydia spp. |
| B.1049 | SS | Diparopsis castanea |
| B.1050 | SS | Earias spp. |
| B.1051 | SS | Ephestia spp. |
| B.1052 | SS | Heliothis spp. |
| B.1053 | SS | Hellula undalis |
| B.1054 | SS | Keiferia lycopersicella |
| B.1055 | SS | Leucoptera scitella |
| B.1056 | SS | Lithocollethis spp. |
| B.1057 | SS | Lobesia botrana |
| B.1058 | SS | Ostrinia nubilalis |
| B.1059 | SS | Pandemis spp. |
| B.1060 | SS | Pectinophora gossyp. |
| B.1061 | SS | Phyllocnistis citrella |
| B.1062 | SS | Pieris spp. |
| B.1063 | SS | Plutella xylostella |
| B.1064 | SS | Scirpophaga spp. |
| B.1065 | SS | Sesamia spp. |
| B.1066 | SS | Sparganothis spp. |
| B.1067 | SS | Spodoptera spp. |
| B.1068 | SS | Tortrix spp. |
| B.1069 | SS | Trichoplusia ni |
| B.1070 | SS | Agriotes spp. |
| B.1071 | SS | Anthonomus grandis |
| B.1072 | SS | Curculio spp. |
| B.1073 | SS | Diabrotica balteata |
| B.1074 | SS | Leptinotarsa spp. |
| B.1075 | SS | Lissorhoptrus spp. |
| B.1076 | SS | Otiorhynchus spp. |
| B.1077 | SS | Aleurothrixus spp. |
| B.1078 | SS | Aleyrodes spp. |
| B.1079 | SS | Aonidiella spp. |
| B.1080 | SS | Aphididae spp. |
| B.1081 | SS | Aphis spp. |
| B.1082 | SS | Bemisia tabaci |
| B.1083 | SS | Empoasca spp. |
| B.1084 | SS | Mycus spp. |
| B.1085 | SS | Nephotettix spp. |
| B.1086 | SS | Nilaparvata spp. |
| B.1087 | SS | Pseudococcus spp. |
| B.1088 | SS | Psylla spp. |
| B.1089 | SS | Quadraspidiotus spp. |
| B.1090 | SS | Schizaphis spp. |
| B.1091 | SS | Trialeurodes spp. |
| B.1092 | SS | Lyriomyza spp. |
| B.1093 | SS | Oscinella spp. |
| B.1094 | SS | Phorbia spp. |
| B.1095 | SS | Frankliniella spp. |
| B.1096 | SS | Thrips spp. |
| B.1097 | SS | Scirtothrips aurantii |
| B.1098 | SS | Aceria spp. |
| B.1099 | SS | Aculus spp. |
| B.1100 | SS | Brevipalpus spp. |
| B.1101 | SS | Panonychus spp. |
| B.1102 | SS | Phyllocoptruta spp. |
| B.1103 | SS | Tetranychus spp. |
| B.1104 | SS | Heterodera spp. |
| B.1105 | SS | Meloidogyne spp. |
| B.1106 | HO | Adoxophyes spp. |
| B.1107 | HO | Agrotis spp. |
| B.1108 | HO | Alabama argillaceae |

TABLE B-continued

| | | |
|---|---|---|
| B.1109 | HO | *Anticarsia gemmatalis* |
| B.1110 | HO | Chilo spp. |
| B.1111 | HO | *Clysia ambiguella* |
| B.1112 | HO | *Crocidolomia binotalis* |
| B.1113 | HO | Cydia spp. |
| B.1114 | HO | *Diparopsis castanea* |
| B.1115 | HO | Earias spp. |
| B.1116 | HO | Ephestia spp. |
| B.1117 | HO | Heliothis spp. |
| B.1118 | HO | *Hellula undalis* |
| B.1119 | HO | *Keiferia lycopersicella* |
| B.1120 | HO | *Leucoptera scitella* |
| B.1121 | HO | Lithocollethis spp. |
| B.1122 | HO | *Lobesia botrana* |
| B.1123 | HO | *Ostrinia nubilalis* |
| B.1124 | HO | Pandemis spp. |
| B.1125 | HO | *Pectinophora gossypiella* |
| B.1126 | HO | *Phyllocnistis citrella* |
| B.1127 | HO | Pieris spp. |
| B.1128 | HO | *Plutella xylostella* |
| B.1129 | HO | Scirpophaga spp. |
| B.1130 | HO | Sesamia spp. |
| B.1131 | HO | Sparganothis spp. |
| B.1132 | HC | Spodoptera spp. |
| B.1133 | HO | Tortrix spp. |
| B.1134 | HO | *Trichoplusia ni* |
| B.1135 | HO | Agriotes spp. |
| B.1136 | HO | *Anthonomus grandis* |
| B.1137 | HO | Curculio spp. |
| B.1138 | HO | *Diabrotica balteata* |
| B.1139 | HO | Leptinotarsa spp. |
| B.1140 | HO | Lissorhoptrus spp. |
| B.1141 | HO | Otiorhynchus spp. |
| B.1142 | HO | Aleurothrixus spp. |
| B.1143 | HO | Aleyrodes spp. |
| B.1144 | HO | Aonidiella spp. |
| B.1145 | HO | Aphididae spp. |
| B.1146 | HO | Aphis spp. |
| B.1147 | HO | *Bemisia tabaci* |
| B.1148 | HO | Empoasca spp. |
| B.1149 | HO | Mycus spp. |
| B.1150 | HO | Nephotettix spp. |
| B.1151 | HO | Nilaparvata spp. |
| B.1152 | HO | Pseudococcus spp. |
| B.1153 | HO | Psylla spp. |
| B.1154 | HO | Quadraspidiotus spp. |
| B.1155 | HO | Schizaphis spp. |
| B.1156 | HO | Trialeurodes spp. |
| B.1157 | HO | Lyriomyza spp. |
| B.1158 | HO | Oscinella spp. |
| B.1159 | HO | Phorbia spp. |
| B.1160 | HO | Frankliniella spp. |
| B.1161 | HO | Thrips spp. |
| B.1162 | HO | *Scirtothrips aurantii* |
| B.1163 | HO | Aceria spp. |
| B.1164 | HO | Aculus spp. |
| B.1165 | HO | Brevipalpus spp. |
| B.1166 | HO | Panonychus spp. |
| B.1167 | HO | Phyllocoptruta spp. |
| B.1168 | HO | Tetranychus spp. |
| B.1169 | HO | Heterodera spp. |
| B.1170 | HO | Meloidogyne spp. |

BIOLOGICAL EXAMPLES

TABLE 1

A method of controlling pests comprising the application of pymetrozine to transgenic cotton, wherein the combination of the active principle expressed by the transgenic plant and the pest to be controlled correspond to anyone of the lines B.1 to B.1170 of table B.

TABLE 2

A method of controlling pests comprising the application of pymetrozine to transgenic rice, wherein the combination of the active principle expressed by the transgenic plant and the pest to be controlled correspond to anyone of the lines B.1 to B.1170 of table B.

TABLE 3

A method of controlling pests comprising the application of to transgenic potatoes, wherein the combination of the active principle expressed by the transgenic plant and the pest to be controlled correspond to anyone of the lines B.1 to B.1170 of table B.

TABLE 4

A method of controlling pests comprising the application of pymetrozine to transgenic brassica, wherein the combination of the active principle expressed by the transgenic plant and the pest to be controlled correspond to anyone of the lines B.1 to B.1170 of table B.

TABLE 5

A method of controlling pests comprising the application of pymetrozine to transgenic tomatoes, wherein the combination of the active principle expressed by the transgenic plant and the pest to be controlled correspond to anyone of the lines B.1 to B.1170 of table B.

TABLE 6

A method of controlling pests comprising the application of pymetrozine to transgenic cucurbits, wherein the combination of the active principle expressed by the transgenic plant and the pest to be controlled correspond to anyone of the lines B.1 to B.1170 of table B.

TABLE 7

A method of controlling pests comprising the application of pymetrozine to transgenic soybeans, wherein the combination of the active principle expressed by the transgenic plant and the pest to be controlled correspond to anyone of the lines B.1 to B.1170 of table B.

TABLE 8

A method of controlling pests comprising the application of pymetrozine to transgenic maize, wherein the combination of the active principle expressed by the transgenic plant and the pest to be controlled correspond to anyone of the lines B.1 to B.1170 of table B.

TABLE 9

A method of controlling pests comprising the application of pymetrozine to transgenic wheat, wherein the combination of the active principle expressed by the transgenic plant and the pest to be controlled correspond to anyone of the lines B.1 to B.1170 of table B.

TABLE 10

A method of controlling pests comprising the application of pymetrozine to transgenic bananas, wherein the combination of the active principle expressed by the transgenic plant and the pest to be controlled correspond to anyone of the lines B.1 to B.1170 of table B.

TABLE 11

A method of controlling pests comprising the application of pymetrozine to transgenic citrus trees, wherein the combination of the active principle expressed by the transgenic plant and the pest to be controlled correspond to anyone of the lines B.1 to B.1170 of table B.

TABLE 12

A method of controlling pests comprising the application of pymetrozine to transgenic pome fruit trees, wherein the combination of the active principle expressed by the transgenic plant and the pest to be controlled correspond to anyone of the lines B.1 to B.1170 of table B.

TABLE 13

A method of controlling pests comprising the application of lufenuron to transgenic cotton, wherein the combination of the active principle expressed by the transgenic plant and the pest to be controlled correspond to anyone of the lines B.1 to B.1170 of table B.

TABLE 14

A method of controlling pests comprising the application of lufenuron to transgenic rice, wherein the combination of the active principle expressed by the transgenic plant and the pest to be controlled correspond to anyone of the lines B.1 to B.1170 of table B.

TABLE 15

A method of controlling pests comprising the application of lufenuron to transgenic potatoes, wherein the combination of the active principle expressed by the transgenic plant and the pest to be controlled correspond to anyone of the lines B.1 to B.1170 of table B.

TABLE 16

A method of controlling pests comprising the application of lufenuron to transgenic tomatoes, wherein the combination of the active principle expressed by the transgenic plant and the pest to be controlled correspond to anyone of the lines B.1 to B.1170 of table B.

TABLE 17

A method of controlling pests comprising the application of lufenuron to transgenic cucurbits, wherein the combination of the active principle expressed by the transgenic plant and the pest to be controlled correspond to anyone of the lines B.1 to B.1170 of table B.

TABLE 18

A method of controlling pests comprising the application of lufenuron to transgenic soybeans, wherein the combination of the active principle expressed by the transgenic plant and the pest to be controlled correspond to anyone of the lines B.1 to B.1170 of table B.

TABLE 19

A method of controlling pests comprising the application of lufenuron to transgenic maize, wherein the combination of the active principle expressed by the transgenic plant and the pest to be controlled correspond to anyone of the lines B.1 to B.1170 of table B.

TABLE 20

A method of controlling pests comprising the application of lufenuron to transgenic wheat, wherein the combination of the active principle expressed by the transgenic plant and the pest to be controlled correspond to anyone of the lines B.1 to B.1170 of table B.

TABLE 21

A method of controlling pests comprising the application of lufenuron to transgenic bananas, wherein the combination of the active principle expressed by the transgenic plant and the pest to be controlled correspond to anyone of the lines B.1 to B.1170 of table B.

TABLE 22

A method of controlling pests comprising the application of lufenuron to transgenic orange trees, wherein the combination of the active principle expressed by the transgenic plant and the pest to be controlled correspond to anyone of the lines B.1 to B.1170 of table B.

TABLE 23

A method of controlling pests comprising the application of lufenuron to transgenic pome fruit, wherein the combination of the active principle expressed by the transgenic plant and the pest to be controlled correspond to anyone of the lines B.1 to B.1170 of table B.

TABLE 24

A method of controlling pests comprising the application of lufenuron to transgenic cucurbits, wherein the combination of the active principle expressed by the transgenic plant and the pest to be controlled correspond to anyone of the lines B.1 to B.1170 of table B.

TABLE 25

A method of controlling pests comprising the application of fenoxycarb to transgenic cotton, wherein the combination of the active principle expressed by the transgenic plant and the pest to be controlled correspond to anyone of the lines B.1 to B.1170 of table B.

TABLE 26

A method of controlling pests comprising the application of fenoxycarb to transgenic rice, wherein the combination of the active principle expressed by the transgenic plant and the pest to be controlled correspond to anyone of the lines B.1 to B.1170 of table B.

TABLE 27

A method of controlling pests comprising the application of fenoxycarb to transgenic potatoes, wherein the combination of the active principle expressed by the transgenic plant and the pest to be controlled correspond to anyone of the lines B.1 to B.1170 of table B.

TABLE 28

A method of controlling pests comprising the application of fenoxycarb to transgenic brassica, wherein the combination of the active principle expressed by the transgenic plant and the pest to be controlled correspond to anyone of the lines B.1 to B.1170 of table B.

TABLE 29

A method of controlling pests comprising the application of fenoxycarb to transgenic tomatoes, wherein the combination of the active principle expressed by the transgenic plant and the pest to be controlled correspond to anyone of the lines B.1 to B.1170 of table B.

TABLE 30

A method of controlling pests comprising the application of fenoxycarb to transgenic cucurbits, wherein the combination of the active principle expressed by the transgenic plant and the pest to be controlled correspond to anyone of the lines B.1 to B.1170 of table B.

TABLE 31

A method of controlling pests comprising the application of fenoxycarb to transgenic soybeans, wherein the combination of the active principle expressed by the transgenic plant and the pest to be controlled correspond to anyone of the lines B.1 to B.1170 of table B.

TABLE 32

A method of controlling pests comprising the application of fenoxycarb to transgenic maize, wherein the combination of the active principle expressed by the transgenic plant and the pest to be controlled correspond to anyone of the lines B.1 to B.1170 of table B.

TABLE 33

A method of controlling pests comprising the application of fenoxycarb to transgenic wheat, wherein the combination of the active principle expressed by the transgenic plant and the pest to be controlled correspond to anyone of the lines B.1 to B.1170 of table B.

TABLE 34

A method of controlling pests comprising the application of fenoxycarb to transgenic bananas, wherein the combination of the active principle expressed by the transgenic plant and the pest to be controlled correspond to anyone of the lines B.1 to B.1170 of table B.

TABLE 35

A method of controlling pests comprising the application of fenoxycarb to transgenic citrus trees, wherein the combination of the active principle expressed by the transgenic plant and the pest to be controlled correspond to anyone of the lines B.1 to B.1170 of table B.

TABLE 36

A method of controlling pests comprising the application of fenoxycarb to transgenic pome fruit trees, wherein the combination of the active principle expressed by the transgenic plant and the pest to be controlled correspond to anyone of the lines B.1 to B.1170 of table B.

TABLE 37

A method of controlling pests comprising the application of profenofos to transgenic cotton, wherein the combination of the active principle expressed by the transgenic plant and the pest to be controlled correspond to anyone of the lines B.1 to B.1170 of table B.

TABLE 38

A method of controlling pests comprising the application of profenofos to transgenic rice, wherein the combination of the active principle expressed by the transgenic plant and the pest to be controlled correspond to anyone of the lines B.1 to B.1170 of table B.

TABLE 39

A method of controlling pests comprising the application profenofos of to transgenic potatoes, wherein the combination of the active principle expressed by the transgenic plant and the pest to be controlled correspond to anyone of the lines B.1 to B.1170 of table B.

TABLE 40

A method of controlling pests comprising the application of profenofos to transgenic brassica, wherein the combination of the active principle expressed by the transgenic plant and the pest to be controlled correspond to anyone of the lines B.1 to B.1170 of table B.

TABLE 41

A method of controlling pests comprising the application of profenofos to transgenic tomatoes, wherein the combination of the active principle expressed by the transgenic plant and the pest to be controlled correspond to anyone of the lines B.1 to B.1170 of table B.

TABLE 42

A method of controlling pests comprising the application of profenofos to transgenic cucurbits, wherein the combination of the active principle expressed by the transgenic plant and the pest to be controlled correspond to anyone of the lines B.1 to B.1170 of table B.

TABLE 43

A method of controlling pests comprising the application of profenofos to transgenic soybeans, wherein the combination of the active principle expressed by the transgenic plant and the pest to be controlled correspond to anyone of the lines B.1 to B.1170 of table B.

TABLE 44

A method of controlling pests comprising the application of profenofos to transgenic maize, wherein the combination of the active principle expressed by the transgenic plant and the pest to be controlled correspond to anyone of the lines B.1 to B.1170 of table B.

TABLE 45

A method of controlling pests comprising the application of profenofos to transgenic wheat, wherein the combination of the active principle expressed by the transgenic plant and the pest to be controlled correspond to anyone of the lines B.1 to B.1170 of table B.

TABLE 46

A method of controlling pests comprising the application of profenofos to transgenic bananas, wherein the combination of the active principle expressed by the transgenic plant and the pest to be controlled correspond to anyone of the lines B.1 to B.1170 of table B.

TABLE 47

A method of controlling pests comprising the application of profenofos to transgenic citrus trees, wherein the combination of the active principle expressed by the transgenic plant and the pest to be controlled correspond to anyone of the lines B.1 to B.1170 of table B.

TABLE 48

A method of controlling pests comprising the application of profenofos to transgenic pome fruit trees, wherein the combination of the active principle expressed by the transgenic plant and the pest to be controlled correspond to anyone of the lines B.1 to B.1170 of table B.

TABLE C

Abbreviations:
Acetyl-COA Carboxylase: ACCase
Acetolactate Synthase: ALS
Hydroxyphenylpyruvat dioxygenase: HPPD
Inhibition of protein synthesis: IPS
Hormone mimic: HO
Glutamine Synthetase: GS
Protoporphyrinogen oxidase: PROTOX
5-Enolpyruvyl-3-Phosphoshikimate Synthase: EPSPS

| | Principle | Tolerant to | Crop |
|---|---|---|---|
| C.1 | ALS | Sulfonylureas etc. *** | Cotton |
| C.2 | ALS | Sulfonylureas etc. *** | Rice |
| C.3 | ALS | Sulfonylureas etc. *** | Brassica |
| C.4 | ALS | Sulfonylureas etc. *** | Potatoes |
| C.5 | ALS | Sulfonylureas etc. *** | Tomatoes |
| C.6 | ALS | Sulfonylureas etc. *** | Cucurbits |
| C.7 | ALS | Sulfonylureas etc. *** | Soybeans |
| C.8 | ALS | Sulfonylureas etc. *** | Maize |
| C.9 | ALS | Sulfonylureas etc. *** | Wheat |
| C.10 | ALS | Sulfonylureas etc. *** | pome fruit |
| C.11 | ALS | Sulfonylureas etc. *** | stone fruit |
| C.12 | ALS | Sulfonylureas etc. *** | citrus |
| C.13 | ACCase | +++ | Cotton |
| C.14 | ACCase | +++ | Rice |
| C.15 | ACCase | +++ | Brassica |
| C.16 | ACCase | +++ | Potatoes |
| C.17 | ACCase | +++ | Tomatoes |
| C.18 | ACCase | +++ | Cucurbits |
| C.19 | ACCase | +++ | Soybeans |
| C.20 | ACCase | +++ | Maize |
| C.21 | ACCase | +++ | Wheat |
| C.22 | ACCase | +++ | pome fruit |
| C.23 | ACCase | +++ | stone fruit |
| C.24 | ACCase | +++ | citrus |
| C.25 | HPPD | Isoxaflutol, Isoxachlotol, Sulcotrion, Mesotrion | Cotton |
| C.26 | HPPD | Isoxaflutol, Isoxachlotol, Sulcotrion, Mesotrion | Rice |
| C.27 | HPPD | Isoxaflutol, Isoxachlotol, Sulcotrion, Mesotrion | Brassica |
| C.28 | HPPD | Isoxaflutol, Isoxachlotol, Sulcotrion, Mesotrion | Potatoes |
| C.29 | HPPD | Isoxaflutol, Isoxachlotol, Sulcotrion, Mesotrion | Tomatoes |
| C.30 | HPPD | Isoxaflutol, Isoxachlotol, Sulcotrion, Mesotrion | Cucurbits |
| C.31 | HPPD | Isoxaflutol, Isoxachlotol, Sulcotrion, Mesotrion | Soybeans |
| C.32 | HPPD | Isoxaflutol, Isoxachlotol, Sulcotrion, Mesotrion | Maize |

TABLE C-continued

Abbreviations:
Acetyl-COA Carboxylase: ACCase
Acetolactate Synthase: ALS
Hydroxyphenylpyruvat dioxygenase: HPPD
Inhibition of protein synthesis: IPS
Hormone mimic: HO
Glutamine Synthetase: GS
Protoporphyrinogen oxidase: PROTOX
5-Enolpyruvyl-3-Phosphoshikimate Synthase: EPSPS

| | Principle | Tolerant to | Crop |
|---|---|---|---|
| C.33 | HPPD | Isoxaflutol, Isoxachlotol, Sulcotrion, Mesotrion | Wheat |
| C.34 | HPPD | Isoxaflutol, Isoxachlotol, Sulcotrion, Mesotrion | pome fruit |
| C.35 | HPPD | Isoxaflutol, Isoxachlotol, Sulcotrion, Mesotrion | stone fruit |
| C.36 | HPPD | Isoxaflutol, Isoxachlotol, Sulcotrion, Mesotrion | citrus |
| C.37 | Nitrilase | Bromoxynil, Ioxynil | Cotton |
| C.38 | Nitrilase | Bromoxynil, Ioxynil | Rice |
| C.39 | Nitrilase | Bromoxynil, Ioxynil | Brassica |
| C.40 | Nitrilase | Bromoxynil, Ioxynil | Potatoes |
| C.41 | Nitrilase | Bromoxynil, Ioxynil | Tomatoes |
| C.42 | Nitrilase | Bromoxynil, Ioxynil | Cucurbits |
| C.43 | Nitrilase | Bromoxynil, Ioxynil | Soybeans |
| C.44 | Nitrilase | Bromoxynil, Ioxynil | Maize |
| C.45 | Nitrilase | Bromoxynil, Ioxynil | Wheat |
| C.46 | Nitrilase | Bromoxynil, Ioxynil | pome fruit |
| C.47 | Nitrilase | Bromoxynil, Ioxynil | stone fruit |
| C.48 | Nitrilase | Bromoxynil, Ioxynil | citrus |
| C.49 | IPS | Chloroactanilides &&& | Cotton |
| C.50 | IPS | Chloroactanilides &&& | Rice |
| C.51 | IPS | Chloroactanilide &&&s | Brassica |
| C.52 | IPS | Chloroactanilides &&& | Potatoes |
| C.53 | IPS | Chloroactanilides &&& | Tomatoes |
| C.54 | IPS | Chloroactanilides &&& | Cucurbits |
| C.55 | IPS | Chloroactanilides &&& | Soybeans |
| C.56 | IPS | Chloroactanilides &&& | Maize |
| C.57 | IPS | Chloroactanilides &&& | Wheat |
| C.58 | IPS | Chloroactanilides &&& | pome fruit |
| C.59 | IPS | Chloroactanilides &&& | stone fruit |
| C.60 | IPS | Chloroactanilides &&& | citrus |
| C.61 | HOM | 2,4-D,Mecoprop-P | Cotton |
| C.62 | HOM | 2,4-D,Mecoprop-P | Rice |
| C.63 | HOM | 2,4-D,Mecoprop-P | Brassica |
| C.64 | HOM | 2,4-D,Mecoprop-P | Potatoes |
| C.65 | HOM | 2,4-D,Mecoprop-P | Tomatoes |
| C.66 | HOM | 2,4-D,Mecoprop-P | Cucurbits |
| C.67 | HOM | 2,4-D,Mecoprop-P | Soybeans |
| C.68 | HOM | 2,4-D,Mecoprop-P | Maize |
| C.69 | HOM | 2,4-D,Mecoprop-P | Wheat |
| C.70 | HOM | 2,4-D,Mecoprop-P | pome fruit |
| C.71 | HOM | 2,4-D,Mecoprop-P | stone fruit |
| C.72 | HOM | 2,4-D,Mecoprop-P | citrus |
| C.73 | PROTOX | Protox inhibitors /// | Cotton |
| C.74 | PROTOX | Protox inhibitors /// | Rice |
| C.75 | PROTOX | Protox inhibitors /// | Brassica |
| C.76 | PROTOX | Protox inhibitors /// | Potatoes |
| C.77 | PROTOX | Protox inhibitors /// | Tomatoes |
| C.78 | PROTOX | Protox inhibitors /// | Cucurbits |
| C.79 | PROTOX | Protox inhibitors /// | Soybeans |
| C.80 | PROTOX | Protox inhibitors /// | Maize |
| C.81 | PROTOX | Protox inhibitors /// | Wheat |
| C.82 | PROTOX | Protox inhibitors /// | pome fruit |
| C.83 | PROTOX | Protox inhibitors /// | stone fruit |
| C.84 | PROTOX | Protox inhibitors /// | citrus |
| C.85 | EPSPS | Glyphosate and/or Sulphosate | Cotton |
| C.86 | EPSPS | Glyphosate and/or Sulphosate | Rice |
| C.87 | EPSPS | Glyphosate and/or Sulphosate | Brassica |
| C.88 | EPSPS | Glyphosate and/or Sulphosate | Potatoes |
| C.89 | EPSPS | Glyphosate and/or Sulphosate | Tomatoes |
| C.90 | EPSPS | Glyphosate and/or Sulphosate | Cucurbits |
| C.91 | EPSPS | Glyphosate and/or Sulphosate | Soybeans |
| C.92 | EPSPS | Glyphosate and/or Sulphosate | Maize |
| C.93 | EPSPS | Glyphosate and/or Sulphosate | Wheat |
| C.94 | EPSPS | Glyphosate and/or Sulphosate | pome fruit |

TABLE C-continued

Abbreviations:
Acetyl-COA Carboxylase: ACCase
Acetolactate Synthase: ALS
Hydroxyphenylpyruvat dioxygenase: HPPD
Inhibition of protein synthesis: IPS
Hormone mimic: HO
Glutamine Synthetase: GS
Protoporphyrinogen oxidase: PROTOX
5-Enolpyruvyl-3-Phosphoshikimate Synthase: EPSPS

| | Principle | Tolerant to | Crop |
|---|---|---|---|
| C.95 | EPSPS | Glyphosate and/or Sulphosate | stone fruit |
| C.96 | EPSPS | Glyphosate and/or Sulphosate | citrus |
| C.97 | GS | Gluphosinate and/or Bialaphos | Cotton |
| C.98 | GS | Gluphosinate and/or Bialaphos | Rice |
| C.99 | GS | Gluphosinate and/or Bialaphos | Brassica |
| C.100 | GS | Gluphosinate and/or Bialaphos | Potatoes |
| C.101 | GS | Gluphosinate and/or Bialaphos | Tomatoes |
| C.102 | GS | Gluphosinate and/or Bialaphos | Cucurbits |
| C.103 | GS | Gluphosinate and/or Bialaphos | Soybeans |
| C.104 | GS | Gluphosinate and/or Bialaphos | Maize |
| C.105 | GS | Gluphosinate and/or Bialaphos | Wheat |
| C.106 | GS | Gluphosinate and/or Bialaphos | pome fruit |
| C.107 | GS | Gluphosinate and/or Bialaphos | stone fruit |
| C.108 | GS | Gluphosinate and/or Bialaphos | citrus |

*** Included are Sulfonylureas, Imidazolinones, Triazolopyrimidines, Dimethoxypyrimidines and N-Acylsulfonamides:
Sulfonylureas such as Chlorsulfuron, Chlorimuron, Ethamethsulfuron, Metsulfuron, Primisulfuron, Prosulfuron, Triasulfuron, Cinosulfuron, Trifusulfuron, Oxasulfuron, Bensulfuron, Tribenuron, ACC 322140, Fluzasulfuron, Ethoxysulfuron, Fluzasdulfuron, Nicosulfuron, Rimsulfuron, Thifensulfuron, Pyrazosulfuron, Clopyrasulfuron, NC 330, Azimsulfuron, Imazosulfuron, Sulfosulfuron, Amidosulfuron, Flupyrsulfuron, CGA 362622 Imidazolinones such as Imazamethabenz, Imazaquin, Imazamethypyr, Imazethapyr, Imazapyr and Imazamox;
Triazolopyrimidines such as DE 511, Flumetsulam and Chloransulam;
Dimethoxypyrimidines such as Pyrithiobac, Pyriminobac, Bispyribac and Pyribenzoxim.
+++ Tolerant to Diclofop-methyl, Fluazifop-P-butyl, Haloxyfop-P-methyl, Haloxyfop-P-ethyl, Quizalafop-P-ethyl, clodinafop propargyl, fenoxaprop-ethyl, -Tepraloxydim, Alloxydim, Sethoxydim, Cycloxydim, Cloproxydim, Tralkoxydim, Butoxydim, Caloxydim, Clefoxydim, Clethodim.
&&& Chloroacetanilides such as Alachlor Acetochlor, Dimethenamid
/// Protox inhibitors: For instance diphenyethers such as Acifluorfen, Aclonifen, Bifenox, Chlornitrofen, Ethoxyfen, Fluoroglycofen, Fomesafen, Lactofen, Oxyfluorfen; Imides such as Azafenidin, Carfentrazone-ethyl, Cinidon-ethyl, Flumiclorac-pentyl, Flumioxazin, Fluthiacet-methyl, Oxadiargyl, Oxadiazon, Pentoxazone, Sulfentrazone, Imides and others, such as Flumipropyn, Flupropacil, Nipyraclofen and Thidiazimin; and further Fluazolate and Pyraflufen-ethyl

BIOLOGICAL EXAMPLES

TABLE 49

A method of controlling representatives of the genus Adoxophyes comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 50

A method of controlling representatives of the genus Agrotis comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 51

A method of controlling *Alabama argillaceae* comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 52

A method of controlling *Anticarsia gemmatalis* comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 53

A method of controlling representatives of the genus Chilo comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 54

A method of controlling *Clysia ambiguella* comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 55

A method of controlling representatives of the genus Cnephalocrocis comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 56

A method of controlling *Crocidolomia binotalis* comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 57

A method of controlling representatives of the genus Cydia comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 58

A method of controlling *Diparopsis castanea* comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 59

A method of controlling representatives of the genus Earias comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 60

A method of controlling representatives of the genus Ephestia comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 61

A method of controlling representatives of the genus Heliothis comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 62

A method of controlling *Hellula undalis* comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 63

A method of controlling *Keiferia lycopersicella* comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 64

A method of controlling *Leucoptera scitella* comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 65

A method of controlling representatives of the genus Lithocollethis comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 66

A method of controlling *Lobesia botrana* comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 67

A method of controlling *Ostrinia nubilalis* comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 68

A method of controlling representatives of the genus Pandemis comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 69

A method of controlling *Pectinophora gossypiella* comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 70

A method of controlling *Phyllocnistis citrella* comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 71

A method of controlling representatives of the genus Pieris comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 72

A method of controlling *Plutella xylostella* comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 73

A method of controlling representatives of the genus Scirpophaga comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 74

A method of controliing representatives of the genus Sesamia comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 75

A method of controlling representatives of the genus Sparganothis comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 76

A method of controlling representatives of the genus Spodoptera comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 77

A method of controlling representatives of the genus Tortrix comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 78

A method of controlling *Trichoplusia ni* comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 79

A method of controlling representatives ot the genus Agriotes comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 80

A method of controlling *Anthonomus grandis* comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 81

A method of controlling representatives of the genus Curculio comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 82

A method of controlling *Diabrotica balteata* comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 83

A method of controlling representatives of the genus Leptinotarsa comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 84

A method of controlling representatives of the genus Lissorhoptrus comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 85

A method of controlling representatives of the genus Otiorhynchus comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 86

A method of controlling representatives of the genus Aleurothrixus comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 87

A method of controlling representatives of the genus Aleyrodes comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 88

A method of controlling representatives of the genus Aonidiella comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 89

A method of controlling representatives of the family Aphididae comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 90

A method of controlling representatives of the genus Aphis comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 91

A method of controlling *Bernisia tabaci* comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 92

A method of controlling representatives of the genus Empoasca comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 93

A method of controlling representatives of the genus Mycus comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 94

A method of controlling representatives of the genus Nephotettix comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 95

A method of controlling representatives of the genus Nilaparvata comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 96

A method of controlling representatives of the genus Pseudococcus comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 97

A method of controlling representatives of the genus Psylla comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 98

A method of controlling representatives of the genus Quadraspidiotus comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 99

A method of controlling representatives of the genus Schizaphis comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 100

A method of controlling representatives of the genus Trialeurodes comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 101

A method to controlling representatives of the genus Lyriomyza comprising the application of pymetrozine to a herbicidally resistant transgenic crop, wherein the combination to the active principle expressed by the transgenic plant and the crop to be protected against the pest correspond to anyone of the lines C.1 to C.108 of table C.

TABLE 102

A method of controlling representatives of the genus Oscinella comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 103

A method of controlling representatives of the genus Phorbia comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 104

A method of controlling representatives of the genus Frankliniella comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 105

A method of controlling representatives of the genus Thrips comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 106

A method of controlling *Scirtothrips aurantii* comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 107

A method of controlling representatives of the genus Aceria comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 108

A method of controlling representatives of the genus Aculus comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 109

A method of controlling representatives of the genus Brevipaipus comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 110

A method of controlling representatives of the genus Panonychus comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 111

A method of controlling representatives of the genus Phyllocoptruta comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 112

A method of controlling representatives of the genus Tetranychus comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 113

A method of controlling representatives of the genus Heterodera comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 114

A method of controlling representatives of the genus Meloidogyne comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 115

A method of controlling *Mamestra brassica* comprising the application of pymetrozine to a herbicidally resistant transgenic crop, wherein the combination of the active principle expressed by the transgenic plant and the crop to be protected against the pest correspond to anyone of the lines C.1 to C.108 of table C.

TABLE 116

A method of controlling representatives of the genus Adoxophyes comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 117

A method of controlling representatives of the genus Agrotis comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 118

A method of controlling *Alabama argillaceae* comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 119

A method of controlling *Anticarsia gemmatalis* comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 120

A method of controlling representatives of the genus Chilo comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 121

A method of controlling *Clysia ambiguella* comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 122

A method of controlling representatives of the genus Cnephalocrocis comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 124

A method of controlling representatives of the genus Cydia comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 125

A method of controlling *Diparopsis castanea* comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 126

A method of controlling representatives of the genus Earias comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 127

A method of controlling representatives of the genus Ephestia comprising the application of lufenuron to a herbicidally resistant transgenic crop, wherein the combination of the active principle expressed by the transgenic plant and the crop to be protected against the pest correspond to anyone of the lines C1 to C.108 of table C.

TABLE 128

A method of controlling representatives of the genus Heliothis of lufenuron to a herbicidally resistant transgenic crop, wherein the combination of the active principle expressed by the transgenic plant and the crop to be protected against the pest correspond to anyone of the lines C.1 to C.108 of table C.

TABLE 129

A method of controlling *Hellula undalis* comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 130

A method of controlling *Keiferia lycopersicella* comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 131

A method of controlling *Leucoptera scitella* comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 132

A method of controlling representatives of the genus Lithocollethis comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 133

A method of controlling *Lobesia botrana* comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 134

A method of controlling *Ostrinia nubilalis* comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 135

A method of controlling representatives of the genus Pandemis comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 136

A method of controlling *Pectinophora gossypiella* comprising the application of lufenuron to a herbicidally resistant transgenic crop wherein the combination of the active principle expressed by the transgenic plant and the crop to be protected against the pest correspond to anyone of the lines C.1 to C.108 of table C.

TABLE 137

A method of controlling *Phyllocnistis citrella* comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 138

A method of controlling representatives of the genus Pieris comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 139

A method of controlling *Plutella xylostella* comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 140

A method of controlling representatives of the genus Scirpophaga comprising the application of Iufenuron to a herbicidally resistant transgenic crop, wherein the combination of the active principle expressed by the transgenic plant and the crop to be protected against the pest correspond to anyone of the lines C.1 to C.108 of table C.

TABLE 141

A method of controlling representatives of the genus Sesamia comprising the application of Iufenuron to a herbicidally resistant transgenic crop, wherein the combination of the active principle expressed by the transgenic plant and the crop to be protected against the pest correspond to anyone of the lines C.1 to C.108 of table C.

TABLE 142

A method of controlling representatives of the genus Sparganothis comprising the application of Iufenuron to a herbicidally resistant transgenic crop, wherein the combination of the active principle expressed by the transgenic plant and the crop to be protected against the pest correspond to anyone of the lines C.1 to C.108 of table C.

TABLE 143

A method of controlling representatives of the genus Spodoptera comprising the application of Iufenuron to a herbicidally resistant transgenic crop, wherein the combination of the active principle expressed by the transgenic plant and the crop to be protected against the pest correspond to anyone of the lines C.1 to C.108 of table C.

TABLE 144

A method of controlling representatives of the genus Tortrix comprising the application of Iufenuron to a herbicidally resistant transgenic crop, wherein the combination of the active principle expressed by the transgenic plant and the crop to be protected against the pest correspond to anyone of the lines C.1 to C.108 of table C.

TABLE 145

A method of controlling *Trichoplusia ni* comprising the application of Iufenuron to a herbicidally resistant transgenic crop, wherein the combination of the active principle expressed by the transgenic plant and the crop to be protected against the pest correspond to anyone of the lines C.1 to C.108 of table C.

TABLE 146

A method of controlling representatives of the genus Agriotes comprising the application of Iufenuron to a herbicidally resistant transgenic crop, wherein the combination of the active principle expressed by the transgenic plant and the crop to be protected against the pest correspond to anyone of the lines C.1 to C.108 of table C.

TABLE 147

A method of controlling *Anthonomus grandis* comprising the application of Iufenuron to a herbicidally resistant transgenic crop, wherein the combination of the active principle expressed by the transgenic plant and the crop to be protected against the pest correspond to anyone of the lines C.1 to C.108 of table C.

TABLE 148

A method of controlling representatives of the genus Curculio comprising the application of Iufenuron to a herbicidally resistant transgenic crop, wherein the combination of the active principle expressed by the transgenic plant and the crop to be protected against the pest correspond to anyone of the lines C.1 to C.108 of table C.

TABLE 149

A method of controlling *Diabrotica balteata* comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 150

A method of controlling representatives of the genus Leptinotarsa comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 151

A method of controlling representatives of the genus Lissorhoptrus comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 152

A method of controlling representatives of the genus Otiorhynchus comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 153

A method of controlling representatives of the genus Aleurothrixus comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 154

A method of controlling representatives of the genus Aleyrodes comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 155

A method of controlling representatives of the genus Aonidiella comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 156

A method of controlling representatives of the family Aphididae comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 157

A method of controlling representatives of the genus Aphis comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 158

A method of controlling *Bemisia tabaci* comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 159

A method of controlling representatives of the genus Empoasca comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 160

A method of controlling representatives of the genus Mycus comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 161

A method of controlling representatives of the genus Nephotettix comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 162

A method of controlling representatives of the genus Nilaparvata comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 163

A method of controlling representatives of the genus Pseudococcus comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 164

A method of controlling representatives of the genus Psylla comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 165

A method of controlling representatives of the genus Quadraspidiotus comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 166

A method of controlling representatives of the genus Schizaphis comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 167

A method of controlling representatives of the genus Trialeurodes comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 168

A method of controlling representatives of the genus Lyriomyza comprising the application of lufenuron to a herbicidally resistant transgenic crop, wherein the combination of the active principle expressed by the transgenic plant and the crop to be protected against the pest correspond to anyone of the Lines C.1 to C.108 of table C.

TABLE 169

A method of controlling representatives of the genus Oscinella comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 170

A method of controlling representatives of the genus Phorbia composing the application of lufenuron to a herbicidally resistant transgenic crop, wherein the combination of the active principle expressed by the transgenic plant and the crop to be protected against the pest correspond to anyone of the lines C.1 to C.108 of table C.

TABLE 171

A method of controlling representatives of the genus Frankliniella comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 172

A method of controlling representatives of the genus Thrips comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 173

A method of controlling *Scirtothrips aurantii* comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 174

A method of controlling representatives of the genus Aceria comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 175

A method of controlling representatives of the genus Aculus comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 176

A method of controlling representatives of the genus Brevipalpus comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 177

A method of controlling representatives of the genus Panonychus comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 178

A method of controlling representatives of the genus Phyllocoptruta comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 179

A method of controlling representatives of the genus Tetranychus comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 180

A method of controlling representatives of the genus Heterodera comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 181

A method of controlling representatives of the genus Meloidogyne comprising the application of lufenuron to a herbicidally resistant transgenic crop, wherein the combination of the active principle expressed by the transgenic plant and the crop to be protected against the pest correspond to anyone of the lines C.1 to C.108 of table C.

TABLE 182

A method of controlling representatives of the genus Adoxophyes comprising the application of fenoxycarb to a herbicidally resistant transgenic crop, wherein thecombination of the active principle expressed by the transgenic plant and the crop to be protected against the pest correspond to anyone of the lines C.1 to C.108 of table C.

TABLE 183

A method of controlling representatives of the genus Agrotis comprising the application of fenoxycarb to a herbicidally resistant transgenic crop, transgenic plant and the crop to be wherein the combination of the active principle expressed by the protected against the pest correspond to anyone of the lines C.1 to C.108 of table C.

TABLE 184

A method of controlling Alabama argillaceae comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 185

A method of controlling Anticarsia gemmatalis comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 186

A method of controlling representatives of the genus Chilo comprising the application of tenoxycarb to a herbicidally resistant transgenic crop, wherein the combination of the active principle expressed by the transgenic plant and the crop to be protected against the pest correspond to anyone of the lines C.1 to C.108 of table C.

TABLE 187

A method of controlling Clysia ambiguella comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 188

A method of controlling Crocidolomia binotalis comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 189

A method of controlling representatives of the genus Cydia comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 190

A method of controlling Diparopsis castanea comprising the application of fenoxycarb to a herbicidally resistant transgenic crop, wherein the combination of the active principle expressed by the transgenic plant and the crop to be protected against the pest correspond to anyone of the lines C.1 to C 108 of table C.

TABLE 191

A method of controlling representatives of the genus Earias comprising the application of tenoxycarb to a herbicidally resistant transgenic crop, wherein the combination of the active principle expressed by the transgenic plant and the crop to be protected against the pest correspond to anyone of the lines C.1 to C.108 of table C.

TABLE 192

A method of controlling representatives of the genus Ephestia comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 193

A method of controlling representatives of the genus Heliothis of fenoxycarb to a herbicidally resistant transgenic crop, wherein the combination of the active principle expressed by the transgenic plant and the crop to be protected against the pest correspond to anyone of the lines C.1 to C.108 of table C.

TABLE 194

A method of controlling *Hellula undalis* comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 195

A method of controlling *Keiferia lycopersicella* comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 196

A method of controlling *Leucoptera scitella* comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 197

A method of controlling representatives of the genus Lithocollethis comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 198

A method of controlling *Lobesia botrana* comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 199

A method of controlling *Ostrinia nubilalis* comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 200

A method of controlling representatives of the genus Pandemis comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 201

A method of controlling *Pectinophora gossypiella* comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 202

A method of controlling *Phyllocnistis citrella* comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 203

A method of controlling representatives of the genus Pieris comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 204

A method of controlling Plutella xylostella comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 205

A method of controlling representatives of the genus Scirpophaga comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 206

A method of controlling representatives of the genus Sesamia comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 207

A method of controlling representatives of the genus Sparganothis comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 208

A method of controlling representatives of the genus Spodoptera comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 209

A method of controlling representatives of the genus Tortrix comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 210

A method of controlling Trichoplusia ni comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 211

A method of controlling representatives of the genus Agriotes comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 212

A method of controlling Anthonomus grandis comprising the application of fenoxycarb to a herbicidally resistant transgenic crop, wherein the combination of the active principle expressed by the transgenic plant and the crop to be protected against the pest correspond to anyone of the lines C.1 to C.108 to table C.

TABLE 213

A method of controlling representatives of the genus Curculio comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 214

A method of controlling *Diabrotica balteata* comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 215

A method of controlling representatives of the genus Leptinotarsa comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 216

A method of controlling representatives of the genus Lissorhoptrus comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 217

A method of controlling representatives of the genus Otiorhynchus comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 218

A method of controlling representatives of the genus Aleurothrixus comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 219

A method of controlling representatives of the genus Aleyrodes comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 220

A method of controlling representatives of the genus Aonidiella comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 221

A method of controlling representatives of the family Aphididae comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 222

A method of controlling representatives of the genus Aphis comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 223

A method of controlling *Bemisia tabaci* comprising the application of fenoxycarb to a herbicidally resistant transgenic crop, wherein the combination of the active principle expressed by the transgenic plant and the crop to be protected against the pest correspond to anyone to the lines C.1 to C.108 of table C.

TABLE 224

A method of controlling representatives of the genus Empoasca comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 225

A method of controlling representatives of the genus Mycus comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 226

A method of controlling representatives of the genus Nephotettix comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 227

A method of controlling representatives of the genus Nilaparvata comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 228

A method of controlling representatives of the genus Pseudococcus comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 229

A method of controlling representatives of the genus Psylla comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 230

A method of controlling representatives of the genus Quadraspidiotus comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 231

A method of controlling representatives of the genus Schizaphis comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 232

A method of controlling representatives of the genus Trialeurodes comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 233

A method of controlling representatives of the genus Lyriomyza comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 234

A method of controlling representatives of the genus Oscinella comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 235

A method of controlling representatives of the genus Phorbia comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 236

A method of controlling representatives of the genus Frankliniella comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 237

A method of controlling representatives of the genus Thrips comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 238

A method of controlling *Scirtothrips aurantii* comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 239

A method of controlling representatives of the genus Aceria comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 240

A method of controlling representatives of the genus Aculus comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 241

A method of controlling representatives of the genus Brevipalpus comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 242

A method of controlling representatives of the genus Panonychus comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 243

A method of controlling representatives of the genus Phyllocoptruta comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 244

A method of controlling representatives of the genus Tetranychus comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 245

A method of controlling representatives of the genus Heterodera comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 246

A method of controlling representatives of the genus Meloidogyne comprising the application of fenoxycarb to a herbicidally resistant transgenic crop, wherein the combination of the active principle expressed by the transgenic plant and the crop to be protected against the pest correspond to anyone of the lines C.1 to C.108 of table C.

TABLE 247

A method of controlling *Mamestra brassica* comprising the application of fenoxycarb to a herbicidally resistant transgenic crop, wherein the combination of the active principle expressed by the transgenic plant and the crop to be protected against the pest correspond to anyone of the lines C.1 to C.108 of table C.

EXAMPLE B1

Action Against *Anthonomus Grandis* Adults. *SpodoDtera Littoralis* or *Heliothis virescens*

Young transgenic cotton plants which express the δ-endotoxin CryIIIA are sprayed with an aqueous emulsion spray mixture comprising 100, 50, 10, 5, 1 ppm of profenofos respectively. After the spray coating has dried on, the cotton plants are populated with 10 adult *Anthonomus grandis*, 10 *Spodoptera littora* larvae or 10 *Heliothis virescens* larvae respectively and introduced into a plastic container. Evaluation takes place 3 to 10 days later. The percentage reduction in population, or the percentage reduction in feeding damage (% action), is determined by comparing the number of dead beetles and the feeding damage on the transgenic cotton plants with that of non-transgenic cotton plants which have been treated with an emulsion spray mixture comprising lufenuron and conventional CryIIIA-toxin at a concentration of in each case 100, 50, 10, 5, 1 ppm respectively.

In this test, the control of the tested insects in the transgenic plant is superior to the control on the non-transgenic plant.

EXAMPLE B2

Action Against *Anthonomus Grandis* Adults, *Spodoptera littoralis* or *Heliothis virescens*

Young transgenic cotton plants which express the δ-endotoxin CryIIIA are sprayed with an aqueous emulsion spray mixture comprising 100, 50, 10, 5, 1 ppm of profenofos respectively. After the spray coating has dried on, the cotton plants are populated with 10 adult *Anthonomus grandis*, 10 *Spodoptera littora* larvae or 10 *Heliothis virescens* larvae respectively and introduced into a plastic container. Evaluation takes place 3 to 10 days later. The percentage reduction in population, or the percentage reduction in feeding damage (% action), is determined by comparing the number of dead beetles and the feeding damage on the transgenic cotton plants with that of non-transgenic cotton plants which have been treated with an emulsion spray mixture comprising pymetrozine and conventional CryIIIA-toxin at a concentration of in each case 100, 50, 10, 5, 1 ppm respectively.

In this test, the control of the tested insects in the transgenic plant is superior, while it is insufficient in the non-transgenic plant.

EXAMPLE B3

Action Against *Anthonomus Grandis* Adults. *Spodoptera littoralis* or *Heliothis virescens*

Young transgenic cotton plants which express tho δ-endotoxin CryIa (c) are sprayed with an aqueous emulsion spray mixture comprising 100, 50, 10, 5, 1 ppm of fenoxycarb respectively. After the spray coating has dried on, the cotton plants are populated with 10 adult *Anthonomus grandis*, 10 *Spodoptera littora* larvae or 10 *Heliothis virescens* larvae respectively and introduced into a plastic container. Evaluation takes place 3 to 10 days later. The percentage reduction in population, or the percentage reduction in feeding damage (% action), is determined by comparing the number of dead beetles and the feeding damage on the transgenic cotton plants with that of non-transgenic cotton plants which have been treated with an emulsion spray mixture comprising fenoxycarb and con-ventional CryIIIA-toxin at a concentration of in each case 100, 50, 10, 5, 1 ppm respectively.

In this test, the control of the tested insects in the transgenic plant is superior, while it is insufficient in the non-transgenic plant.

EXAMPLE B4

Action Against *Anthonomus Grandis* Adults, *Spodoptera Littoralis* or *Heliothis virescens*

Young transgenic cotton plants which express the δ-endotoxin CryIa(c) are sprayed with an aqueous emulsion spray mixture comprising 100, 50, 10, 5, 1 ppm of fenoxycarb respectively. After the spray coating has dried on, the cotton plants are populated with 10 adult *Anthonomus grandis*, 10 *Spodoptera littora* larvae or 10 *Heliothis virescens* larvae respectively and introduced into a plastic container. Evaluation takes place 3 to 10 days later. The percentage reduction in population, or the percentage reduction in feeding damage (% action), is determined by comparing the number of dead beetles and the feeding damage on the transgenic cotton plants with that of non-transgenic cotton plants which have been treated with an emulsion spray mixture comprising fenoxycarb and conventional CryIIIA-toxin at a concentration of in each case 100, 50, 10, 5, 1 ppm respectively.

In this test, the control of the tested insects in the transgenic plant is superior, while it is insufficient in the non-transgenic plant.

EXAMPLE B5

Action Against *Anthonomus Grandis* Adults, *Spodoptera littora* or *Heliothis virescens*

Young transgenic cotton plants which express the δ-endotoxin CryIa(c) are sprayed with an aqueous emulsion spray mixture comprising 100, 50, 10, 5, 1 ppm of pymetrozine respectively. After the spray coating has dried on, the cotton plants are populated with 10 adult *Anthonomus grandis*, 10 *Spodoptera littora* larvae or 10 *Heliothis virescens* larvae respectively and introduced into a plastic container. Evaluation takes place 3 to 10 days later. The percentage reduction in population, or the percentage reduction in feeding damage (% action), is determined by comparing the number of dead beetles and the feeding damage on the transgenic cotton plants with that of non-transgenic cotton plants which have been treated with an emulsion spray mixture comprising pymetrozine and conventional CryIIIA-toxin at a concentration of in each case 100, 50, 10, 5, 1 ppm respectively.

In this test, the control of the tested insects in the transgenic plant is superior, while it is insufficient in the non-transgenic plant.

EXAMPLE B6

Action Against *Anthonomus Grandis* Adults, *Spodoptera littoralis* or *Heliothis virescens*

Young transgenic cotton plants which express the δ-endotoxin CryIa(c) are sprayed with an aqueous emulsion spray mixture comprising 100, 50, 10, 5, 1 ppm of lufenuron respectively. After the spray coating has dried on, the cotton plants are populated with 10 adult *Anthonomus grandis*, 10*Spodoptera littora* larvae or 10*Heliothis virescens* larvae respectively and introduced into a plastic container. Evaluation takes place 3 to 10 days later. The percentage reduction in population, or the percentage reduction in feeding damage (% action), is determined by comparing the number of dead beetles and the feeding damage on the transgenic cotton plants with that of non-transgenic cotton plants which have been treated with an emulsion spray mixture comprising lufenuron conventional CryIIIA-toxin at a concentration of in each case 100, 50, 10, 5, 1 ppm respectively.

In this test, the control of the tested insects in the transgenic plant is superior, while it is insufficient in the non-transgenic plant.

EXAMPLE B7

Action Against *Ostrinia nubilalis*, Spodoptera spp. or Heliothis spp.

A plot (a) planted with maize cv. KnockOut® and an adjacent plot (b) of the same size which is planted with conventional maize, both showing natural infestation with *Ostrinia nubilalis*, Spodoptera sp or Heliothis, are sprayed with an aqueous emulsion spray mixture comprising 200, 100, 50, 10, 5, 1 ppm of fenoxycarb . Immediately afterwards, plot (b) is treated with an emulsion spray mixture comprising 200, 100, 50, 10, 5, 1 ppm of the endotoxin expressed by KnockOut®. Evaluation takes place 6 days later. The percentage reduction in population (% action) is determined by comparing the number of dead pests on the plants of plot (a) with that on the plants of plot (b).

Improved control of *Ostrinia nubilalis*, Spodoptera spD. or Heliothis is observed on the plants of plot (a), while plot (b) shows a control level of not over 60%.

EXAMPLE B8

Action Against *Ostrinia Nubilalis*. Spodoptera spp. or Heliothis spp.

A plot (a) planted with maize cv. KnockOut® and an adjacent plot (b) of the same size which is planted with conventional maize, both showing natural infestation with *Ostrinia nubilalis*, Spodoptera sp or Heliothis, are sprayed with an aqueous emulsion spray mixture comprising 200, 100, 50, 10, 5, 1 ppm of pymetrozine. Immediately afterwards, plot (b) is treated with an emulsion spray mixture comprising 200, 100, 50, 10, 5, 1 ppm of the endotoxin expressed by KnockOut®. Evaluation takes place 6 days later. The percentage reduction in population (% action) is determined by comparing the number of dead pests on the plants of plot (a) with that on the plants of plot (b).

Improved control of *Ostrinia nubilalis*, Spodoptera Spp. or Heliothis is observed on the plants of plot (a), while plot (b) shows a control level of not over 60%.

EXAMPLE B9

Action Against *Ostrinia Nubilalis*, Spodoptera spp. or Heliothis spp.

A plot (a) planted with maize cv. KnockOut® and an adjacent plot (b) of the same size which is planted with conventional maize, both showing natural infestation with *Ostrinia nubilalis*. Spodoptera sp or Heliothis, are sprayed with an aqueous emulsion spray mixture comprising 200, 100, 50, 10, 5, 1ppm of lufenuron. Immediately afterwards, plot (b) is treated with an emulsion spray mixture comprising 200, 100, 50, 10, 5, 1 ppm of the endotoxin expressed by KnockOut®. Evaluation takes place 6 days later. The percentage reduction in population (% action) is determined by comparing the number of dead pests on the plants of plot (a) with that on the plants of plot (b).

Improved control of *Ostrinia Nubilalis*, Spodoptera spp. or Heliothis spp. is observed on the plants of plot (a), while plot (b) shows a control level of not over 60%.

EXAMPLE B10

Action Against *Aphis Gossypii*

Cotton seedlings on a plot (a) expressing the δ-endotoxin CrylIIa on a plot (a) and conven-tional cotton seedlings on a plot (b) are infected with Aphis gossypi and subsequently sprayed with a spray mixture comprising 400 ppm pymetrozine. immediately afterwards, plot (b) is treated with an emulsion spray mixture comprising 400 ppm of the δ-endotoxin Crylila. The seedlings of plot (a) and (b) are then incubated at 20° C. The test is evaluated after 3 and 6 days.

The percentage reduction in population (% action) is determined by comparing the number of dead pests on the plants of plot (a) with that on the plants of plot (b). Improved control of *Aphis aossypi* is observed on the plants of plot (a), while plot (b) shows a control level of not over 60%.

EXAMPLE B11

Action Against *Frankliniella occidentalis*

Cotton seedlings expressing the δ-endotoxin Crylila on a plot (a) and conventional cotton seedlings on a plot (b) are infected with Frankliniella occidentalis and subsequently sprayed with a spray mixture comprising 400 ppm lufenuron. Immediately afterwards, plot (b) is treated with an emulsion spray mixture comprising 400 ppm of the S-endotoxin CrylIIa. The seedlings of plot (a) and (b) are then incubated at 20° C. The test is evaluated after 3 and 6 days.

The percentage reduction in population (% action) is determined by comparing the number of dead pests on the plants of plot (a) with that on the plants of plot (b). Improved control of *Frankliniella occidentalis* is observed on the plants of plot (a), while plot (b) shows a control level of not over 60%.

EXAMPLE B12

Action Against *Aphis gossypii*

Cotton seedlings expressing the δ-endotoxin CryIA(c) on a plot (a) and conventional cotton seedlings on a plot (b) are infected with Aphis gossypii and subsequently sprayed with a spray mixture comprising 400 ppm pymetrozine. Immediately afterwards, plot (b) is treated with an emulsion spray mixture comprising 400 ppm of the δ-endotoxin Crylla. The seedlings of plot (a) and (b) are then incubated at 20° C. The test is evaluated after 3 and 6 days.

The percentage reduction in population (% action) is determined by comparing the number of dead pests on the plants of plot (a) with that on the plants of plot (b). Improved control of *Aphis gossypii* is observed on the plants of plot (a), while plot (b) shows a control level of not over 60%.

EXAMPLE B13

Action Against *Frankliniella occidentalis*

Cotton seedlings expressing the δ-endotoxin CryIa(c) on a plot (a) and conventional cotton seedlings on a plot (b) are infected with Frankliniella occidentalis and subsequently sprayed with a spray mixture comprising 400 ppm lufenuron. Immediately afterwards, plot (b) is treated with an emulsion spray mixture comprising 400 ppm of the δ-endotoxin CryIa(c). The seedlings of plot (a) and (b) are then incubated at 20° C. The test is evaluated after 3 and 6 days.

The percentage reduction in population (% action) is determined by comparing the number of dead pests on the plants of plot (a) with that on the plants of plot (b). Improved control of *Frankliniella occidentalis* is observed on the plants of plot (a), while plot (b) shows a control level of not over 60%.

What is claimed is:

1. Method of controlling pests in crops of transgenic maize plants, where a pesticidal composition comprising pymetrozine, in free form or in agrochemically useful salt form as active ingredient and at least one auxiliary, is applied to the pests or their environment at a rate of 1 to 2000 g of active ingredient per hectare, wherein the pymetrozine compound produces synergistic results with said transgenic maize plants.

2. Method of claim 1 where the transgenic maize plant is treated.

3. Method of claim 1 where the propagation material of the transgenic maize plant is treated.

* * * * *